US009090911B2

(12) United States Patent
O'Neill et al.

(10) Patent No.: US 9,090,911 B2
(45) Date of Patent: Jul. 28, 2015

(54) MODIFIED ARTHROPOD AND METHOD OF USE

(71) Applicant: Monash University, Clayton (AU)

(72) Inventors: Scott Leslie O'Neill, South Melbourne (AU); Conor James McMeniman, New York, NY (US); Karyn Nicole Johnson, Tarragindi (AU); Elizabeth Ann McGraw, Windsor (AU); Luciano A. Moreira, Belo Horizonte (BR); Peter Anthony Ryan, Pullenvale (AU); Brian Herbert Kay, West End (AU); Jeremy Colin Brownlie, Brisbane (AU)

(73) Assignee: Monash University, Clayton (AU)

( * ) Notice: Subject to any disclaimer, the term of this patent is extended or adjusted under 35 U.S.C. 154(b) by 0 days.

(21) Appl. No.: 14/304,919

(22) Filed: Jun. 14, 2014

(65) Prior Publication Data

US 2014/0298501 A1    Oct. 2, 2014

Related U.S. Application Data

(63) Continuation of application No. 12/817,933, filed on Jun. 17, 2010, now abandoned.

(60) Provisional application No. 61/187,805, filed on Jun. 17, 2009.

(30) Foreign Application Priority Data

Oct. 2, 2009  (AU) ................................. 2009222557

(51) Int. Cl.
| | | |
|---|---|---|
| C12N 1/00 | (2006.01) | |
| A01N 63/00 | (2006.01) | |
| A01N 65/00 | (2009.01) | |
| A61K 39/00 | (2006.01) | |
| A61K 39/02 | (2006.01) | |
| C12N 15/87 | (2006.01) | |

(Continued)

(52) U.S. Cl.
CPC .............. *C12N 15/87* (2013.01); *A01K 67/033* (2013.01); *A01K 67/0337* (2013.01); *A01N 63/00* (2013.01); *C12N 15/01* (2013.01); *C12R 1/01* (2013.01); *A01K 2227/70* (2013.01); *A01K 2227/706* (2013.01); *A01K 2267/02* (2013.01)

(58) Field of Classification Search
CPC . A61K 2039/55; A61K 35/64; A61K 35/642; A61K 35/66; A61K 35/68; A61K 35/74; C12N 15/8281; C12N 15/8282; C12N 15/8285; C12N 15/8286; C12N 15/8287; C12N 15/87; C12N 5/0601
See application file for complete search history.

(56) References Cited

PUBLICATIONS

McMeniman et al., (Science. Jan. 2, 2009. vol. 323: 141-144).*

(Continued)

*Primary Examiner* — Ja'na Hines
(74) *Attorney, Agent, or Firm* — Leydig, Voit & Mayer, Ltd.

(57) ABSTRACT

A modified arthropod, an arthropod-modifying bacterium, and use thereof as an agent for control of diseases transmitted by arthropods, particularly mosquitoes, is provided. More specifically, an isolated arthropod-adapted *Wolbachia* bacterium capable of modifying one or more biological properties of a mosquito host is provided. The modified arthropod may be characterized as having a shortened life-span, a reduced ability to transmit disease, a reduced susceptibility to a pathogen, a reduced fecundity, and/or a reduced ability to feed from a host, when compared to a corresponding wild-type arthropod.

16 Claims, 54 Drawing Sheets
(20 of 54 Drawing Sheet(s) Filed in Color)

(51) Int. Cl.
  *A01K 67/033* (2006.01)
  *C12N 15/01* (2006.01)
  *C12R 1/01* (2006.01)

(56) References Cited

PUBLICATIONS

Min et al., (PNAS. 1997. vol. 94:10792-10796).*
Yeap et al., (Genetics. 2011. vol. 187:583-595).*
McMeniman et al., (PLoS Negl Trop Dis. Jul. 2010; 4(7): e748).*
Haine, "Symbiont-mediated protection," *Proceedings of the Royal Society B*, 275: 353-361 (2008).
McGraw et al., "Beyond insecticides: new thinking on an ancient problem," *Nature Reviews*, 11: 181-193 (Mar. 2013).
McMeniman et al., "Stable Introduction of a Life-Shortening *Wolbachia* Infection into the Mosquito *Aedes aegypti*," *Science*, 323: 141-144 (Jan. 2, 2009).
McMeniman et al., "A Virulent *Wolbachia* Infection Decreases the Viability of the Dengue Vector *Aedes aegypti* during Periods of Embryonic Quiescence," *PLoS*, 4(7): 1-6 (Jul. 2010).
Min et al., "*Wolbachia*, normally a symbiont of *Drosophila*, can be virulent, causing degeneration and early death," *Proc. Natl. Acad. Sci. USA*, 94: 10792-10796 (Sep. 1997).
Panteleev et al., "The Endosymbiotic Bacterium *Wolbachia* Enhances the Nonspecific Resistance to Insect Pathogens and Alters Behavior of *Drosophila melanogaster*," *Russian Journal of Genetics*, 43(9): 1066-1069 (2007).
Ruang-Areerate et al., "*Wolbachia* transinfection in *Aedes aegypti*: A potential gene driver of dengue vectors," *PNAS*, 103(33): 12534-12539 (Aug. 15, 2006).
Teixeira et al., "The Bacterial Symbiont *Wolbachia* Induces Resistance to RNA Viral Infections in *Drosophila melanogaster*," *PLoS Biology*, 6(12): 2753-2763 (Dec. 2008).
Xi et al., "*Wolbachia* Establishment and Invasion in an *Aedes aegypti* Laboratory Population," *Science*, 310: 326-328 (Oct. 14, 2005).
Xi et al., "The *Aedes aegypti* Toll Pathway Controls Dengue Virus Infection," *PLoS Pathogens*, 4(7): 1-12 (Jul. 2008).

\* cited by examiner

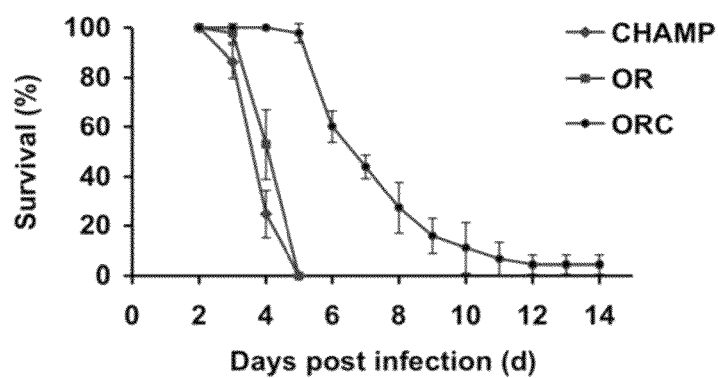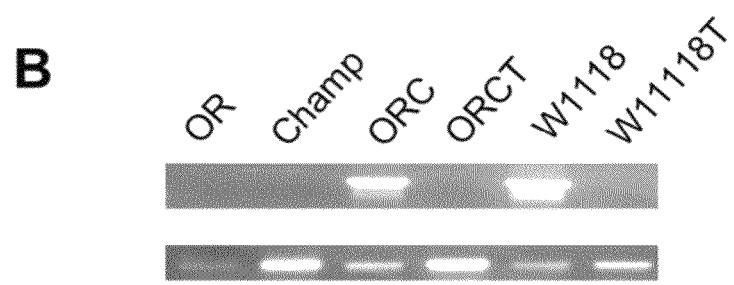
FIG. 16

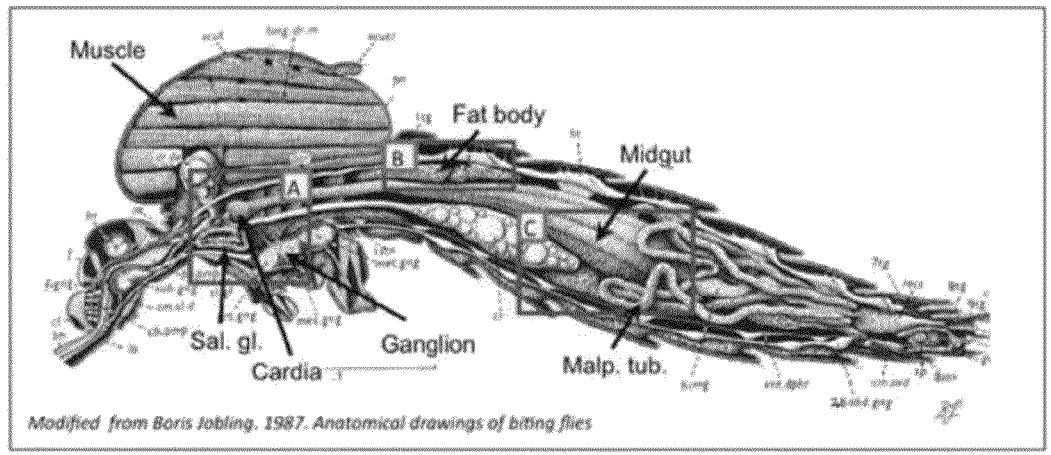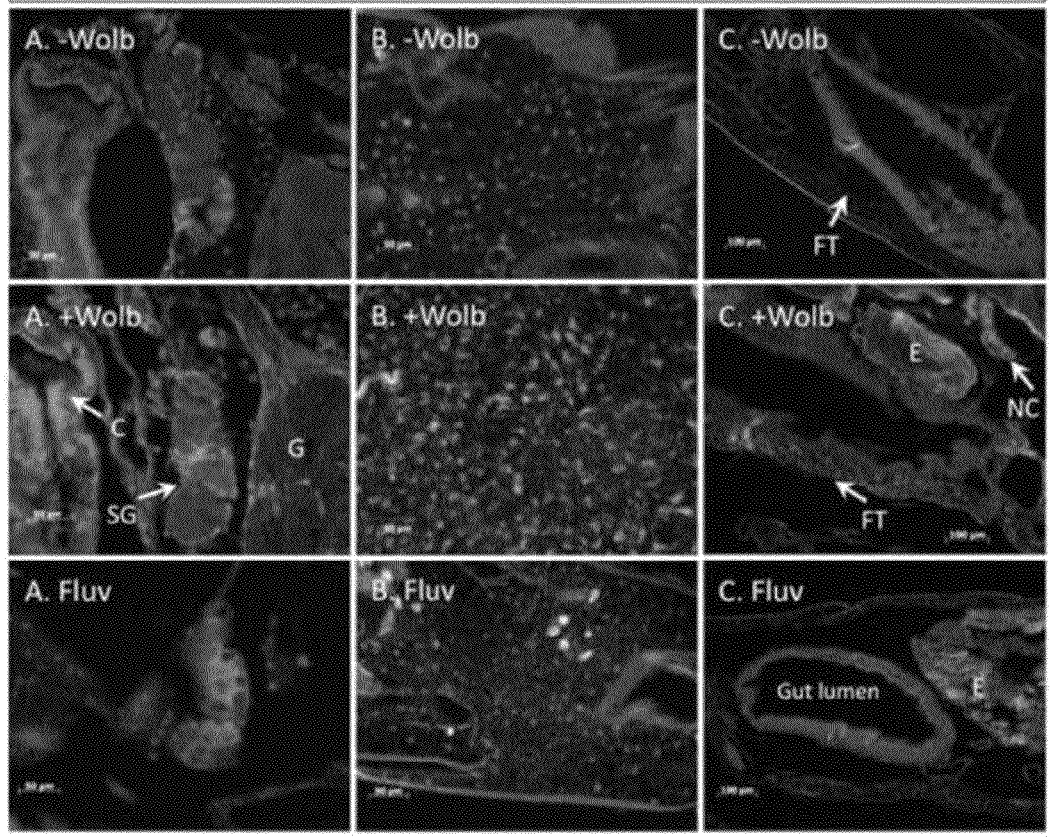
FIG. 26

A
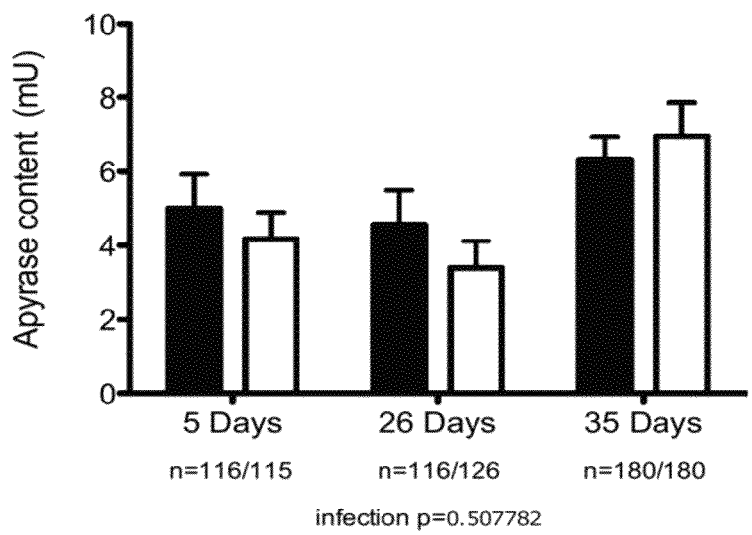
B
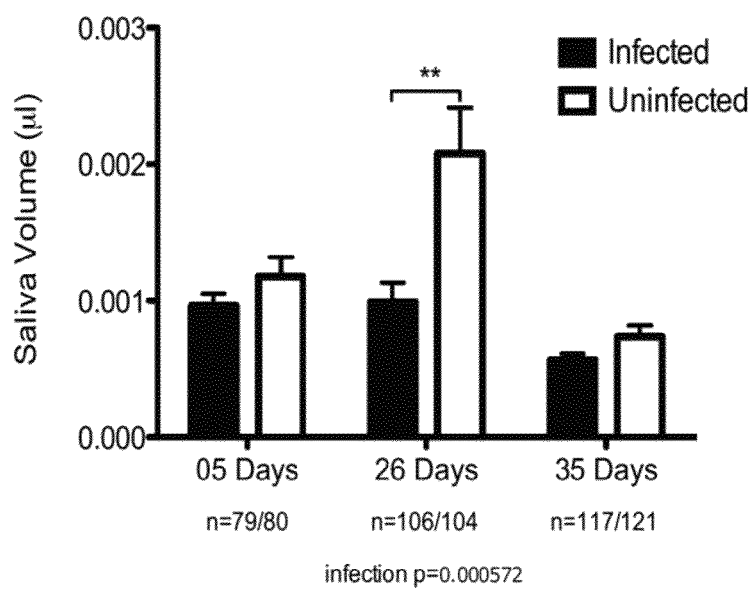
FIG. 45

```
                            MLAKISILNISNIGHYYIILTHRNIMQASYKNLQKXLTICLKKIK-
                              10        20        30        40
WD0200 in wMelPop.pro       MLAKISILNISNIGHYYIILTHRNIMQASYKNLQKDLTICLKKIK.    46
WD0200 in wMelPopMCA.pro    MLAKISILNISNIGHYYIILTHRNIMQASYKNLQKNLTICLKKIK.    46
```

FIG. 47

```
                    CCAAATATTCGTGAAGTAATCTGTTTTCCTATGAACCAGCAAGGTGAAGATGTTCTAATGGGTGCTCCTTCCAAGGTGGA
                         1690      1700      1710      1720      1730      1740      1750      1760
WD0413 wMelPop.seq     CCAAATATTCGTGAAGTAATCTGTTTTCCTATGAACCAGCAAGGTGAAGATGTTCTAATGGGTGCTCCTTCCAAGGTGGA 1760
WD0413 wMelPop-CLA.seq CCAAATATTCGTGAAGTAATCTGTTTTCCTATGAACCAGCAAGGTGAAGATGTTCTAATGGGTGCTCCTTCCAAGGTGGA 1760

GGATAAGCATTTACGTGAATTATCCTTGAAXXXXXXXXXXTGA
                         1770      1780      1790      1800
WD0413 wMelPop.seq     GGATAAGCATTTACGTGAATTATCCTTGAAGGTTATTGAATGA                                      1803
WD0413 wMelPop-CLA.seq GGATAAGCATTTACGTGAATTATCCTTGAA----------TGA                                      1793
```

FIG. 48

```
WD0413           MNCYKTHTCEELRKNDVEKEVTLSGWLYRKRDHGNLIFVDLRDFYGITQLVFNNDKFFDEISNLKLESVITVTGIVEARTEDTVNSSIS
wMelPop prot     MNCYKTHTCEELRKNDVEKEVTLSGWLYRKRDHGNLIFVDLRDFYGITQLVFNNDKFFDEISNLKLESVITVTGIVEARTEDTVNSSIS   90
wMelPop-CLA prot MNCYKTHTCEELRKNDVEKEVTLSGWLYRKRDHGNLIFVDLRDFYGITQLVFNNDKFFDEISNLKLESVITVTGIVEARTEDTVNSSIS   90
                         10        20        30        40        50        60        70        80        90

WD0413           TGEIEVIVNNLRVESEVEFHFDEETAKEERSILVSITGEQEYPENMRFKYRFLDLRREKVRNNIILRSQIIAELRKLMIERGFLEIQTPI
wMelPop prot     TGEIEVIVNNLRVESEVEFHFDEETAKEERSILVSITGEQEYPENMRFKYRFLDLRREKVRNNIILRSQIIAELRKLMIERGFLEIQTPI  180
wMelPop-CLA prot TGEIEVIVNNLRVESEVEFHFDEETAKEERSILVSITGEQEYPENMRFKYRFLDLRREKVRNNIILRSQIIAELRKLMIERGFLEIQTPI  180
                        100       110       120       130       140       150       160       170       180

WD0413           LTASSPEGARDYLVPSRLNPGKFYALPQAPQIFKQLLMVSGFDKYFQIAPCFRDEDARADRSPGEFYQLDLEMSFVTQEDIFQIIESTLY
wMelPop prot     LTASSPEGARDYLVPSRLNPGKFYALPQAPQIFKQLLMVSGFDKYFQIAPCFRDEDARADRSPGEFYQLDLEMSFVTQEDIFQIIESTLY  270
wMelPop-CLA prot LTASSPEGARDYLVPSRLNPGKFYALPQAPQIFKQLLMVSGFDKYFQIAPCFRDEDARADRSPGEFYQLDLEMSFVTQEDIFQIIESTLY  270
                        190       200       210       220       230       240       250       260       270

WD0413           RVFAKFSRKSVDKDFPRITYKEAMLKYGSDKPDLRNPLLISDVTEIFRDSGFNIFKSNIERGMVVRAIPAPKTAEEPRSFFDKKIEHAQK
wMelPop prot     RVFAKFSRKSVDKDFPRITYKEAMLKYGSDKPDLRNPLLISDVTEIFRDSGFNIFKSNIERGMVVRAIPAPKTAEEPRSFFDKKIEHAQK  360
wMelPop-CLA prot RVFAKFSRKSVDKDFPRITYKEAMLKYGSDKPDLRNPLLISDVTEIFRDSGFNIFKSNIERGMVVRAIPAPKTAEEPRSFFDKKIEHAQK  360
                        280       290       300       310       320       330       340       350       360

WD0413           EFGAKGLGYITFDKDGTAKFLDENRLNHIREATNIEPGDSVFFASDKENEAANIAGKVRTLLGSELSLIDDNIFRFCWIIDFPYF
wMelPop prot     EFGAKGLGYITFDKDGTAKFLDENRLNHIREATNIEPGDSVFFASDKENEAANIAGKVRTLLGSELSLIDDNIFRFCWIIDFPYF      450
wMelPop-CLA prot EFGAKGLGYITFDKDGTAKFLDENRLNHIREATNIEPGDSVFFASDKENEAANIAGKVRTLLGSELSLIDDNIFRFCWIIDFPYF      450
                        370       380       390       400       410       420       430       440       450

WD0413           VYDDKSKKIDFFHNPFSMPHGGLKDLEDKNPLDILAYQYDLVCNGIELSSGATRNNKLDIMYKAFALAGYSRGEVDTRFGALVRARFGV
wMelPop prot     VYDDKSKKIDFFHNPFSMPHGGLKDLEDKNPLDILAYQYDLVCNGIELSSGATRNNKLDIMYKAFALAGYSRGEVDTRFGALVRARFGV   540
wMelPop-CLA prot VYDDKSKKIDFFHNPFSMPHGGLKDLEDKNPLDILAYQYDLVCNGIELSSGATRNNKLDIMYKAFALAGYSRGEVDTRFGALVRARFGV   540
                        460       470       480       490       500       510       520       530       540

WD0413           PPHGGIAPGVDRTVMLLADEPNIREVICFPMNQQGEDVLMGAPSKVEDKHLRELSLXXXXXXXXXXXXXXXX-
wMelPop prot     PPHGGIAPGVDRTVMLLADEPNIREVICFPMNQQGEDVLMGAPSKVEDKHLRELSLKVTE.                              601
wMelPop-CLA prot PPHGGIAPGVDRTVMLLADEPNIREVICFPMNQQGEDVLMGAPSKVEDKHLRELSLNEKFYSKEHRLMIY.                    611
                        550       560       570       580       590       600       610
```

FIG. 49

```
WD0758 wMelPop.seq      GTGAAAAATGTTGTGATATATGTAAAGAAGGGCTGTCCATACTGCATAAGGGCAAAGGATTTACTAGATAAAAGGTGTGAAGTATGAA 90
WD0758 wMelPop-CLA.seq  GTGAAAAATGTTGTGATATATGTAAAGAAGAGGGCTGTCCATACTGCATGATAAGGGCAAAGGATTACTAGATAAAAGGTGTGAAGTATGAA 90
                                10        20        30        40        50        60        70        80        90

WD0758 wMelPop.seq      GAAATTGATGTGCTCAAAAACTCAGATCTATTTAACGACATAAAATCAAAGTATAACGTTAGAACAGTTCACAGATTTTATCAACGAT
WD0758 wMelPop-CLA.seq  GAAATTGATGTGCTCAAAAACTCAGATCTATTTAACGACATAAAATCAAAGTATAACGTTAGAACAGTTCACAGATTTTATCAACGAT 180
                               100       110       120       130       140       150       160       170       180

WD0758 wMelPop.seq      AAGCACATTGGGGG--TGTGACAAATTGACGATCTTGAAAAAGAAGGAAAGTTGGATGATGATATGCTAAATAATAATGACAATCACACTGA 269
WD0758 wMelPop-CLA.seq  AAGCACATTGGGGGGTGTGACAAATTGACGATCTTGAAAAAGAAGGAAAGTTGGATGATGATATGCTAAATAATAATGACAATCACACTGA 270
                               190       200       210       220       230       240       250       260       270

WD0758 wMelPop.seq      TGTCACAACCTACACAAACAGCAATGATGATGAATGTGGAGAGTGTATACCACATGATGATTTTATGTAA 339
WD0758 wMelPop-CLA.seq  TGTCACAACCTACACAAACAGCAATGATGATGAATGTGGAGAGTGTATACCACATGATGATTTTATGTAA 340
                               280       290       300       310       320       330       340
```

```
WD0758 wMelPop prot      VKNVVIYVKKGCPYCIRAKDLLDKKGVKYEEIDVLKNSDLFNDIKSKYNVRTVPQIFINDKHIGGXXXXXXXXXXXXXXXXXXXXXXX 90
WD0758 wMelPop-CLA prot  VKNVVIYVKKGCPYCIRAKDLLDKKGVKYEEIDVLKNSDLFNDIKSKYNVRTVPQIFINDKCDKLMDLEKEGKLDDMLNNNDNHTD 67
                                10        20        30        40        50        60        70        80        90

WD0758 wMelPop prot      XXXXXXXXXXXXXXXXXXXXXX- VTTYTNSNDECGECVIPHDDFM. 113
WD0758 wMelPop-CLA prot  VTTYTNSNDECGECVIPHDDFM. 67
                               100       110
```

FIG. 52

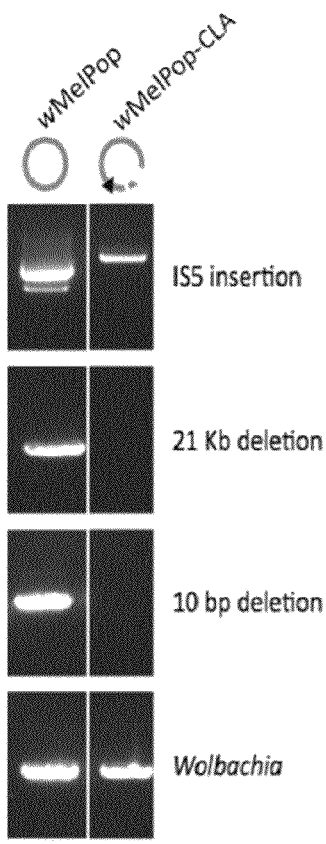

IS5 insertion: The insertion of a 918bp IS5 element between gene *WD0765* and *WD0766* can be tested by PCR using a forward primer in gene *WD0765* and a reverse primer in *WD0766*. The PCR product obtained is 918bp bigger in wMelPop-CLA than in wMelPop.

21Kb deletion: The amplification of single copy genes present in the 21kb deletion is positive only in wMelPop, but not in wMelPop-CLA.

10bp deletion: By using a primer whose 3' end matches the 10bp missing in wMelPop-CLA, only the sequence which does not contain the deletion (wMelPop) can be PCR-amplified.

Control: Common control genes can be PCR-amplified for both wMelPop and wMelPop-CLA strains.

FIG. 53

SEQUENCE LISTING

<160> NUMBER OF SEQ ID NOS: 61

<210> SEQ ID NO 1
<211> LENGTH: 19
<212> TYPE: DNA
<213> ORGANISM: Artificial Sequence
<220> FEATURE:
<223> OTHER INFORMATION: IS5-FWD1 Primer

<400> SEQUENCE: 1
gtatccaaca gatctaagc                                              19

<210> SEQ ID NO 2
<211> LENGTH: 20
<212> TYPE: DNA
<213> ORGANISM: Artificial Sequence
<220> FEATURE:
<223> OTHER INFORMATION: IS5-REV1 Primer

<400> SEQUENCE: 2
ataaccctac tcatagctag                                             20

<210> SEQ ID NO 3
<211> LENGTH: 25
<212> TYPE: DNA
<213> ORGANISM: Artificial Sequence
<220> FEATURE:
<223> OTHER INFORMATION: WD0550-FWD Primer

<400> SEQUENCE: 3
caggagttgc tgtgggtata ttagc                                       25

<210> SEQ ID NO 4
<211> LENGTH: 23
<212> TYPE: DNA
<213> ORGANISM: Artificial Sequence
<220> FEATURE:
<223> OTHER INFORMATION: WD0550-REV Primer

<400> SEQUENCE: 4
tgcaggtaat gcagtagcgt aaa                                         23

<210> SEQ ID NO 5
<211> LENGTH: 20
<212> TYPE: DNA
<213> ORGANISM: Artificial Sequence
<220> FEATURE:
<223> OTHER INFORMATION: Act88F-FWD Primer

<400> SEQUENCE: 5
atcgagcacg gcatcatcac                                             20

<210> SEQ ID NO 6
<211> LENGTH: 18
<212> TYPE: DNA
<213> ORGANISM: Artificial Sequence
<220> FEATURE:
<223> OTHER INFORMATION: Act88F-REV Primer

<400> SEQUENCE: 6
cacgcgcagc tcgttgta                                               18

<210> SEQ ID NO 7
<211> LENGTH: 20
<212> TYPE: DNA
<213> ORGANISM: Artificial Sequence

```
<220> FEATURE:
<223> OTHER INFORMATION: RpS17-FWD Primer

<400> SEQUENCE: 7
cactcccagg tccgtggtat                                               20

<210> SEQ ID NO 8
<211> LENGTH: 20
<212> TYPE: DNA
<213> ORGANISM: Artificial Sequence
<220> FEATURE:
<223> OTHER INFORMATION: RpS17-REV Primer

<400> SEQUENCE: 8
ggacacttcc ggcacgtagt                                               20

<210> SEQ ID NO 9
<211> LENGTH: 19
<212> TYPE: DNA
<213> ORGANISM: Artificial Sequence
<220> FEATURE:
<223> OTHER INFORMATION: DCV-rt-fw1 Primer

<400> SEQUENCE: 9
aggctgtgtt tgcgcgaag                                                19

<210> SEQ ID NO 10
<211> LENGTH: 21
<212> TYPE: DNA
<213> ORGANISM: Artificial Sequence
<220> FEATURE:
<223> OTHER INFORMATION: DCV-rt-rv1 Primer

<400> SEQUENCE: 10
aatggcaagc gcacacaatt a                                             21

<210> SEQ ID NO 11
<211> LENGTH: 23
<212> TYPE: DNA
<213> ORGANISM: Artificial Sequence
<220> FEATURE:
<223> OTHER INFORMATION: wspFQALL Primer

<400> SEQUENCE: 11
gcatttggtt ayaaaatgga cga                                           23

<210> SEQ ID NO 12
<211> LENGTH: 23
<212> TYPE: DNA
<213> ORGANISM: Artificial Sequence
<220> FEATURE:
<223> OTHER INFORMATION: wspRQALL Primer

<400> SEQUENCE: 12
ggagtgatag gcatatcttc aat                                           23

<210> SEQ ID NO 13
<211> LENGTH: 20
<212> TYPE: DNA
<213> ORGANISM: Artificial Sequence
<220> FEATURE:
<223> OTHER INFORMATION: Dmel.rps17F Primer

<400> SEQUENCE: 13
cactcccagg tgcgtggtat                                               20
```

<210> SEQ ID NO 14
<211> LENGTH: 20
<212> TYPE: DNA
<213> ORGANISM: Artificial Sequence
<220> FEATURE:
<223> OTHER INFORMATION: Dmel.rps17R Primer

<400> SEQUENCE: 14
ggagacggcc gggacgtagt                                           20

<210> SEQ ID NO 15
<211> LENGTH: 23
<212> TYPE: DNA
<213> ORGANISM: Artificial Sequence
<220> FEATURE:
<223> OTHER INFORMATION: W2 16S rRNA probe

<400> SEQUENCE: 15
cttctgtgag taccgtcatt atc                                       23

<210> SEQ ID NO 16
<211> LENGTH: 23
<212> TYPE: DNA
<213> ORGANISM: Artificial Sequence
<220> FEATURE:
<223> OTHER INFORMATION: W3 16S rRNA probe

<400> SEQUENCE: 16
aaccgaccct atcccttcga ata                                       23

<210> SEQ ID NO 17
<211> LENGTH: 23
<212> TYPE: DNA
<213> ORGANISM: Artificial Sequence
<220> FEATURE:
<223> OTHER INFORMATION: RpS17 Probe

<400> SEQUENCE: 17
caggaggagg aacgtgagcg cag                                       23

<210> SEQ ID NO 18
<211> LENGTH: 20
<212> TYPE: DNA
<213> ORGANISM: Artificial Sequence
<220> FEATURE:
<223> OTHER INFORMATION: ApyF Primer

<400> SEQUENCE: 18
tttcgacgga agagctgaat                                           20

<210> SEQ ID NO 19
<211> LENGTH: 20
<212> TYPE: DNA
<213> ORGANISM: Artificial Sequence
<220> FEATURE:
<223> OTHER INFORMATION: ApyR Primer

<400> SEQUENCE: 19
tccgttggta tcctcgtttc                                           20

<210> SEQ ID NO 20
<211> LENGTH: 24
<212> TYPE: DNA
<213> ORGANISM: Artificial Sequence
<220> FEATURE:
<223> OTHER INFORMATION: IS5-F Primer

```
<400> SEQUENCE: 20
ctgaaatttt agtacggggt aaag                                              24

<210> SEQ ID NO 21
<211> LENGTH: 21
<212> TYPE: DNA
<213> ORGANISM: Artificial Sequence
<220> FEATURE:
<223> OTHER INFORMATION: IS5-R Primer

<400> SEQUENCE: 21
caagcatatt ccctctttaa c                                                 21

<210> SEQ ID NO 22
<211> LENGTH: 21
<212> TYPE: DNA
<213> ORGANISM: Artificial Sequence
<220> FEATURE:
<223> OTHER INFORMATION: SPZ5-FW Primer

<400> SEQUENCE: 22
cggattctcg ccaacgaaga a                                                 21

<210> SEQ ID NO 23
<211> LENGTH: 23
<212> TYPE: DNA
<213> ORGANISM: Artificial Sequence
<220> FEATURE:
<223> OTHER INFORMATION: SPZ5-RV Primer

<400> SEQUENCE: 23
tctgttggta atgctgctgc tgc                                               23

<210> SEQ ID NO 24
<211> LENGTH: 22
<212> TYPE: DNA
<213> ORGANISM: Artificial Sequence
<220> FEATURE:
<223> OTHER INFORMATION: REL1-FW Primer

<400> SEQUENCE: 24
tggtggtggt gtcctgcgta ac                                                22

<210> SEQ ID NO 25
<211> LENGTH: 21
<212> TYPE: DNA
<213> ORGANISM: Artificial Sequence
<220> FEATURE:
<223> OTHER INFORMATION: REL1-RV Primer

<400> SEQUENCE: 25
ctgcctggcg tgaccgtatc c                                                 21

<210> SEQ ID NO 26
<211> LENGTH: 22
<212> TYPE: DNA
<213> ORGANISM: Artificial Sequence
<220> FEATURE:
<223> OTHER INFORMATION: IMD-FW Primer

<400> SEQUENCE: 26
aacagacgca gcaatcattc cg                                                22

<210> SEQ ID NO 27
```

```
<211> LENGTH: 27
<212> TYPE: DNA
<213> ORGANISM: Artificial Sequence
<220> FEATURE:
<223> OTHER INFORMATION: IMD-RV Primer

<400> SEQUENCE: 27
ggacttagaa gttgatctgg tgcagtg                                27

<210> SEQ ID NO 28
<211> LENGTH: 22
<212> TYPE: DNA
<213> ORGANISM: Artificial Sequence
<220> FEATURE:
<223> OTHER INFORMATION: REL2-FW Primer

<400> SEQUENCE: 28
gctcagtgct accgtgggaa ac                                    22

<210> SEQ ID NO 29
<211> LENGTH: 22
<212> TYPE: DNA
<213> ORGANISM: Artificial Sequence
<220> FEATURE:
<223> OTHER INFORMATION: REL2-RV Primer

<400> SEQUENCE: 29
cgggttcgct ctggcatttg tc                                    22

<210> SEQ ID NO 30
<211> LENGTH: 26
<212> TYPE: DNA
<213> ORGANISM: Artificial Sequence
<220> FEATURE:
<223> OTHER INFORMATION: DOME-FW Primer

<400> SEQUENCE: 30
aagatgttcg taacgactcg gtcatt                                26

<210> SEQ ID NO 31
<211> LENGTH: 29
<212> TYPE: DNA
<213> ORGANISM: Artificial Sequence
<220> FEATURE:
<223> OTHER INFORMATION: DOME-RV Primer

<400> SEQUENCE: 31
ggtgagattg tacgtaacat gatcggtat                             29

<210> SEQ ID NO 32
<211> LENGTH: 26
<212> TYPE: DNA
<213> ORGANISM: Artificial Sequence
<220> FEATURE:
<223> OTHER INFORMATION: SOCS36E-FW Primer

<400> SEQUENCE: 32
cgacaacgta ggaagaataa gccatt                                26

<210> SEQ ID NO 33
<211> LENGTH: 24
<212> TYPE: DNA
<213> ORGANISM: Artificial Sequence
<220> FEATURE:
<223> OTHER INFORMATION: SOCS36E-RV Primer

<400> SEQUENCE: 33
```
agctggtaat cttctgcaaa tccg                                          24

<210> SEQ ID NO 34
<211> LENGTH: 24
<212> TYPE: DNA
<213> ORGANISM: Artificial Sequence
<220> FEATURE:
<223> OTHER INFORMATION: CECG-FW Primer

<400> SEQUENCE: 34
tcacaaagtt atttctcctg atcg                                          24

<210> SEQ ID NO 35
<211> LENGTH: 20
<212> TYPE: DNA
<213> ORGANISM: Artificial Sequence
<220> FEATURE:
<223> OTHER INFORMATION: CECG-RV Primer

<400> SEQUENCE: 35
gctttagccc cagctacaac                                               20

<210> SEQ ID NO 36
<211> LENGTH: 21
<212> TYPE: DNA
<213> ORGANISM: Artificial Sequence
<220> FEATURE:
<223> OTHER INFORMATION: DEFC-FW Primer

<400> SEQUENCE: 36
ttgtttgctt cgttgctctt t                                             21

<210> SEQ ID NO 37
<211> LENGTH: 21
<212> TYPE: DNA
<213> ORGANISM: Artificial Sequence
<220> FEATURE:
<223> OTHER INFORMATION: DEFC-RV Primer

<400> SEQUENCE: 37
atctcctaca ccgaacccac t                                             21

<210> SEQ ID NO 38
<211> LENGTH: 25
<212> TYPE: DNA
<213> ORGANISM: Artificial Sequence
<220> FEATURE:
<223> OTHER INFORMATION: TEP20-FW Primer

<400> SEQUENCE: 38
ttcagtggct ttcagcaatt ctgtc                                         25

<210> SEQ ID NO 39
<211> LENGTH: 23
<212> TYPE: DNA
<213> ORGANISM: Artificial Sequence
<220> FEATURE:
<223> OTHER INFORMATION: TEP20-RV Primer

<400> SEQUENCE: 39
gcgatctgca ctttgaacaa gca                                           23

<210> SEQ ID NO 40
<211> LENGTH: 29
<212> TYPE: DNA

```
<213> ORGANISM: Artificial Sequence
<220> FEATURE:
<223> OTHER INFORMATION: CTL-FW Primer

<400> SEQUENCE: 40
gcagtgtatg aattcgttcc aatcaacta                              29

<210> SEQ ID NO 41
<211> LENGTH: 24
<212> TYPE: DNA
<213> ORGANISM: Artificial Sequence
<220> FEATURE:
<223> OTHER INFORMATION: CTL-RV Primer

<400> SEQUENCE: 41
tccaggcttc caagaacgtt aggt                                   24

<210> SEQ ID NO 42
<211> LENGTH: 27
<212> TYPE: DNA
<213> ORGANISM: Artificial Sequence
<220> FEATURE:
<223> OTHER INFORMATION: FREP18-FW Primer

<400> SEQUENCE: 42
ttctggtgtg tctggtgcta ttcaaca                                27

<210> SEQ ID NO 43
<211> LENGTH: 26
<212> TYPE: DNA
<213> ORGANISM: Artificial Sequence
<220> FEATURE:
<223> OTHER INFORMATION: FREP18-RV Primer

<400> SEQUENCE: 43
gcttccacga acatgaggtt catagc                                 26

<210> SEQ ID NO 44
<211> LENGTH: 20
<212> TYPE: DNA
<213> ORGANISM: Artificial Sequence
<220> FEATURE:
<223> OTHER INFORMATION: RpS17-FW Primer

<400> SEQUENCE: 44
cactcccagg tccgtggtat                                        20

<210> SEQ ID NO 45
<211> LENGTH: 20
<212> TYPE: DNA
<213> ORGANISM: Artificial Sequence
<220> FEATURE:
<223> OTHER INFORMATION: RpS17-RV Primer

<400> SEQUENCE: 45
ggacacttcc ggcacgtagt                                        20

<210> SEQ ID NO 46
<211> LENGTH: 23
<212> TYPE: DNA
<213> ORGANISM: Artificial Sequence
<220> FEATURE:
<223> OTHER INFORMATION: DENV-2 NS5-FW Primer

<400> SEQUENCE: 46
acaagtcgaa caacctggtc cat                                    23
```

<210> SEQ ID NO 47
<211> LENGTH: 20
<212> TYPE: DNA
<213> ORGANISM: Artificial Sequence
<220> FEATURE:
<223> OTHER INFORMATION: DENV-2 NS5-RV Primer

<400> SEQUENCE: 47
gccgcaccat tggtcttctc                                          20

<210> SEQ ID NO 48
<211> LENGTH: 23
<212> TYPE: DNA
<213> ORGANISM: Artificial Sequence
<220> FEATURE:
<223> OTHER INFORMATION: Plasm ssurRNA-FW Primer

<400> SEQUENCE: 48
gcttcttaga gggacattgt gtg                                      23

<210> SEQ ID NO 49
<211> LENGTH: 19
<212> TYPE: DNA
<213> ORGANISM: Artificial Sequence
<220> FEATURE:
<223> OTHER INFORMATION: Plasm ssurRNA Primer

<400> SEQUENCE: 49
gcgtgcagcc tagttcatc                                           19

<210> SEQ ID NO 50
<211> LENGTH: 20
<212> TYPE: DNA
<213> ORGANISM: Artificial Sequence
<220> FEATURE:
<223> OTHER INFORMATION: Actin-FW Primer

<400> SEQUENCE: 50
accgagcgtg gctactcctt                                          20

<210> SEQ ID NO 51
<211> LENGTH: 21
<212> TYPE: DNA
<213> ORGANISM: Artificial Sequence
<220> FEATURE:
<223> OTHER INFORMATION: Actin-RV Primer

<400> SEQUENCE: 51
agcgacgtag cacagcttct c                                        21

<210> SEQ ID NO 52
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 52

Met Leu Ala Lys Ile Ser Ile Leu Asn Ile Ser Asn Ile Gly His Tyr
1               5                   10                  15

Tyr Ile Ile Leu Thr His Arg Asn Ile Met Gln Ala Ser Tyr Lys Asn
            20                  25                  30

Leu Gln Lys Asp Leu Thr Ile Cys Leu Lys Lys Ile Lys
        35                  40                  45

<210> SEQ ID NO 53
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 53

```
Met Leu Ala Lys Ile Ser Ile Leu Asn Ile Ser Asn Ile Gly His Tyr
1               5                   10                  15

Tyr Ile Ile Leu Thr His Arg Asn Ile Met Gln Ala Ser Tyr Lys Asn
            20                  25                  30

Leu Gln Lys Asn Leu Thr Ile Cys Leu Lys Lys Ile Lys
        35                  40                  45
```

<210> SEQ ID NO 54
<211> LENGTH: 123
<212> TYPE: DNA
<213> ORGANISM: Artificial Sequence
<220> FEATURE:
<223> OTHER INFORMATION: Synthetic Polynucleotide

<400> SEQUENCE: 54

```
ccaaatattc gtgaagtaat ctgtttcct atgaaccagc aaggtgaaga tgttctaatg      60
ggtgctcctt ccaaggtgga ggataagcat ttacgtgaat tatccttgaa ggttattgaa    120
tga                                                                 123
```

<210> SEQ ID NO 55
<211> LENGTH: 113
<212> TYPE: DNA
<213> ORGANISM: Artificial Sequence
<220> FEATURE:
<223> OTHER INFORMATION: Synthetic Polynucleotide

<400> SEQUENCE: 55

```
ccaaatattc gtgaagtaat ctgtttcct atgaaccagc aaggtgaaga tgttctaatg      60
ggtgctcctt ccaaggtgga ggataagcat ttacgtgaat tatccttgaa tga           113
```

<210> SEQ ID NO 56
<211> LENGTH: 600
<212> TYPE: PRT
<213> ORGANISM: Artificial Sequence
<220> FEATURE:
<223> OTHER INFORMATION: Synthetic Polypeptide

<400> SEQUENCE: 56

```
Met Asn Cys Tyr Lys Thr His Thr Cys Glu Glu Leu Arg Lys Asn Asp
1               5                   10                  15

Val Glu Lys Glu Val Thr Leu Ser Gly Trp Leu Tyr Arg Lys Arg Asp
            20                  25                  30

His Gly Asn Leu Ile Phe Val Asp Leu Arg Asp Phe Tyr Gly Ile Thr
        35                  40                  45

Gln Leu Val Phe Asn Asn Asp Lys Asp Phe Phe Asp Glu Ile Ser Asn
    50                  55                  60

Leu Lys Leu Glu Ser Val Ile Thr Val Thr Gly Ile Val Glu Ala Arg
65                  70                  75                  80

Thr Glu Asp Thr Val Asn Ser Ser Ile Ser Thr Gly Glu Ile Glu Val
                85                  90                  95

Ile Val Asn Asn Leu Arg Val Glu Ser Glu Val Glu Phe His Phe Asp
```

```
                100             105             110
Glu Glu Ile Ala Lys Glu Glu Arg Ser Ile Leu Val Ser Ile Thr Gly
            115                 120                 125
Glu Gln Glu Tyr Pro Glu Asn Met Arg Phe Lys Tyr Arg Phe Leu Asp
        130                 135                 140
Leu Arg Arg Glu Lys Val Arg Asn Asn Ile Ile Leu Arg Ser Gln Ile
145                 150                 155                 160
Ile Ala Glu Leu Arg Lys Leu Met Ile Glu Arg Gly Phe Leu Glu Ile
                165                 170                 175
Gln Thr Pro Ile Leu Thr Ala Ser Ser Pro Glu Gly Ala Arg Asp Tyr
            180                 185                 190
Leu Val Pro Ser Arg Leu Asn Pro Gly Lys Phe Tyr Ala Leu Pro Gln
        195                 200                 205
Ala Pro Gln Ile Phe Lys Gln Leu Leu Met Val Ser Gly Phe Asp Lys
    210                 215                 220
Tyr Phe Gln Ile Ala Pro Cys Phe Arg Asp Glu Asp Ala Arg Ala Asp
225                 230                 235                 240
Arg Ser Pro Gly Glu Phe Tyr Gln Leu Asp Leu Glu Met Ser Phe Val
                245                 250                 255
Thr Gln Glu Asp Ile Phe Gln Ile Ile Glu Ser Thr Leu Tyr Arg Val
            260                 265                 270
Phe Ala Lys Phe Ser Arg Lys Ser Val Asp Lys Asp Phe Pro Arg Ile
        275                 280                 285
Thr Tyr Lys Glu Ala Met Leu Lys Tyr Gly Ser Asp Lys Pro Asp Leu
    290                 295                 300
Arg Asn Pro Leu Leu Ile Ser Asp Val Thr Glu Ile Phe Arg Asp Ser
305                 310                 315                 320
Gly Phe Asn Ile Phe Lys Ser Asn Ile Glu Arg Gly Met Val Val Arg
                325                 330                 335
Ala Ile Pro Ala Pro Lys Thr Ala Glu Glu Pro Arg Ser Phe Phe Asp
            340                 345                 350
Lys Lys Ile Glu His Ala Gln Lys Glu Phe Gly Ala Lys Gly Leu Gly
        355                 360                 365
Tyr Ile Thr Phe Asp Lys Asp Gly Thr Ala Lys Gly Pro Ile Ala Lys
    370                 375                 380
Phe Leu Asp Glu Asn Arg Leu Asn His Ile Arg Glu Ala Thr Asn Ile
385                 390                 395                 400
Glu Pro Gly Asp Ser Val Phe Phe Ala Ser Asp Lys Glu Asn Glu Ala
                405                 410                 415
Ala Asn Ile Ala Gly Lys Val Arg Thr Leu Leu Gly Ser Glu Leu Ser
            420                 425                 430
Leu Ile Asp Asp Asn Ile Phe Arg Phe Cys Trp Ile Ile Asp Phe Pro
        435                 440                 445
Tyr Phe Val Tyr Asp Asp Lys Ser Lys Lys Ile Asp Phe Phe His Asn
    450                 455                 460
Pro Phe Ser Met Pro His Gly Gly Leu Lys Asp Leu Glu Asp Lys Asn
465                 470                 475                 480
Pro Leu Asp Ile Leu Ala Tyr Gln Tyr Asp Leu Val Cys Asn Gly Ile
                485                 490                 495
Glu Leu Ser Ser Gly Ala Ile Arg Asn Asn Lys Leu Asp Ile Met Tyr
            500                 505                 510
Lys Ala Phe Ala Ile Ala Gly Tyr Ser Arg Gly Glu Val Asp Thr Arg
        515                 520                 525
```

```
Phe Gly Ala Leu Val Arg Ala Phe Arg Phe Gly Val Pro Pro His Gly
                525                 530                 535                 540

Gly Ile Ala Pro Gly Val Asp Arg Ile Val Met Leu Leu Ala Asp Glu
545                 550                 555                 560

Pro Asn Ile Arg Glu Val Ile Cys Phe Pro Met Asn Gln Gln Gly Glu
                565                 570                 575

Asp Val Leu Met Gly Ala Pro Ser Lys Val Glu Asp Lys His Leu Arg
                580                 585                 590

Glu Leu Ser Leu Lys Val Ile Glu
                595                 600

<210> SEQ ID NO 57
<211> LENGTH: 610
<212> TYPE: PRT
<213> ORGANISM: Artificial Sequence
<220> FEATURE:
<223> OTHER INFORMATION: Synthetic Polypeptide

<400> SEQUENCE: 57

Met Asn Cys Tyr Lys Thr His Thr Cys Glu Glu Leu Arg Lys Asn Asp
1               5                   10                  15

Val Glu Lys Glu Val Thr Leu Ser Gly Trp Leu Tyr Arg Lys Arg Asp
            20                  25                  30

His Gly Asn Leu Ile Phe Val Asp Leu Arg Asp Phe Tyr Gly Ile Thr
        35                  40                  45

Gln Leu Val Phe Asn Asn Asp Lys Asp Phe Phe Asp Glu Ile Ser Asn
    50                  55                  60

Leu Lys Leu Glu Ser Val Ile Thr Val Thr Gly Ile Val Glu Ala Arg
65                  70                  75                  80

Thr Glu Asp Thr Val Asn Ser Ser Ile Ser Thr Gly Glu Ile Glu Val
                85                  90                  95

Ile Val Asn Asn Leu Arg Val Glu Ser Glu Val Glu Phe His Phe Asp
            100                 105                 110

Glu Glu Ile Ala Lys Glu Glu Arg Ser Ile Leu Val Ser Ile Thr Gly
        115                 120                 125

Glu Gln Glu Tyr Pro Glu Asn Met Arg Phe Lys Tyr Arg Phe Leu Asp
    130                 135                 140

Leu Arg Arg Glu Lys Val Arg Asn Asn Ile Ile Leu Arg Ser Gln Ile
145                 150                 155                 160

Ile Ala Glu Leu Arg Lys Leu Met Ile Glu Arg Gly Phe Leu Glu Ile
                165                 170                 175

Gln Thr Pro Ile Leu Thr Ala Ser Ser Pro Glu Gly Ala Arg Asp Tyr
            180                 185                 190

Leu Val Pro Ser Arg Leu Asn Pro Gly Lys Phe Tyr Ala Leu Pro Gln
        195                 200                 205

Ala Pro Gln Ile Phe Lys Gln Leu Leu Met Val Ser Gly Phe Asp Lys
    210                 215                 220

Tyr Phe Gln Ile Ala Pro Cys Phe Arg Asp Glu Asp Ala Arg Ala Asp
225                 230                 235                 240

Arg Ser Pro Gly Glu Phe Tyr Gln Leu Asp Leu Glu Met Ser Phe Val
                245                 250                 255

Thr Gln Glu Asp Ile Phe Gln Ile Ile Glu Ser Thr Leu Tyr Arg Val
            260                 265                 270

Phe Ala Lys Phe Ser Arg Lys Ser Val Asp Lys Asp Phe Pro Arg Ile
        275                 280                 285
```

Thr Tyr Lys Glu Ala Met Leu Lys Tyr Gly Ser Asp Lys Pro Asp Leu
        290                 295                 300

Arg Asn Pro Leu Leu Ile Ser Asp Val Thr Glu Ile Phe Arg Asp Ser
305                 310                 315                 320

Gly Phe Asn Ile Phe Lys Ser Asn Ile Glu Arg Gly Met Val Val Arg
                325                 330                 335

Ala Ile Pro Ala Pro Lys Thr Ala Glu Glu Pro Arg Ser Phe Phe Asp
            340                 345                 350

Lys Lys Ile Glu His Ala Gln Lys Glu Phe Gly Ala Lys Gly Leu Gly
        355                 360                 365

Tyr Ile Thr Phe Asp Lys Asp Gly Thr Ala Lys Gly Pro Ile Ala Lys
    370                 375                 380

Phe Leu Asp Glu Asn Arg Leu Asn His Ile Arg Glu Ala Thr Asn Ile
385                 390                 395                 400

Glu Pro Gly Asp Ser Val Phe Phe Ala Ser Asp Lys Glu Asn Glu Ala
                405                 410                 415

Ala Asn Ile Ala Gly Lys Val Arg Thr Leu Leu Gly Ser Glu Leu Ser
            420                 425                 430

Leu Ile Asp Asp Asn Ile Phe Arg Phe Cys Trp Ile Ile Asp Phe Pro
        435                 440                 445

Tyr Phe Val Tyr Asp Asp Lys Ser Lys Lys Ile Asp Phe Phe His Asn
    450                 455                 460

Pro Phe Ser Met Pro His Gly Gly Leu Lys Asp Leu Glu Asp Lys Asn
465                 470                 475                 480

Pro Leu Asp Ile Leu Ala Tyr Gln Tyr Asp Leu Val Cys Asn Gly Ile
                485                 490                 495

Glu Leu Ser Ser Gly Ala Ile Arg Asn Asn Lys Leu Asp Ile Met Tyr
            500                 505                 510

Lys Ala Phe Ala Ile Ala Gly Tyr Ser Arg Gly Glu Val Asp Thr Arg
        515                 520                 525

Phe Gly Ala Leu Val Arg Ala Phe Arg Phe Gly Val Pro Pro His Gly
    530                 535                 540

Gly Ile Ala Pro Gly Val Asp Arg Ile Val Met Leu Leu Ala Asp Glu
545                 550                 555                 560

Pro Asn Ile Arg Glu Val Ile Cys Phe Pro Met Asn Gln Gln Gly Glu
                565                 570                 575

Asp Val Leu Met Gly Ala Pro Ser Lys Val Glu Asp Lys His Leu Arg
            580                 585                 590

Glu Leu Ser Leu Lys Val Ile Glu Tyr Ser Lys Glu His Arg Leu Met
        595                 600                 605

Ile Tyr
610

<210> SEQ ID NO 58
<211> LENGTH: 339
<212> TYPE: DNA
<213> ORGANISM: Artificial Sequence
<220> FEATURE:
<223> OTHER INFORMATION: Synthetic Polynucleotide

<400> SEQUENCE: 58
gtgaaaaatg ttgtgatata tgtaaagaag ggctgtccat actgcataag ggcaaaggat        60
ttactagata aaaaggtgt gaagtatgaa gaaattgatg tgctcaaaaa ctcagatcta       120
tttaacgaca taaatcaaa gtataacgtt agaacagttc cacagatttt tatcaacgat       180

```
aagcacattg gggggtgtga caaattgatg gatcttgaaa agaaggaaa gttggatgat      240 atgctaaata ataatgacaa tcacactgat gtcacaacct acacaaacag caatgatgaa      300
tgtggagagt gtgttatacc acatgatgat tttatgtaa                            339
```

<210> SEQ ID NO 59
<211> LENGTH: 340
<212> TYPE: DNA
<213> ORGANISM: Artificial Sequence
<220> FEATURE:
<223> OTHER INFORMATION: Synthetic Polynucleotide

<400> SEQUENCE: 59

```
gtgaaaaatg ttgtgatata tgtaaagaag ggctgtccat actgcataag ggcaaaggat      60
ttactagata aaaaggtgt gaagtatgaa gaaattgatg tgctcaaaaa ctcagatcta      120
tttaacgaca taaatcaaa gtataacgtt agaacagttc cacagatttt tatcaacgat      180
aagcacattg gggggtgtg acaaattgat ggatcttgaa aaagaaggaa agttggatga      240
tatgctaaat aataatgaca atcacactga tgtcacaacc tacacaaaca gcaatgatga      300
atgtggagag tgtgttatac cacatgatga ttttatgtaa                           340
```

<210> SEQ ID NO 60
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 60

Val Lys Asn Val Val Ile Tyr Val Lys Lys Gly Cys Pro Tyr Cys Ile
1               5                   10                  15

Arg Ala Lys Asp Leu Leu Asp Lys Lys Gly Val Lys Tyr Glu Glu Ile
                20                  25                  30

Asp Val Leu Lys Asn Ser Asp Leu Phe Asn Asp Ile Lys Ser Lys Tyr
            35                  40                  45

Asn Val Arg Thr Val Pro Gln Ile Phe Ile Asn Asp Lys His Ile Gly
        50                  55                  60

Gly Cys Asp Lys Leu Met Asp Leu Glu Lys Glu Gly Lys Leu Asp Asp
65                  70                  75                  80

Met Leu Asn Asn Asn Asp Asn His Thr Asp Val Thr Thr Tyr Thr Asn
                85                  90                  95

Ser Asn Asp Glu Cys Gly Glu Cys Val Ile Pro His Asp Asp Phe Met
                100                 105                 110

<210> SEQ ID NO 61
<211> LENGTH: 66
<212> TYPE: PRT
<213> ORGANISM: Artificial Sequence
<220> FEATURE:
<223> OTHER INFORMATION: Synthetic Polypeptide

<400> SEQUENCE: 61

Val Lys Asn Val Val Ile Tyr Val Lys Lys Gly Cys Pro Tyr Cys Ile
1               5                   10                  15

Arg Ala Lys Asp Leu Leu Asp Lys Lys Gly Val Lys Tyr Glu Glu Ile
                20                  25                  30

```
Asp Val Leu Lys Asn Ser Asp Leu Phe Asn Asp Ile Lys Ser Lys Tyr
        35                  40                  45

Asn Val Arg Thr Val Pro Gln Ile Phe Ile Asn Asp Lys His Ile Gly
        50                  55                  60

Gly Val
65
```

MODIFIED ARTHROPOD AND METHOD OF USE

CROSS-REFERENCE TO RELATED APPLICATIONS

This patent application is a continuation of copending U.S. patent application Ser. No. 12/817,933, filed Jun. 17, 2010 which claims the benefit of U.S. Provisional Patent Application No. 61/187,805, filed Jun. 17, 2009, and Australian Patent Application No. 2009222557, filed Oct. 2, 2009, all of which are incorporated by reference in their entireties herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 24,988 Byte ASCII (Text) file named "Sequence_Listing," created on Jun. 14, 2014.

FIELD OF THE INVENTION

This invention relates to arthropods and arthropod-transmitted diseases. More particularly, this invention relates to a modified arthropod, an arthropod-modifying bacterium, and use thereof as an agent for control of diseases transmitted by arthropods, particularly mosquitoes.

BACKGROUND OF THE INVENTION

Arthropods are a source of, or transmit, many diseases and conditions in humans and other animals. Some arthropods may simply cause localized irritation of the skin without transmission of disease, such as occurs with mites and ticks, or by transmission of disease-causing pathogens such as arboviruses, protozoa, bacteria and nematodes. These disease-causing pathogens are responsible for a variety of different diseases of humans and other animals including malaria, Dengue fever, Eastern Equine encephalitis, Western Equine encephalitis, Venezuelan equine encephalitis, Japanese encephalitis, Murray Valley encephalitis, West Nile fever, Yellow fever, LaCrosse encephalitis Asian spotted fever, Q fever, Lymphatic filariasis (Elephantiasis), Chikungunya fever, Ross river fever and Chagas disease.

Most pathogens that are transmitted by mosquitoes share a common property; they have to undergo a significant period of development in their insect vector before they can be transmitted to a new host. After a female mosquito ingests an infectious blood-meal, parasites or arboviruses, such as dengue, penetrate the mosquito's midgut and replicate in various tissues before infecting the salivary glands, where they are transmitted to a new host during subsequent blood-feeding. This time period from pathogen ingestion to potential infectivity is termed the extrinsic incubation period (EIP), and lasts approximately two weeks for both dengue (Siler et al., 1926; Watts et al., 1987) and malaria (Gilles et al., 2002). A female mosquito must survive longer than its initial non-feeding period (usually less than 2 days) plus the EIP to successfully contribute to pathogen transmission. Mosquito survival is therefore considered a critical component of a vector population's capacity for pathogen transmission (Dye, 1992). Interventions that aim to reduce the daily survivorship of adult mosquitoes, such as the spraying of residual insecticides in houses and insecticide-treated bednets for malaria control, yield large reductions in pathogen transmission rates (Masabo et al., 2004; Schellenberg et al., 2001) because of the sensitive relationship between mosquito survival and vectorial capacity (Garrett-Jones, 1964; MacDonald, 1957).

The control of diseases such as dengue primarily targets *Aedes aegypti*, a domesticated mosquito that prefers to live in and around human habitation (Gubler et al., 1997). With few exceptions, dengue management strategies have been complicated by the inability to completely eradicate *A. aegypti* from urban settings, and the ineffective application of long lasting vector control programs (Morrison et al., 2008). This has led to a worldwide resurgence of dengue, and highlighted the urgent need for novel and sustainable disease control strategies.

A strain of the obligate intracellular bacterium *Wolbachia pipientis*, wMelPop, has been described that reduces adult lifespan of its natural fruit fly host *Drosophila melanogaster* (Min and Benzer, 1997). *Wolbachia* are maternally-inherited bacteria that use mechanisms such as cytoplasmic incompatibility (CI), a type of embryonic lethality that results from crosses between infected males with uninfected females, to rapidly spread into insect populations (Hoffmann and Turelli, 1997).

However, life-shortening *Wolbachia* strains do not occur in mosquitoes naturally and experimental transfer of *Wolbachia* between host species (transinfection) has lacked success (Van Meer and Stouthamer, 1999). In some cases, transferred strains can be stable and maternally inherited, primarily when *Wolbachia* is transferred within or between closely related species in a family or genus (Boyle et al., 1993; Xi et al., 2005; Zabalou et al., 2004). In other cases, the new infection appears poorly adapted to its new host, showing fluctuating infection densities and variable degrees of transovarial transmission. The result is often loss of infection within a few host generations. *Wolbachia* infections tend to be more susceptible to loss when they have been transferred between phylogenetically distant hosts (Kang et al., 2003; Riegler et al., 2004). Similarly, those species that do not naturally harbour *Wolbachia* have proven refractory to transinfection (Curtis and Sinkins, 1998; Rigaud et al., 2001).

SUMMARY OF THE INVENTION

Most pathogens require a relatively long incubation period in their arthropod host before they can be transmitted to a new host. Thus, it has been proposed that a life-shortening *Wolbachia* bacterium may be used to reduce disease transmission by arthropod hosts that do not naturally harbour *Wolbachia*.

However, despite significant efforts, researchers have been unable to achieve colonization of *Wolbachia* in distantly related arthropod species due to the inability of *Wolbachia* to quickly adapt to new intra-cellular environments. To overcome this problem, the inventors have identified a need for a modified bacterium that can be easily introduced into populations of disease-transmitting arthropod vectors and reduce transmission of pathogens such as dengue virus and malaria.

The invention therefore arises from the inventors' unexpected finding that long-term serial passage of *Wolbachia* in an arthropod cell line resulted in the production of an arthropod-adapted bacterium that can be successfully transferred into, and maintained in, an arthropod and populations thereof. Furthermore, the inventors surprisingly discovered that arthropods harbouring this arthropod-adapted bacterium have a shorter lifespan, a reduced fecundity, altered feeding behaviour, and/or are less susceptible to pathogens, including viruses, fungi, worms, protozoans, and bacteria, than their wild-type counterparts.

In a first aspect, the invention provides an isolated arthropod-adapted bacterium capable of modifying one or more biological properties of an arthropod host, wherein said arthropod-adapted bacterium does not normally colonize, inhabit, reside in, or infect said arthropod host.

In a preferred embodiment, said arthropod-adapted bacterium is of the genus *Wolbachia*.

In another preferred embodiment, said isolated arthropod-adapted bacterium is of a species of *Wolbachia pipientis*.

In one particularly preferred embodiment, said isolated arthropod-adapted bacterium is wMelPop-CLA (Accession Number V14/01108, deposited on May 12, 2014 at the National Measurement Institute, 1/153 Bertie Street, Port Melbourne, Victoria, Australia).

In a second aspect, the invention provides a method of producing an arthropod-adapted bacterium capable of modifying one or more biological properties of an arthropod host, said method including the step of culturing a bacterium with one or more arthropod cells, optionally with one or more differentiating agents, to thereby produce said arthropod-adapted bacterium, wherein said arthropod-adapted bacterium does not normally colonize, inhabit, reside in, or infect said arthropod host.

In one particular embodiment, the isolated arthropod-adapted bacterium of the first aspect or the arthropod-adapted bacterium produced according to the method of the second aspect, comprises one or more genetic modifications compared to a wild-type counterpart.

In certain particular embodiments, said one or more genetic modifications correspond to one or more nucleotide sequence deletions, insertions, substitutions or mutations.

In one preferred embodiment, said arthropod-adapted bacterium is of the genus *Wolbachia*.

In another preferred embodiment, said arthropod-adapted bacterium is of a species of *Wolbachia pipientis*.

In one particularly preferred embodiment, said arthropod-adapted bacterium is wMelPop-CLA.

Preferably, said arthropod-adapted bacterium is cultured outside its native host for at least 6 months.

More preferably, said arthropod-adapted bacterium is cultured outside its native host between 1.5 to 5 years.

Even more preferably, said arthropod-adapted bacterium is cultured outside its native host for 2 to 4 years.

In one embodiment, the isolated arthropod-adapted bacterium of the first aspect or the arthropod-adapted bacterium produced according to the method of the second aspect shortens a life-span of an arthropod.

In another embodiment, the isolated arthropod-adapted bacterium of the first aspect or the arthropod-adapted bacterium produced according to the method of the second aspect reduces a susceptibility of an arthropod to a pathogen.

In yet another embodiment, the isolated arthropod-adapted bacterium of the first aspect or the arthropod-adapted bacterium produced according to the method of the second aspect reduces a fecundity of an arthropod.

In still another embodiment, the isolated arthropod-adapted bacterium of the first aspect or the arthropod-adapted bacterium produced according to the method of the second aspect reduces a desiccation tolerance of eggs produced by the arthropod.

In still yet another embodiment, the isolated arthropod-adapted bacterium of the first aspect or the arthropod-adapted bacterium produced according to the method of the second aspect reduces the ability of the arthropod to feed from a host.

In a third aspect, the invention provides an arthropod comprising the isolated arthropod-adapted bacterium of the first aspect, or the arthropod-adapted bacterium produced according to the method of the second aspect.

Suitably, said arthropod-adapted bacterium does not normally colonize, inhabit, reside in, or infect said arthropod.

Preferably, said arthropod is selected from the group consisting of an insect, an arachnid and a crustacean.

In one embodiment, said arthropod is an insect.

In another embodiment, said arthropod is a mosquito.

In one preferred embodiment, a wild-type of said arthropod is a disease-transmitting mosquito.

In another preferred embodiment, said arthropod is a mosquito of the genus selected from the group consisting of *Culex, Aedes* and *Anopheles*.

In one particularly preferred embodiment, said arthropod is a mosquito of a species selected from the group consisting of *Aedes aegypti*, and *Anopheles gambiae*.

In a fourth aspect, the invention provides a method of producing an arthropod comprising the isolated arthropod-adapted bacterium of the first aspect, or the arthropod-adapted bacterium produced according to the method of the second aspect.

In one embodiment, the arthropod of the third aspect or the arthropod produced according to the method of the fourth aspect has a reduced life-span.

Typically, according to this embodiment, said reduced life-span is shorter than an average life-span of a wild-type of said arthropod.

In another embodiment, the arthropod of the third aspect, or the arthropod produced according to the method of the fourth aspect, has a reduced susceptibility to a pathogen.

Preferably, the arthropod of the third aspect, or the arthropod produced according to the method of the fourth aspect, has improved protection against, or resistance to, a pathogen compared to a wild-type counterpart.

Typically, according to this embodiment, said pathogen is selected from the group consisting of a virus, a fungus, a worm, a protozoan, and a bacterium.

In yet another embodiment, the arthropod of the third aspect, or the arthropod produced according to the method of the fourth aspect has a reduced fecundity.

In still another embodiment, the arthropod of the third aspect, or the arthropod produced according to the method of the fourth aspect has a reduced ability to feed from a host.

In a fifth aspect, the invention provides a method of modifying an arthropod population, said method including the step of introducing the arthropod of the third aspect, or the arthropod produced according to the method of the fourth aspect, into said arthropod population, to thereby modify one or more biological properties of said arthropod population.

In one embodiment of the fifth aspect, the invention provides a method of reducing pathogen transmission by an arthropod population, said method including the step of introducing the arthropod of the third aspect, or the arthropod produced according to the method of the fourth aspect, into said arthropod population, to thereby reduce, decrease, or mitigate pathogen transmission by said arthropod population.

In another embodiment of the fifth aspect, the invention provides a method of reducing a susceptibility to a pathogen in an arthropod population, said method including the step of introducing the arthropod of the third aspect, or the arthropod produced according to the method of the fourth aspect, into said arthropod population, to thereby reduce, decrease, or mitigate the susceptibility to said pathogen in said arthropod population.

Preferably, said pathogen is selected from the group consisting of a virus, a fungus, a worm, a protozoan, and a bacterium.

In yet another embodiment of the fifth aspect, the invention provides a method of reducing an average life-span of an arthropod population, said method including the step of introducing the arthropod of the third aspect, or the arthropod produced according to the method of the fourth aspect, into said arthropod population, to thereby reduce, lower, shorten or decrease said average life-span of said arthropod population.

In still another embodiment of the fifth aspect, the invention provides a method of reducing a fecundity of an arthropod population, said method including the step of introducing the arthropod of the third aspect, or the arthropod produced according to the method of the fourth aspect, into said arthropod population, to thereby reduce, lower, or decrease said fecundity of said arthropod population.

In still yet another embodiment of the fifth aspect, the invention provides a method of reducing an ability of an arthropod population to feed from a host, said method including the step of introducing the arthropod of the third aspect, or the arthropod produced according to the method of the fourth aspect, into said arthropod population, to thereby reduce, lower, or decrease said ability of said arthropod population to feed from a host.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 16. *Wolbachia* infection in fly lines. (A) Comparison of DCV mortality in three wild-type laboratory fly lines. DCV induced mortality is delayed in the Oregon RC (ORC) fly line as compared to Oregon R (OR) and Champetieres (Champ) flies. Data shown represents the mean of triplicates and the error bars indicate standard error. The survival curve for the ORC flies was significantly different from either OR ($p<0.001$) or Champ ($p<0.001$), whereas those of OR and Champ were not significantly different ($p=0.1$) (Kaplan-Meier analysis). (B) Detection of *Wolbachia* infection by PCR using primers specific for the *Wolbachia* surface protein (wsp) upper panel. Detection of the 12S DNA was used as a positive control for DNA template quality (bottom panel). Tetracycline treatment cured the ORC and $w^{1118}$ fly lines of *Wolbachia* infection.

FIG. 26. *Wolbachia* distribution in *Aedes* spp. mosquitoes. Fluorescence in situ hybridization of paraffin sections showing the localization of *Wolbachia* (in red) in different tissues of *A. aegypti* and in *A. fluviatilis* mosquitoes. Sections were hybridized with two *Wolbachia* specific 16S rRNA probes labelled with rhodamine. DNA is stained with DAPI (blue). A green filter is used to provide contrast. The top diagram has been adapted from (Jobling, 1987). Panels A) Anterior part of the digestive system, showing the salivary glands (SG) and the cardia (C), together with the thoracic ganglion (G) of uninfected *A. aegypti* (−Wolb), PGYP1.out (+Wolb) and *A. fluviatilis* mosquitoes. Panels B). Fat tissue showing the presence of wMelPop-CLA in PGYP1.out (+Wolb) mosquitoes but absence of the bacteria in PGYP1.out.tet (−Wolb) and *A. fluviatilis*. C) wMelPop-CLA is present in the fat tissue surrounding the gut in PGYP1.out mosquitoes (+Wolb), as well as in nurse cells (NC) and embryos (E). No wFlu *Wolbachia* was detected in fat tissue or salivary glands of *A. fluviatilis*. See also FIGS. 30-31.

Comparison of time spent by mosquitoes infected with $Wolbachia$ (black bars) or tetracycline treated counterparts (white bars) of different ages (5, 15, 26 and 35 days) after landing on a human hand until the insertion of mouthparts into the skin (N=12-40 per group). Bars depict means+S.E.M. *p<0.05; **p<0.01 by t-test.

Figure 41:
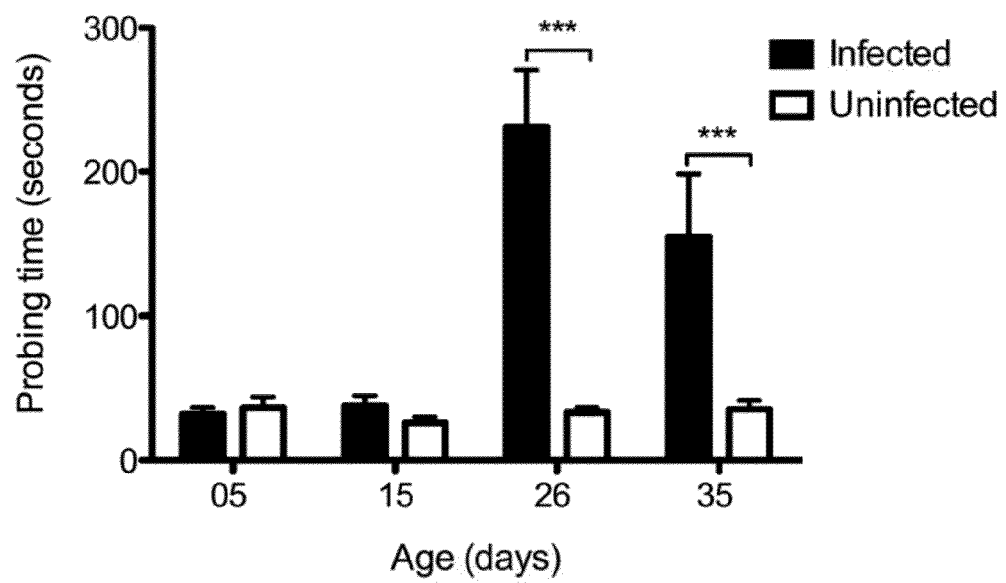

FIG. 41. Probing behaviour of $A. aegypti$ mosquitoes.

Comparison of time spent by mosquitoes infected with $Wolbachia$ (black bars) or tetracycline treated counterparts (white bars) of different ages (5, 15, 26 and 35 days) from the insertion of mouthparts into the skin of a human hand and the first sign of blood within the insect midgut. (N=12-40 per group). Bars depict means+S.E.M. ***p<0.0001 by t-test.

Figure 42:
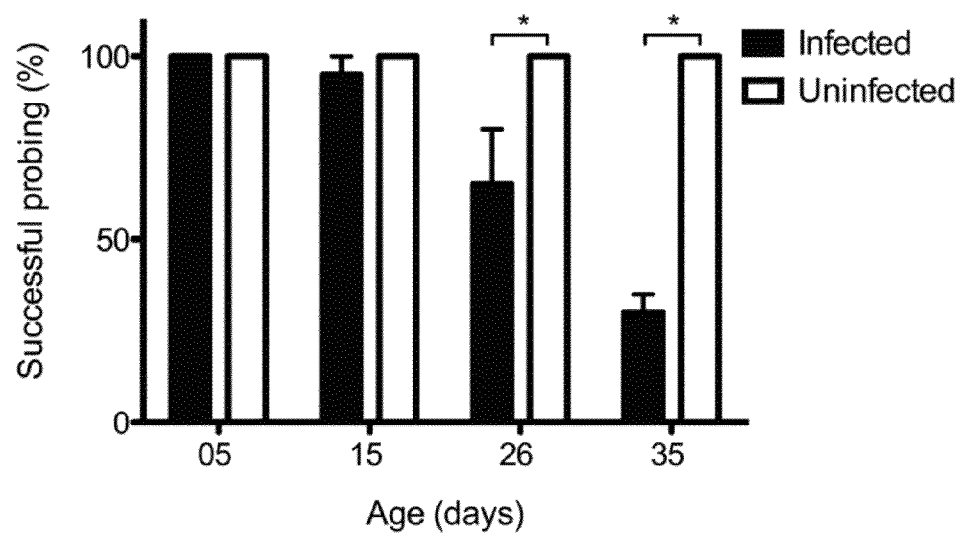

FIG. 42. Percent of $A. aegypti$ mosquitoes that obtained a blood meal.

Percentage of wMelPop-infected (black bars) and tetracycline-treated mosquitoes (white bars), that successfully imbibed blood within 10 minutes of observation, by age class. Bars depict medians+75% quartile values based on four replicates. * p<0.05 by Mann-Whitney U test.

Figure 43:
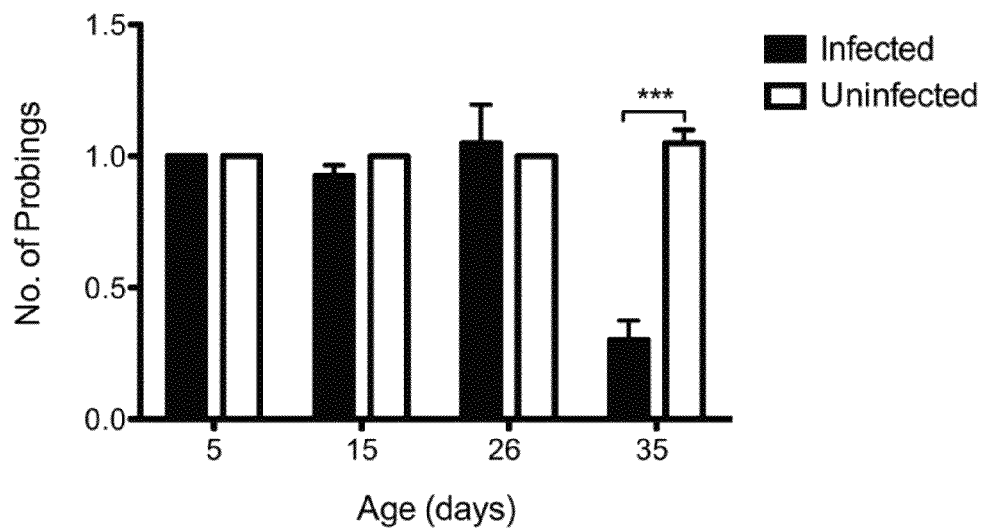

FIG. 43. Number of probings in $A. aegypti$ mosquitoes.

Comparison of number of probings of mosquitoes infected with $Wolbachia$ (black bars) or tetracycline treated counterparts (white bars) of different ages (5, 15, 26 and 35 days). (N=40 per group). Bars depict means+S.E.M. ***p<0.0001 by t-test.

Figure 44:
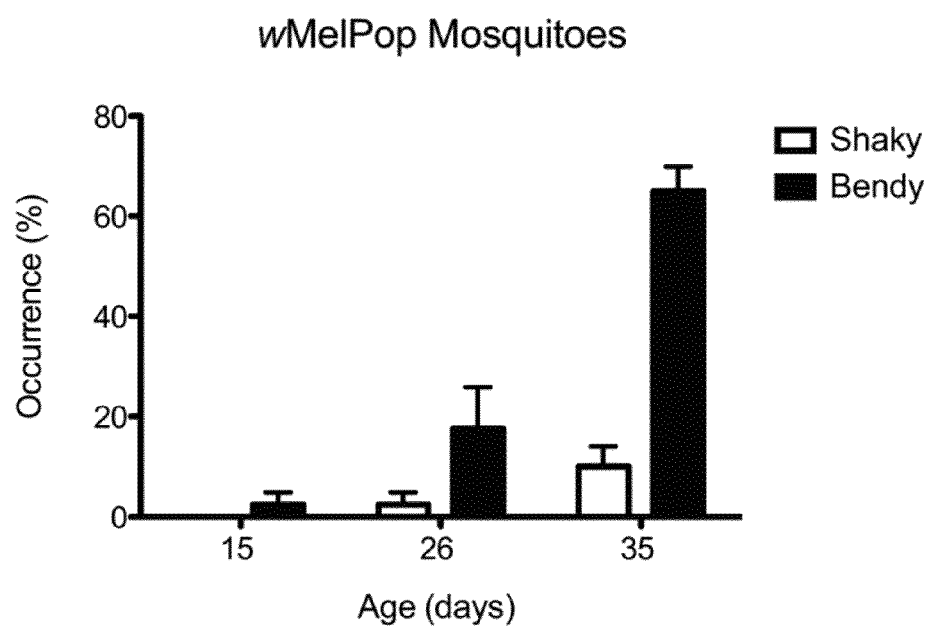

FIG. 44. Additional phenotypes observed in $Wolbachia$-infected $A. aegypti$.

Proportion of wMelPop-infected mosquitoes exhibiting abnormal pre-probing behaviour as: body jittering ("shaky") or bended proboscis ("bendy") in mosquitoes from their first occurrence at 15 days of age. Neither of these behaviours was observed in $Wolbachia$ non-infected mosquitoes.

FIG. 45. Apyrase content and saliva volume.

Comparisons of apyrase and saliva volume of mosquitoes infected with $Wolbachia$ (black bars) or tetracycline treated counterparts (white bars) of different ages (5, 26 and 35 days). A) Apyrase activity measured through the release of inorganic phosphate from ATP. B) Saliva volume measured through the sphere volume of saliva droplets. Number of replicates in each group and age are represented. Bars depict means+S.E.M. P values relate to univariate tests of significance derived from general linear models. ** indicates P<0.01 from t-tests for the specific age category.

Figure 46:
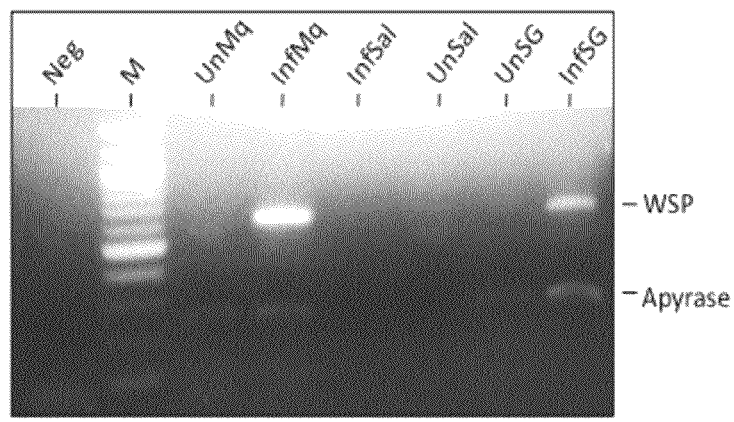

FIG. 46. $Wolbachia$ screening in mosquito saliva.

PCR analysis to detect $Wolbachia$ in mosquito saliva. Mosquito (apyrase) or $Wolbachia$ (WSP) specific primers in infected (InfMq) or uninfected mosquitoes (UnMq), saliva (InfSal or UnSal) or salivary glands (InfSG or UnSG). Specific bands were only detected in whole mosquitoes or salivary glands. Neg=negative control; M=100 bp NEB DNA ladder.

FIG. 47. Protein sequence alignment of the WD0200 proteins of wMelPop (SEQ ID NO: 52) and wMelPop-CLA (SEQ ID NO: 53), showing the mutation of one aspartic residue (D) into asparagine (N).

FIG. 48. Partial DNA sequence alignment between wMelPop (SEQ ID NO: 54) and wMelPop-CLA gene WD0413 (SEQ ID NO: 55) showing a 10 bp deletion in the 3'-end of the gene.

FIG. 49. Protein sequence alignment of wMelPop (SEQ ID NO: 56) and wMelPop-CLA WD0413 (SEQ ID NO: 57) showing the extension of the wMelPop-CLA putative protein by 10 amino acids, as a result of the creation of a frameshift.

Figure 50:
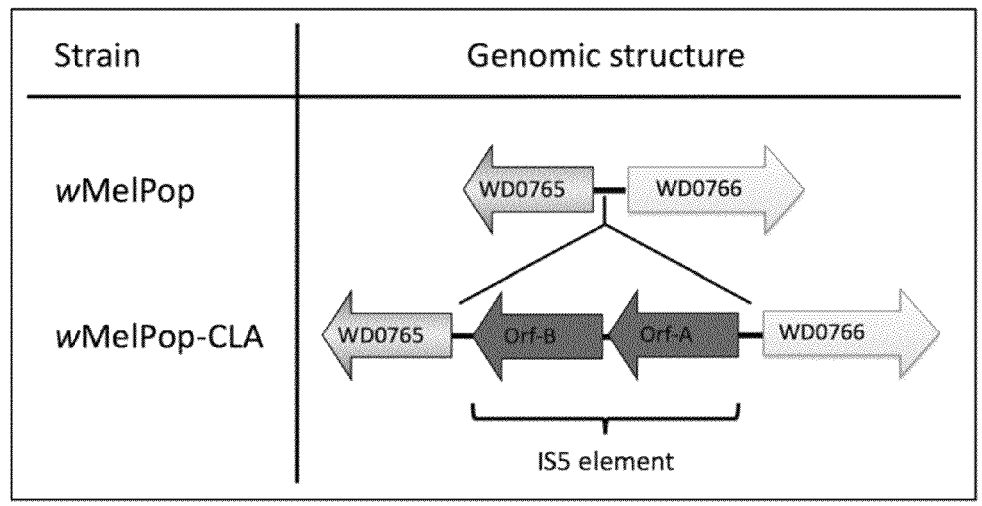

FIG. 50. Diagram showing the insertion of an IS5 element between the genes WD0765 and WD0766 in the wMelPop-CLA $Wolbachia$ strain.

Figure 51:
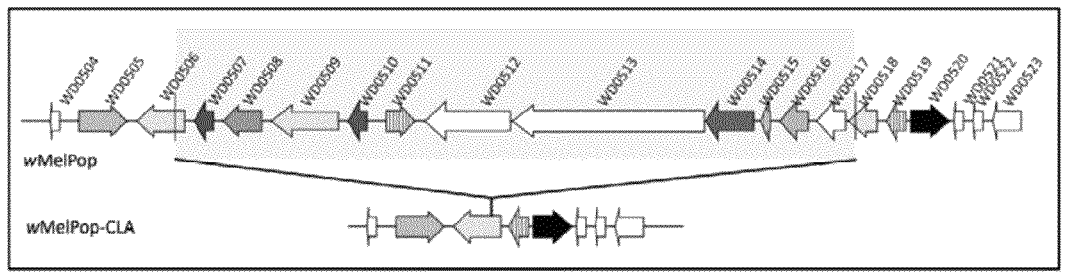

FIG. 51. Diagram showing the deletion of 13 genes in the wMelPop-CLA strain compared to the original wMelPop strain.

FIG. 52. DNA (Top) and protein (bottom) alignment of WD0758 from wMelPop (SEQ ID NO: 58 (nucleic acid) and SEQ ID NO: 60 (protein)) and wMelPop-CLA (SEQ ID NO: 59 (nucleic acid) and SEQ ID NO: 61 (protein)), showing the insertion of a G that creates a frameshift and a premature stop codon.

FIG. 53. Differential amplification of 3 out of the 5 unique features of wMelPop-CLA by PCR.

Figure 54:
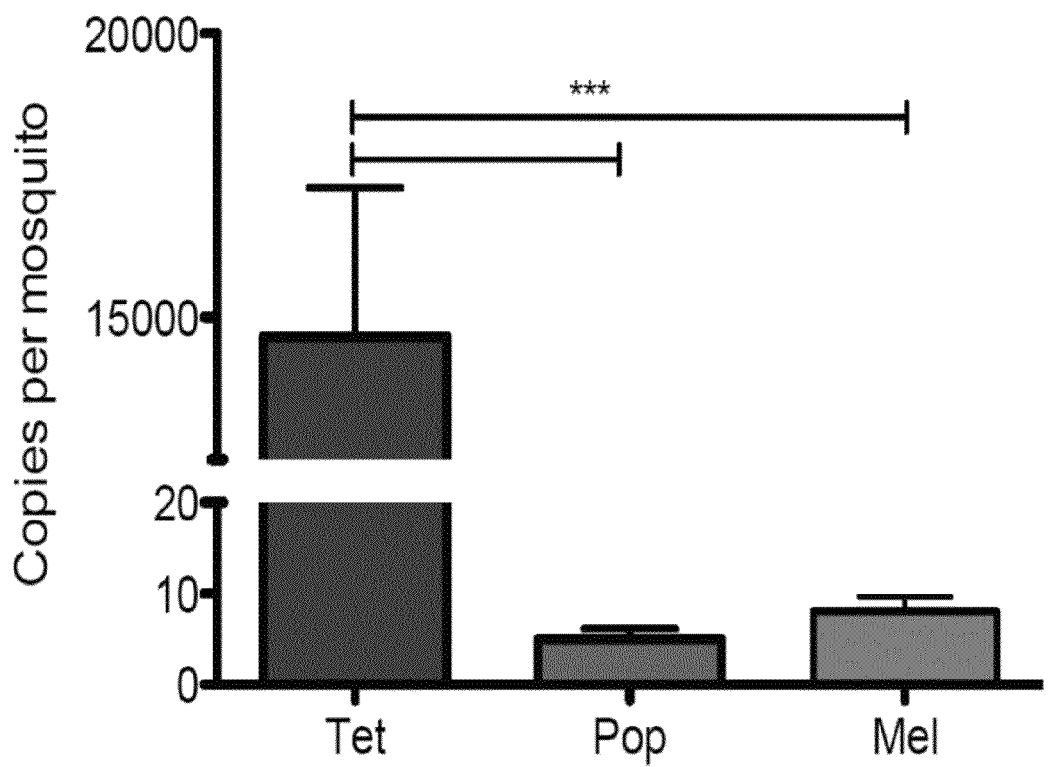

FIG. 54. Results illustrating that dengue virus interference is generated by the wMel strain in mosquitoes. The graph shows the results of oral feeding of mosquitoes with DENV-2 virus 14 days post infection (14 d.p.i.). Dengue has been measured in mosquito legs by qPCR to determine disseminated infection. Graphs show mean number of viral copies+/− standard error. Tet=control $Wolbachia$ uninfected mosquitoes, Pop=wMelPop-CLA infected mosquitoes and Mel=wMel infected mosquitoes.

DETAILED DESCRIPTION OF THE PREFERRED EMBODIMENT

The present invention has arisen from the inventors' unexpected discovery that long-term serial passage of a $Wolbachia$ bacterium in an arthropod cell line resulted in the production of an arthropod-adapted bacterium that can be successfully transferred into an arthropod which does not naturally harbour $Wolbachia$. The inventors have also surprisingly found that arthropods harbouring the arthropod-adapted bacterium, and populations thereof, have a shorter life-span, a reduced fecundity, altered feeding behaviour, and/or a lower susceptibility to pathogens such as viruses, fungi, worms (e.g. nematodes), protozoans, and bacteria.

This invention therefore provides an arthropod-adapted bacterium, and an arthropod comprising the same, for use in the reduction of arthropod-borne diseases such as, but not limited to, dengue fever, malaria and lymphatic filariasis.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state.

As used herein, the term "arthropod" refers to an invertebrate animal that is characterized by a chitinous exoskeleton and a segmented body with paired, jointed appendages (e.g. legs or feet). Accordingly, an arthropod may be an insect (e.g. a mosquito or a fly), a crustacean (e.g. a prawn, a crab, or a lobster), or an arachnid (e.g. a tick or a mite), although without limitation thereto. As also used herein, the terms "arthropod vector" or "arthropod vector population" refer to an arthropod, or a population thereof, that is capable of transmitting a pathogen from one host to another.

Arthropods preferably include insects, arachnids and crustaceans.

Insects include insects of orders such as Diptera (e.g. mosquitoes, horseflies, midges, stableflies and tsetse flies), Phthiraptera (e.g. lice), Siphonaptera (e.g. fleas) and Hemiptera (e.g. bedbugs and triatomine bugs).

An example of an arachnid is a tick or mite (e.g of the families *Argasida, Trombidiidae* and *Ixodidae*). These can simply cause localized irritation of the skin or transmit pathogens such as bacteria (e.g. *Rickettsia* and *Coxiella*) and viruses (typically Flaviviruses) which cause diseases such as Asian spotted fever, North American or Rocky Mountain spotted fever, American mountain fever or Colorado tick fever, Q fever, Russian spring-summer encephalitis and tick paralysis. Spider mites, which are members of the Acari (mite) family *Tetranychidae*, may also spread disease by transferring pathogens (e.g. fungus) between plants.

An example of a crustacean is a prawn or a crab (e.g. of the families *Peneidae* and *Coenobitidae*). Most cultured penaeid prawns (e.g. *Penaeus monodon, Marsupenaeus japonicus* and *Litopenaeus vannamei*) carry and transfer the DNA viruses of the species White Spot Syndrome Baculovirus Complex, which cause White Spot Syndrome in crustaceans such as prawns, lobsters and crabs.

In one aspect, the invention provides an isolated arthropod-adapted bacterium capable of modifying one or more biological properties of an arthropod host.

By "arthropod-adapted" bacterium is meant a bacterium (e.g. of the genus *Wolbachia*) that has been taken out of its native host environment and adapted to a new arthropod host environment, in which environment said bacterium does not naturally reside. Accordingly, a non-limiting example of an arthropod-adapted bacterium is a *Wolbachia* bacterium that has been isolated from its native host (e.g. *Drosophila melanogaster*) and adapted to a new host (e.g. *Aedes aegyptii* or *Anopheles gambiae*).

It will be appreciated that the term arthropod-adapted bacterium encompasses any bacterium that is capable of colonizing, infecting, or residing in an arthropod host within which it does not normally reside.

In a preferred embodiment, said isolated arthropod-adapted bacterium is of the genus *Wolbachia*.

*Wolbachia* includes strains such as wMel, wMelPop, wMelPop-CLA, wMelCS, wAu, wRi, wNo, wHa, wMau, and wCer2, although without limitation thereto.

In one particular embodiment, said isolated arthropod-adapted bacterium is *Wolbachia pipientis*.

In one particularly preferred embodiment, said isolated arthropod-adapted bacterium is wMelPop-CLA.

As used herein, the term "wMelPop-CLA" refers to a particularly preferred arthropod-adapted wMelPop.

In one embodiment, said isolated arthropod-adapted bacterium shortens a life-span of an arthropod.

In another embodiment, said isolated arthropod-adapted bacterium reduces a susceptibility of an arthropod to a pathogen.

As used herein, an arthropod that has a "reduced susceptibility" to a pathogen is less likely to become infected by, carry and/or transmit a pathogen than a wild-type counterpart.

As referred to herein, a pathogen may be a virus, a fungus, a protozoan, a worm or a bacterium.

Non-limiting examples of virus pathogens include arboviruses such as Alphaviruses (e.g. Chikungunya virus, Eastern Equine Encephalitis virus, Western Equine Encephalitis virus), Flaviviruses (e.g. dengue virus, West Nile virus, Yellow Fever virus), and Bunyaviruses (e.g. La Crosse virus, Rift Valley fever virus, Colorado tick fever virus).

An example of a protozoan parasite is a malaria parasite of the *Plasmodium* genus such as, but not limited to, *Plasmodium falciparum, Plasmodium vivax, Plasmodium ovale, Plasmodium malariae, Plasmodium berghei, Plasmodium gallinaceum*, and *Plasmodium knowlesi*.

Non-limiting examples of worm pathogens include nematodes, inclusive of filarial nematodes such as *Wuchereria bancrofti, Brugia malayi, Brugia pahangi, Brugia timori*, and *Dirofilaria immitis*.

A pathogen may also be a bacterium, inclusive of a Gram negative and Gram positive bacterium.

It will be appreciated that non-limiting examples of pathogenic bacteria include spirochetes (e.g. *Borrelia*), actinomycetes (e.g. *Actinomyces*), mycoplasmas, Rickettsias, Gram negative aerobic rods, Gram negative aerobic cocci, Gram negatively facultatively anaerobic rods (e.g. *Erwinia* and *Yersinia*), Gram-negative cocci, Gram negative coccobacilli, Gram positive cocci (e.g. *Staphylococcus* and *Streptococcus*), endospore-forming rods, and endospore-forming cocci.

By way of example only, pathogenic bacteria include *Yersinia pestis, Borellia* spp, *Rickettsia* spp, and *Erwinia carotovora*.

In yet another embodiment, said isolated arthropod-adapted bacterium introduces a reproductive abnormality in an arthropod host such as, but not limited to, parthenogenesis, feminization, male killing, and cytoplasmic incompatibility (CI).

Typically, according to this embodiment, said reproductive abnormality reduces a fecundity within an arthropod vector population.

As used herein, the term "fecundity" refers to the ability of an arthropod, or a population thereof, to reproduce.

In another aspect, the invention provides a method of producing an arthropod-adapted bacterium capable of modifying one or more biological properties of an arthropod host, said method including the step of culturing a bacterium with one or more arthropod cells, optionally with one or more differentiating agents, to thereby produce said arthropod-adapted bacterium.

Suitably, said arthropod-adapted bacterium does not normally colonize, inhabit, reside in, or infect said arthropod host.

In a preferred embodiment, said arthropod-adapted bacterium is of the genus *Wolbachia*.

*Wolbachia* includes strains such as wMel, wMelPop, wMelPop-CLA, wMelCS, wAu, wRi, wNo, wHa, wMau, and wCer2, although without limitation thereto.

In one particular embodiment, said isolated arthropod-adapted bacterium is *Wolbachia pipientis*.

In one particularly preferred embodiment, said arthropod-adapted *Wolbachia* bacterium is wMelPop-CLA.

Preferably, said arthropod-adapted bacterium is cultured outside its native host for at least 6 months.

More preferably, said arthropod-adapted bacterium is cultured outside its native host between 1.5 to 5 years.

Accordingly, it will be appreciated that said arthropod may be cultured outside its native host for about 2 years, 2.5 years, 3 years, 3.5 years, 4 years. 4.5 years, and up to about 5 years.

Even more preferably, said arthropod-adapted bacterium is cultured outside its native host for 2 to 4 years.

In one particular embodiment, said native host is of the genus *Drosophila*.

In another particular embodiment, said native host is of a species of *Drosophila melanogaster*.

In yet another particular embodiment, said native host is of a species of *Drosophila simulans*.

In one embodiment, said one or more arthropod cells are of an arthropod of the genus selected from the group consisting of *Aedes* and *Anopheles*.

In another embodiment, said one or more arthropod cells are of an arthropod of a species selected from the group consisting of *Aedes albopictus*, *Aedes aegypti*, and *Anopheles gambiae*.

Accordingly, a non-limiting exemplary method of producing the arthropod-adapted bacterium according to this aspect comprises the steps of (i) isolating a bacterium (e.g. wMelPop) from an arthropod host (e.g. *Drosophila melanogaster*), (ii) establishing the isolated bacterium in a first culture of one or more arthropod cells (e.g. of a species of *Aedes albopictus*); (iii) culturing the first culture for a period of time (e.g. 2-3 years); (iv) isolating the bacterium from the first culture; (v) introducing the bacterium from the first culture into a second culture of one or more arthropod cells (e.g. of a species of *Aedes aegyptii* or *Anopheles gambiae*), and (vi) culturing the second culture for a period of time (e.g. 3-12 months), to thereby produce the arthropod-adapted bacterium (e.g. wMelPop-CLA) according to this aspect.

A skilled person will appreciate that the bacterium which is to be adapted to a new arthropod host may be isolated from an arthropod during different developmental stages of their lifecycle and from different tissues such as, an embryo, a cytoplasm, or a hemolymph, although without limitation thereto.

Non-limiting methods for introducing an isolated bacterium into an uninfected arthropod host, or cells thereof, may be selected from the group consisting of a shell vial technique, and a microinjection.

In yet another embodiment, the arthropod-adapted bacterium reduces the ability of an arthropod to feed from a host.

Typically, according to this embodiment, the arthropod (e.g. a mosquito) may have a reduced ability to obtain, ingest, or otherwise acquire blood from an arthropod host (e.g. a human) compared to a corresponding wild-type arthropod.

In some embodiments, the arthropod-adapted bacterium (e.g. wMelPop-CLA) comprises one or more genetic modifications when compared to a corresponding wild-type counterpart (e.g. wMelPop).

Such genetic modifications may be selected from the group consisting of a nucleotide sequence insertion, a deletion, a single nucleotide polymorphism (SNP), a mutation, a frameshift, a chromosomal rearrangement, or a transposition, although without limitation thereto.

In some embodiments, said genetic modifications relate to the modification of one or more nucleotide sequences as set forth in Table 7.

In another aspect, the invention provides an arthropod comprising the isolated arthropod-adapted bacterium.

An arthropod comprising the isolated arthropod-adapted bacterium of the aforementioned aspects may be referred to as a "modified arthropod".

Suitably, a wild-type of said modified arthropod is an arthropod vector that carries and transfers a pathogen from one "host" to another.

A "host" may be any animal or plant upon which an arthropod feeds and/or to which an arthropod is capable of transmitting a disease-causing pathogen. Non-limiting examples of hosts are plants (e.g. flowers, vegetables, fruits, and crops), mammals such as humans, domesticated pets (e.g. dogs and cats), wild animals (e.g. monkeys, rodents and wild cats) livestock animals (e.g. sheep, pigs, cattle, and horses), avians such as poultry (e.g. chickens, turkeys and ducks) and other animals such as crustaceans (e.g. prawns and lobsters).

It will be appreciated that an arthropod vector may act as a carrier of a pathogen that is harmful to a host (e.g. a human) and not to the arthropod vector itself.

A non-limiting example of vector-borne pathogen transmission is by blood-feeding arthropods (e.g. mosquitoes). The pathogen (e.g. a dengue virus) multiplies within the arthropod vector, and the pathogen is transmitted from the arthropod vector to an animal host (e.g. a human) when the arthropod takes a blood meal. Mechanical transmission of pathogens may occur when arthropods physically carry pathogens from one place or host to another, usually on body parts.

It will also be appreciated that an arthropod vector may transmit disease within an arthropod group. A non-limiting example is the transmission of the viral pathogens that cause White Spot Syndrome in crustaceans from one arthropod (e.g. a prawn) to another.

An arthropod may also facilitate pathogen transmission between plants. A non-limiting example is the transfer of yeast pathogens to grapes by mites.

While in certain embodiments, arthropod-adapted bacteria may be useful for creating modified arthropod vectors (e.g. mosquitoes) having reduced capacity to transmit disease-causing pathogens (e.g. malaria), in other embodiments, the invention provides arthropods that have "beneficial traits" or uses which are enhanced or improved by arthropod-adapted bacteria. Non-limiting examples include insects such as honey-bees and crustaceans such as prawns, lobsters and crabs having reduced susceptibility to pathogens.

Preferably, said arthropod is selected from the group consisting of an insect, an arachnid and a crustacean.

In one particular embodiment, said arthropod is an insect.

In another particular embodiment, said arthropod is a mosquito.

In one particular embodiment, a wild-type of said arthropod is a disease-transmitting mosquito.

As used herein "mosquito" and "mosquitoes" include insects of the family *Culicidae*. Preferably, mosquitoes are of the sub-families *Anophelinae* and *Culicinae*. Even more preferably, mosquitoes are capable of transmitting disease-causing pathogens, including viruses, protozoa, worms (e.g. nematodes) and bacteria. Non-limiting examples include species of the genus *Anopheles* which transmit malaria pathogens, species of the genus *Culex*, and species of the genus *Aedes* (e.g. *Aedes aegypti*, *Aedes albopictus* and *Aedes polynesiensis*) which transmit nematode worm pathogens, arbovirus pathogens such as Alphaviruses (e.g. Eastern Equine encephalitis, Western Equine encephalitis, Venezuelan equine encephalitis), *Flavivirus* pathogens that cause diseases such as Japanese encephalitis, Murray Valley Encephalitis, West Nile fever, Yellow fever, Dengue fever, and Bunyavirus pathogens that cause diseases such as LaCrosse encephalitis, Rift Valley Fever, and Colorado tick fever, although without limitation thereto. Non-limiting examples of worm pathogens include nematodes (e.g. filarial nematodes such as *Wuchereria bancrofti, Brugia malayi, Brugia pahangi* or *Brugia timori*), which may be transmitted by mosquitoes.

Disease-causing pathogens transmitted by mosquitoes also include bacteria (e.g. *Yersinia pestis, Borellia* spp, *Rickettsia* spp, and *Erwinia carotovora*).

Non-limiting examples of pathogens that may be transmitted by *Aedes aegypti* are dengue virus, Yellow fever virus, Chikungunya virus and heartworm (*Dirofilaria immitis*).

Examples of pathogens that may be transmitted by *Aedes albopictus* include West Nile Virus, Yellow fever virus, St. Louis Encephalitis, dengue virus, and Chikungunya fever although without limitation thereto.

Pathogens frequently transmitted by the mosquito vector *Anopheles gambiae* include malaria parasites of the genus *Plasmodium* such as, but not limited to, *Plasmodium falciparum, Plasmodium vivax, Plasmodium ovale, Plasmodium malariae, Plasmodium berghei, Plasmodium gallinaceum*, and *Plasmodium knowlesi*.

In one particularly preferred embodiment, said arthropod is a mosquito of the genus selected from the group consisting of *Culex, Aedes* and *Anopheles*.

In another particularly preferred embodiment, said arthropod is a mosquito of a species selected from the group consisting of *Aedes aegypti, Aedes albopictus*, and *Anopheles gambiae*.

In another aspect, the invention provides a method of producing the modified arthropod.

In one embodiment, the modified arthropod has a reduced susceptibility to a pathogen.

Typically, according to this embodiment, said pathogen is selected from the group consisting of a virus, a fungus, a protozoan, a nematode, and a bacterium.

In another embodiment, the modified arthropod has a reduced life-span.

Typically, according to this embodiment, said "reduced life-span" is shorter than an average life-span of a wild-type of said modified arthropod. Accordingly, said reduced life-span may be 10%, 20%, 30%, 40%, 50%, or up to 80% shorter than the average life-span of a wild-type of said arthropod.

It will be appreciated that the modified arthropod may be less likely to transmit a pathogen than its wild-type counterpart, since most pathogens have to undergo a relatively long incubation period in an arthropod vector before they can be transmitted to a new host.

In yet another embodiment, the modified arthropod has a reduced fecundity.

In one particular embodiment, said reduced fecundity may result in a loss of progeny following a cross between a modified male arthropod and a wild-type female arthropod.

In another particular embodiment, the modified arthropod (e.g. a mosquito) may be used in a method for controlling the growth of an arthropod population during the dry period since eggs from a modified arthropod (e.g. a female mosquito) have a reduced tolerance to desiccation and a shorter life-span compared to eggs from a wild-type arthropod.

As used herein, "reduced tolerance to desiccation" refers to a reduced, diminished or decreased ability of eggs from an arthropod to withstand or endure extreme dryness or drought-like conditions.

According to this particular embodiment, the life-span of eggs from a modified arthropod (e.g. a mosquito) may be at least 4 weeks, at least 8 weeks, at least 12 weeks, and up to at least 18 weeks shorter than eggs from said wild-type arthropod.

In another aspect, the invention provides a method of modifying an arthropod population, said method including the step of introducing the modified arthropod into said arthropod population, to thereby modify one or more biological properties of said arthropod population.

Preferably, said arthropod population is an insect vector population.

More preferably, said arthropod population is a mosquito vector population.

Even more preferably, said arthropod population is a disease-transmitting mosquito vector population.

In one embodiment, this aspect provides a method of mitigating, reducing, or decreasing pathogen transmission by said arthropod population.

In another embodiment, this aspect provides a method of reducing, mitigating, or decreasing a susceptibility to a pathogen in said arthropod population.

Typically, according to this embodiment, said pathogen is selected from the group consisting of a virus, a fungus, a worm, a protozoan, and a bacterium.

In one particular embodiment, said pathogen is a protozoan of the genus *Plasmodium*.

In another particular embodiment, said pathogen is of a species selected from the group consisting of *Plasmodium falciparum, Plasmodium vivax, Plasmodium ovale, Plasmodium malariae, Plasmodium berghei, Plasmodium gallinaceum*, and *Plasmodium knowlesi*.

In yet another particular embodiment, said pathogen is a virus of the genus *Flavivirus* (e.g., a dengue virus).

Accordingly, in a non-limiting example, an arthropod population (e.g. a population of *Aedes aegypti*) comprising one or more modified arthropods may have a reduced susceptibility to a pathogen (e.g. a malaria parasite or a dengue virus), compared to a corresponding wild-type arthropod population.

In yet another embodiment, this aspect of the invention provides a method of reducing, lowering, shortening, or decreasing an average life-span of said arthropod population.

It will be appreciated that an arthropod population with a reduced average life-span compared to a corresponding wild-type arthropod population may have a reduced capacity to transmit pathogens, such as viruses, fungi, worms, parasites, and bacteria, since a pathogen must undergo a significant period of development in their arthropod vector before it can be transmitted to a new host. Accordingly, a reduction of the average life-span of a disease-transmitting mosquito population may help reduce transmission of vector-borne diseases such as, but not limited to, malaria, dengue fever, and lymphatic filariasis.

In yet another embodiment, this aspect of the invention provides a method of reducing, lowering or decreasing an average fecundity of said arthropod population.

In one particular embodiment, said reduced average fecundity results in a loss of progeny following a cross between a modified male arthropod and a wild-type female arthropod.

In another particular embodiment, said reduced average fecundity results in a reduced life-span of eggs from a modified female arthropod.

In still yet another embodiment, this aspect of the invention provides a method of reducing an ability of an arthropod population to feed from a host.

It will also be appreciated that the methods of this aspect may be used together with other agents that reduce an average life-span of an arthropod population. Such agents include entomopathogenic fungi and mosquito densoviruses, although without limitation thereto.

So that the invention may be fully understood and put into practical effect, the skilled reader is directed to the following non-limiting detailed Examples.

EXAMPLES

Example 1

Host Adaptation of *Wolbachia* after Long-Term Serial Passage in Mosquito Cell Lines Materials and Methods Cell Lines and Maintenance Three cell lines were used in this study: (i) Aa23.T derived from *Ae. albopictus* embryos (O'Neill et al., 1997) (ii) RML-12 derived from *Ae. aegypti* larvae (C. E. Yunker; personal communication) (Kuno, 1983) and (iii) MOS-55 derived from *An. gambiae* larvae (Marhoul and Pudney, 1972). All these cell lines were confirmed as negative for *Wolbachia* infection prior to this study by PCR as outlined below. Aa23.T and RML-12 cell lines were maintained in growth medium consisting of equal volumes of Mitsuhashi-Maramorosch (Mitsuhashi and Maramorosch, 1964) (1 mM $CaCl_2$, 0.2 mM $MgCl_2$, 2.7 mM KCl, 120 mM NaCl, 1.4 mM $NaHCO_3$, 1.3 mM $NaH_2PO_4$, 22 mM D (+) glucose, 6.5 g/L lactalbumin hydrolysate, and 5.0 g/L yeast extract) and Schneider's Insect Medium (Sigma-Aldrich, St Louis, Mo.) supplemented with 10% heat-inactivated fetal bovine serum (HIFBS). MOS-55 was maintained in Schneider's Insect Medium supplemented with 20% HIFBS. Both media also contained penicillin (50 U/mL) and streptomycin (50 µg/mL). For routine maintenance, cells were grown in 25 $cm^2$ plastic tissue culture flasks containing 5 mL of medium at 26° C. without $CO_2$ incubation. Cells were passed every 3-4 days by vigorous shaking of the flask, and seeding a new flask with 20% of the resuspended cells with 5 mL fresh media.

Establishment of wMelPop Infected Cell Lines wMelPop was purified from *D. melanogaster* $w^{1118}$ embryos (Min and Benzer, 1997) and established in an uninfected *Ae. albopictus* cell line (Aa23.T) using the shell vial technique (Dobson et al., 2002). Embryos were collected every 45 min on molasses agar plates covered with live yeast paste and dechorionated using freshly prepared 50%-diluted bleach (White King, Victoria, Australia) (2.1% sodium hypochlorite final concentration) for 2 min. Embryos were then rinsed several times in sterile $dH_2O$, immersed in 70% ethanol for 15 sec, and rinsed three times in sterile PBS, pH 7.4. Approximately 20 mg of surface sterilized embryos (~50-100 µL of packed embryos) were then transferred to a mini Dounce tissue homogenizer (Wheaton, USA) and suspended in 400 µL of PBS. Embryos were then homogenized for 2-3 min with a tight pestle. 200 µL of homogenate was then overlaid separately onto two 80% confluent wells of Aa23.T cells prepared 24 hr earlier in a 12-well cell culture plate. The plate was then centrifuged at 2000 g for 1 hr at 15° C. Cells were then incubated at 26° C. for 24 hr and the contents of each well transferred to individual 25 $cm^2$ cell culture flasks with 5 mL of fresh media. After a confluent monolayer had formed, cells were split 1:5 and passaged as usual.

To establish the infection in *Ae. aegypti* RML-12 and *An. gambiae*, MOS-55 cell lines, wMelPop, was purified from Aa23 cells as described below and introduced into these cell lines using the shell vial technique.

Characterization of wMelPop in Cell Lines

*Wolbachia* infections were characterized in cell lines using (i) PCR screening and sequencing, and (ii) electron microscopy. For each assay naturally uninfected or tetracycline-cured derivatives of each cell line were used as negative controls.

(i) PCR Screening and Sequencing

To monitor infection status of cells, DNA was extracted from cultures as previously described (Dobson et al., 2002) and amplified using the general *Wolbachia* surface protein (wsp) primers 81F and 691R, or the diagnostic wsp primer set for wMelPop, 308F and 691R (Zhou et al., 1998). To confirm the presence of wMelPop in these three cell lines, fragments of the *Wolbachia* 16S rRNA and wsp gene were PCR-amplified, cloned and sequenced. DNA was extracted from cells using a DNeasy Tissue kit (Qiagen) and amplified as previously described using the diagnostic primers 99F and 994R for the *Wolbachia* 16S rRNA gene (O'Neill et al., 1992), and the primers 81F and 691R for the wsp gene (Zhou et al., 1998). Total DNA from cell lines was also PCR-amplified using the general eubacterial 16S rRNA primers 10F/1507R (Mateos et al., 2006) and 968F/R1401R (Nubel et al., 1996). The resulting PCR products were cloned into the pGEM-T easy vector (Promega) and four clones from each infected cell line randomly selected and sequenced for each product. The presence of wMelPop and no other contaminating bacteria in cell lines was verified by denaturing gradient gel electrophoresis (DGGE), using a general primer set targeting eubacterial 16S rRNA genes (F-968-GC and R-1401) (Nubel et al., 1996), using previously described methods (Pittman et al., 2008).

(ii) Electron Microscopy

Insect cells were washed in PBS and rapidly fixed with microwave processing in 2.5% glutaraldehyde solution containing 0.1% $CaCl_2$ and 1% sucrose in 0.1 M Na cacodylate, enrobed in 2% agarose, and postfixed in 1% osmium tetroxide in 0.1 M Na cacodylate buffer. Samples were then dehydrated in a sequence of increasing ethanol concentration and in a final step in acetone (100%), and then embedded in epoxy resin (Epon 812) using microwave processing (Feinberg et al., 2001; O'Neill et al., 1997). Ultra-thin sections (50-80 nm) prepared on a Leica Ultracut T ultramicrotome (Leica Inc.) were then placed on copper grids and stained with 2% uranyl acetate followed by Reynolds lead citrate. The sections were then examined in a JEOL-1010 electron microscope operated at 80 kV.

Purification of *Wolbachia* from Cell Culture for Embryonic Microinjection

Insect cells from the confluent monolayers of two 175 $cm^2$ flasks were harvested and centrifuged in 50 mL conical flasks at 1000 g for 5 min at 4° C. and the cell culture media discarded. The cellular pellet was then washed in SPG buffer (218 mM sucrose, 3.8 mM $KH_2PO_4$, 7.2 mM $K_2HPO_4$, and 4.9 mM L-glutamate, pH 7.2) and the centrifugation and wash steps repeated. After washing, the pellet was resuspended in 5 mL SPG and sonicated twice on ice for 10 sec at 12.5 W with a Fisher Scientific model 60 Sonic Dismembranator (3 mm microtip diameter) to lyse the cells. This suspension was then centrifuged at 1,000 g for 5 min at 4° C. to pellet cellular debris. The supernatant was then passed through a 5 µM Acrodisc syringe filter (Pall Life Sciences) and the filtrate collected in 1.5 mL microcentrifuge tubes. These were then centrifuged at 12,000 g for 15 min at 4° C. to pellet *Wolbachia*. The supernatant was then discarded, pellets were combined and resuspended in 400 µL SPG buffer and centrifuged at 300 g for 5 min to remove any remaining debris (Xi and Dobson, 2005). The supernatant was then transferred into a clean tube and stored on ice until used for injection (<3 hr).

Embryonic Microinjection

Purified *Wolbachia* from RML-12 was microinjected into embryos of the *D. melanogaster* line $w^{1118}$.T (Min and Benzer, 1997). Prior to microinjection, this line was confirmed to be free of *Wolbachia* by PCR using primers specific for the wMelPop IS5 repeat: IS5-FWD1 (5'-GTATCCAACAGATCTAAGC) (SEQ ID NO: 1) and IS5-REV1 (5'-ATAACCCTACTCATAGCTAG) (SEQ ID NO: 2). IS5 is a multicopy insertion element, and as such a much more sensitive target for determining infection status than single copy genes such as wsp. For microinjection, early (pre-blastoderm) stage embryos were collected every 30 min using molasses agar plates with live yeast paste. Purified *Wolbachia* was microinjected into the posterior pole of embryos within 30 min of collection using standard techniques (Ashburner, 1989; Boyle et al., 1993; Xi and Dobson, 2005). After hatching, larvae were transferred to a standard cornmeal based *Drosophila* rearing medium (Ashburner and Roote, 2000) and incubated at 24° C.

*Drosophila* Rearing and PCR Screening for Infection Status

Virgin females resulting from injected embryos (generation 0 [G0]) were placed in vials with three $w^{1118}$.T males to establish isofemale lines. After egg laying G0 females were sacrificed and DNA extracted using the Holmes-Bonner DNA extraction protocol (Holmes and Bonner, 1973). *Wolbachia* was detected in samples using PCR primers specific for the IS5 repeat element in wMelPop. The quality of the insect DNA was assessed using the primer set 12SA1 and 12SB1 that amplifies the *D. melanogaster* 12S ribosomal RNA gene (O'Neill et al., 1992). Amplification of DNA was carried out in a 20 µL reaction volume which included: 2.0 µL of 10× buffer (New England Biolabs, Beverly, Mass.), 25 µM of dNTPs, 0.5 µM of forward and reverse primer, 0.75 U of Taq polymerase (New England Biolabs, Beverly, Mass.), and 1.0 µL of DNA template. PCR conditions were as follows; denaturation at 94° C. for 3 min; 35 cycles of denaturation at 94° C. for 30 sec, annealing at 55° C. for 30 secs, and extension at 72° C. for 1 min; followed by a final 10 min extension step at 72° C.

To select for a stable infection, only offspring from females that tested positive for *Wolbachia* by PCR screening were used as parental stock. Each generation, 25-50 females from each line were isolated as virgins, placed into individual vials and outcrossed to three $w^{1118}$.T males. Females that tested negative for *Wolbachia* were discarded along with their progeny. This selection regime was maintained for three generations after which the lines were closed. The two resulting lines, wMelPopCLA-1 and wMelPopCLA-2, were then monitored periodically by PCR to confirm infection status. The selection regime was again repeated at $G_{14}$ due to fluctuations in infection frequencies in both lines.

Lifespan Assays

The lifespan of wMelPopCLA-1, wMelPopCLA-2 and wMelPop lines was compared to tetracycline-cured derivatives of each line created by the addition of tetracycline into the adult diet (3 mg/mL) according to standard methods (Hoffmann et al., 1986). Treated flies were reared on tetracycline for two generations, and then transferred to a normal diet for a minimum of five generations before being used in experiments. To reduce genetic drift effects that may have occurred in these lines during tetracycline treatment, 100 females from each fly line (including infected lines) were backcrossed with 100 males from the same $w^{1118}$.T stock line and the progeny combined to form the next generation. This was repeated for five generations ($G_{23}$-$G_{28}$). Longevity assays were then conducted at $G_{31}$, $G_{33}$ and $G_{35}$. To control for any crowding effects or size variability, the larval density of each stock bottle used to obtain flies was standardized (200 larvae/bottle) prior to longevity assays. Stock bottles were kept at 24° C. until adult eclosion 9-10 days later, when flies were sexed as virgins and separated. In each assay, six vials of 20 flies for each sex were maintained at 29° C. in standard cornmeal food vials without additional live yeast. Each day the number of new deaths were recorded. Flies were moved to fresh food vials every five days. Survival curves for the various treatment groups were compared using a mixed effects Cox Proportional Hazard (coxme) model of survival analysis using the kinship package of the R suite of statistical software (www.r-project.org).

Cytoplasmic Incompatibility (CI) Tests

CI tests were conducted at G36 and G38 post-transinfection using the previously backcrossed lines. To standardize rearing conditions for CI tests, fly stock bottles were grown under low-density conditions (n=150-200) at 24° C. with a 12 hr light/dark cycle. To obtain offspring for CI crosses, stock bottles were seeded with a set density of 200 eggs per 40 mL of diet. After eclosion, flies were sexed and separated as virgins and aged until CI tests. Male flies were collected on day 2 of emergence and were used within 24 hr of eclosion (Reynolds et al., 2003; Yamada et al., 2007). The female flies used were 5-7 days old. For each cross, single mating pairs (n=40) were introduced to plastic bottles with molasses plate lids. Pairs were given 24 hr to mate, then the males were removed and the females allowed to lay eggs. Eggs were collected every 24 hr on molasses agar plates dotted with live yeast suspension for three days. Females that laid <50 eggs total across the three plates were discarded from the experiment. The plates were then placed at 24° C. for a further 36-48 hr, and then the number of total and unhatched eggs were counted. Statistical significance of hatch rates for various crosses was determined using a Mann-Whitney U-Test. A Bonferroni correction was used to compensate for multiple comparisons.

Quantitative PCR and Density Determination

To examine if the density of *Wolbachia* in *D. melanogaster* had changed after long-term serial passage in mosquito cell lines, infection densities were monitored in head tissues of $w^{1118}$ flies carrying the wMelPopCLA-1, wMelPopCLA-2 or wMelPop strain over their lifespan using quantitative PCR (qPCR). Heads were selected for qPCR as wMelPop infection densities had previously been shown to rapidly increase in nervous tissue with adult age (McGraw et al., 2002; Min and Benzer, 1997). Density of the closely-related non-virulent *Wolbachia* strain wMel was also examined after introgression for three generations from $yw^{67c23}$ into the $w^{1118}$ genetic background. qPCR assays were conducted at $G_{46}$ post-transinfection. Flies reared as described for lifespan assays were collected at four-day intervals (from 4-32 days) until all the flies in a line were dead, and stored at −80° C. before analysis. Total DNA was extracted from dissected head tissues using the DNeasy tissue kit protocol (Qiagen). To estimate the relative abundance of *Wolbachia* in each sample, we compared abundance of the single-copy *Wolbachia* ankyrin repeat gene WD0550 to the single-copy *D. melanogaster* gene Act88F. The following primers were used to amplify a 74 bp amplicon from WD0550 (For 5'-CAGGAGTTGCTGTGGGTATATTAGC (SEQ ID NO: 3) and Rev 5'-TGCAGGTAATGCAGTAGCGTAAA (SEQ ID NO: 4)); and a 78 bp amplicon from Act88F (For 5'-ATCGAGCACGGCATCATCAC (SEQ ID NO: 5) and Rev 5'-CACGCGCAGCTCGTTGTA (SEQ ID NO: 6)). 12 biological replicates were examined per time point for each treatment. For each sample, qPCR amplification of DNA was performed in triplicate using a Rotor-Gene 6000 (Corbett Research, Australia). Amplification was carried out in a 10 µL reaction volume which included: 5 µL Platinum SYBR Green I Supermix (Invitrogen, CA), 1 µM of forward and reverse primer and 1 ng DNA template. The PCR conditions were 50° C. for 2 min; 95° C. for 2 min; 40 cycles of 95° C. for 5 sec, 60° C. for 5 sec and 72° C. for 10 sec; followed by a melt curve from 67° C. to 95° C. A standard calibrator was used to normalise between qPCR runs; and the specificity of PCR products was determined by melt-curve analysis. Crossing threshold ($C_t$) and amplification efficiency values for each sample were calculated using Corbett Rotor-Gene (Version 1.7.75) software. The relative abundance of Wolbachia in each sample was then determined using the method discussed by Pfaffl (Pfaffl, 2001). Regression analysis was used to detect trends in density of Wolbachia over the lifetime of individual fly lines. ANCOVA was then employed to examine the relationship between density and the covariates age and strain. All abundance data were log transformed prior to analysis. A Bonferroni correction was used to compensate for multiple comparisons.

Results

Several initial attempts to establish wMelPop in the Ae. albopictus embryonic cell line Aa23 were unsuccessful. Typically infection was lost after several passages, or lines were discontinued due to a complete loss of confluence or growth of mosquito cells. This situation mirrors that observed when wMelPop purified from Drosophila is injected into mosquitoes, with large fluctuations in infection density eventually leading to loss of infection (EAM and SLO unpublished data). In total, only 2 out of 68 (3%) independent attempts to establish the wMelPop infection in Aa23 cells were successful.

Figure 1:
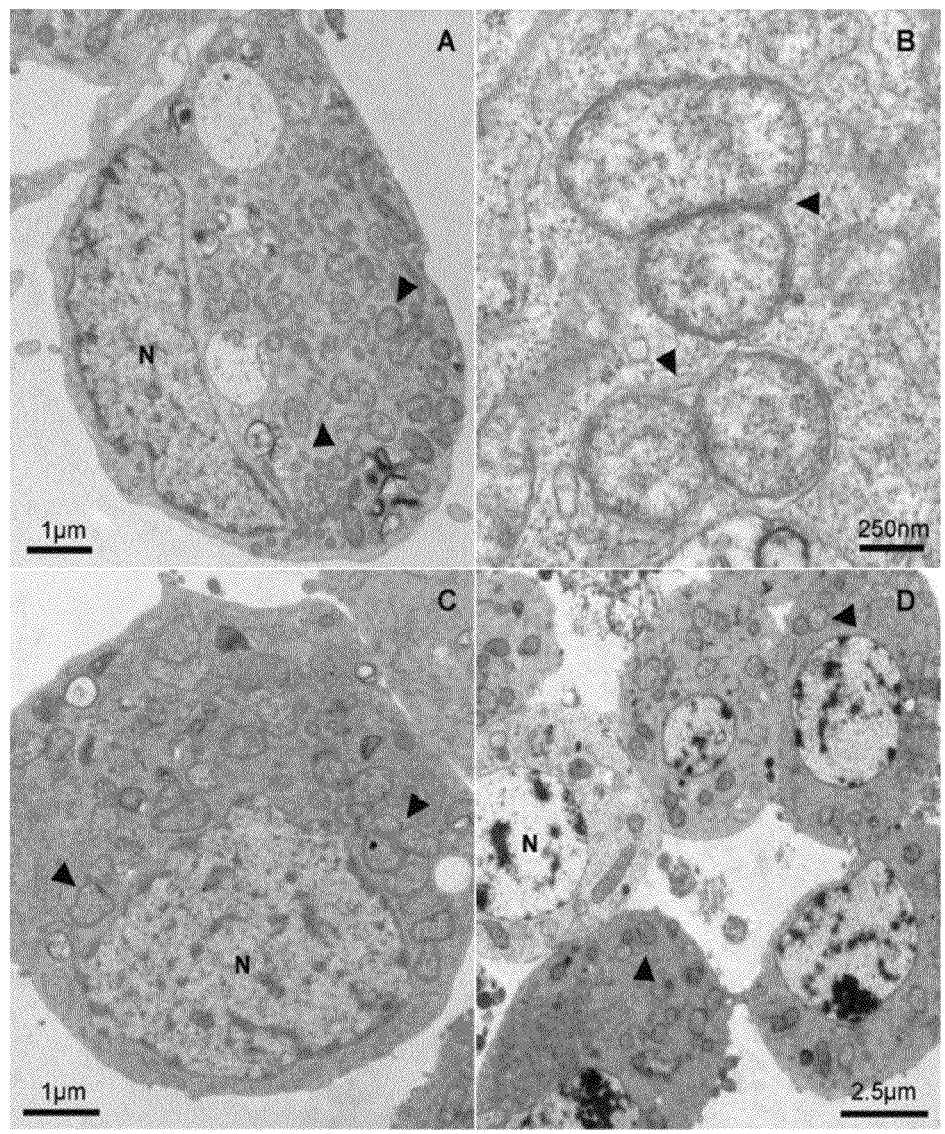
FIG. 1. Electron microscopy of wMelPop in mosquito cell lines. (A) Low magnification transmission electron micrograph showing a large number of *Wolbachia* (examples marked with arrow heads) dispersed throughout the cytoplasm of an *Ae. aegypti* RML-12 cell. (B) High magnification micrograph of four *Wolbachia* presumably undergoing the process of cell division in RML-12 cells (arrow heads) (C) Low magnification micrograph showing the presence of several *Wolbachia* in the cytoplasm of an *Ae. albopictus* Aa23 cell (D) A cluster of *An. gambiae* MOS-55 cells each infected by multiple *Wolbachia*.

Once established in Aa23, wMelPop was serially passaged for 237 passages (~2.5 years) before being transferred to the Ae. aegypti cell line RML-12 and the An. gambiae cell line MOS-55. Stable establishment of wMelPop in these two cell lines occurred much more easily than the initial infection of Aa23, with 2 out of 2 independent attempts for each cell line forming stable wMelPop infections. Partial sequences of the Wolbachia 16S rRNA and wsp genes from the three cell lines used were all identical to the sequence from wMelPop, confirming that infections were not the result of contamination with other strains. Infection in mosquito cells was also confirmed using transmission electron microscopy (TEM). TEM micrographs of the three infected mosquito cell lines show that representative cells from each line were heavily infected by wMelPop (FIG. 1). wMelPop was purified from the Ae. aegypti RML-12 cell line, and re-introduced back into its native host, D. melanogaster $w^{1118}$, that had been previously cured of its natural wMelPop infection by tetracycline treatment. At the time of re-introduction, wMelPop had been maintained for over 3 years outside its native host: 237 passages in Aa23 and 60 passages in RML-12 cell lines. In total, 446 embryos were microinjected giving rise to 108 $G_0$ larvae (24% hatch). All 10 surviving $G_0$ females were PCR positive for Wolbachia. Of these, 8 produced offspring, and 2 produced PCR positive $G_1$ isofemale lines. These two independent isofemale lines were named "wMelPopCLA-1" and "wMelPopCLA-2" (wMelPop Cell Line Adapted).

Figure 2:
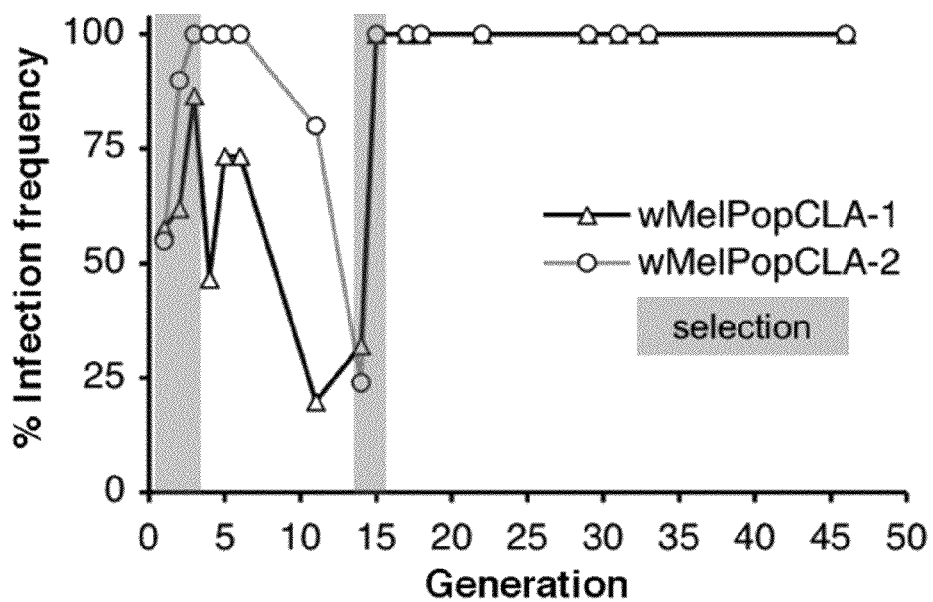
FIG. 2. *Wolbachia* infection frequencies of *D. melanogaster* wMelPopCLA-1 and wMelPopCLA-2 lines post-transinfection ($G_0$). Grey shaded regions represent periods of experimental selection for infection.

The infection frequency in wMelPopCLA lines was then monitored periodically over time (FIG. 2). Both wMelPop-CLA lines were initially observed to display variable maternal transmission rates in the original Drosophila host, reflected in fluctuating infection frequencies in the absence of experimental selection. During an initial period of experimental selection for increased infection ($G_1$-$G_3$ post-transinfection), frequencies as detected by PCR were observed to increase in both wMelPopCLA-1 (58% to 87%) and wMelPopCLA-2 (55% to 100%). In the absence of experimental selection from $G_4$ onwards, infection frequencies in both lines initially were stable or fluctuated, but then rapidly decreased such that by $G_{14}$ post-transinfection only 32% of wMelPopCLA-1 and 24% of wMelPopCLA-2 individuals remained infected. Selection was repeated again at $G_{14}$ and after one additional generation infection frequencies in both lines moved to 100% and remained fixed for infection to $G_{46}$ when last assayed.

Figure 3:
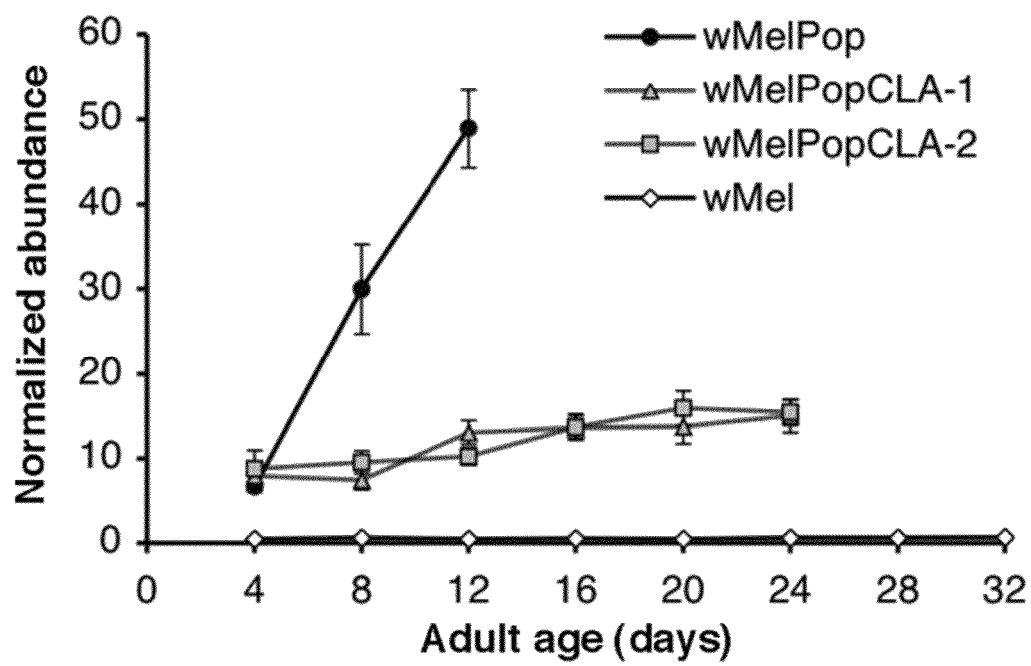
FIG. 3. Mean relative *Wolbachia* densities in fly heads (±SE, n=12 per each point) as determined by real-time quantitative PCR for four lines of infected flies collected at various ages over their lifespan at 29° C. Flies were sampled at four-day intervals until dead.

To assess the effect of continuous cell line culture on the ability of this Wolbachia strain to colonize Drosophila, we compared infection densities in flies that contained wMelPopCLA with those carrying the original wMelPop infection by qPCR. Since it is known that wMelPop densities increase rapidly in adult flies when held at 29° C., we assessed Wolbachia densities across the adult lifespan. As populations of flies aged, Wolbachia densities in head tissue rapidly increased in wMelPop infected flies (FIG. 3). The density of Wolbachia also increased in wMelPopCLA-1 and wMelPop-CLA-2 infected flies as they aged, although these increases were noticeably less than wMelPop. Wolbachia densities were roughly four fold higher in wMelPop-infected flies when compared to wMelPopCLA-1 or wMelPopCLA-2 infected flies at day 12 post-emergence. Flies infected with the non life-shortening wMel strain had the lowest infection which only increased slightly over the lifespan of flies. Overall, there was a significant effect of age and strain on Wolbachia density ($F_{1,275}$=41.92, P<0.001 for age; $F_{3,275}$=678.37, P<0.001 for strain) for all lines. This was reflected by significant differences in the effects of strain and age after pair-wise comparisons between lines (P<0.001 for all comparisons), except for wMelPopCLA-1 and wMelPopCLA-2 lines where strain effects were not significantly different from one another ($F_{1,144}$=0.09, P>0.05).

Figure 4:
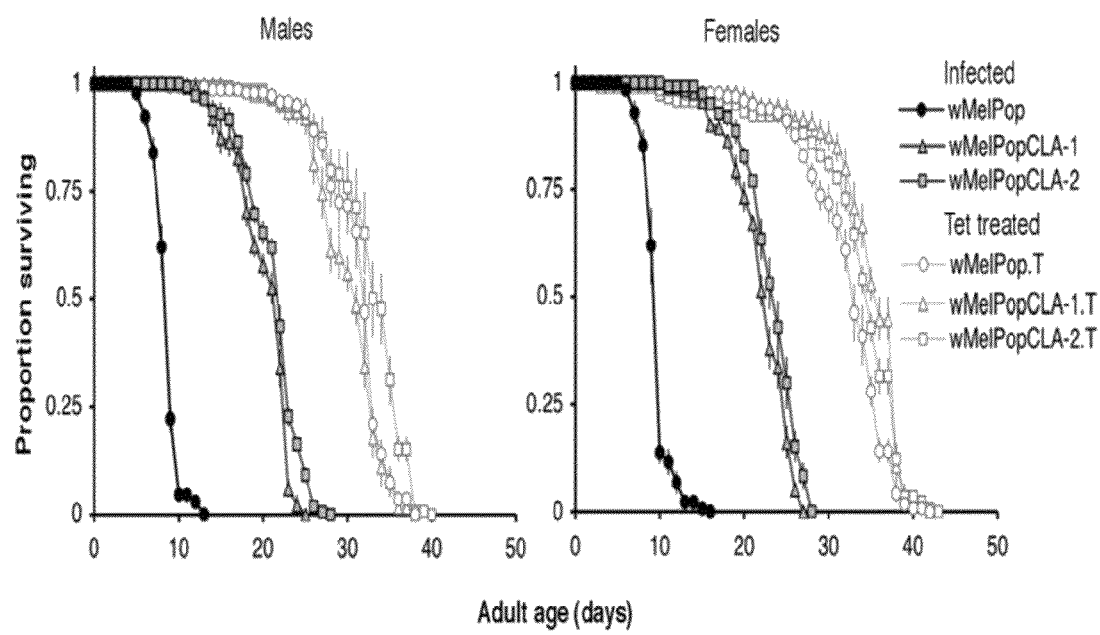
FIG. 4. Survival curves of populations of male and female flies from wMelPop and wMelPopCLA lines at $G_{31}$ post-transinfection. Shaded lines represent infected flies and unshaded lines represent uninfected tetracycline-treated counterparts. Error bars on curves represent standard error. Adult flies were maintained at 29° C.

To test whether the ability of wMelPop to induce the life-shortening phenotype had changed during long-term serial passage, we conducted a series of longevity assays at $G_{31}$, $G_{33}$ and $G_{35}$ post-transinfection. For these experiments, the survival of infected flies from wMelPopCLA-1, wMelPop-CLA-2 and wMelPop lines was compared with uninfected tetracycline-treated lines of each strain at 29° C. Survival curves for males and females of each treatment group were measured independently. In all assays, male and female flies from the wMelPop-infected line demonstrated the most pronounced lifespan reduction when compared to flies from the wMelPop-CLA lines and tetracycline-treated controls (FIG. 4). The lifespan of wMelPopCLA-1 and wMelPopCLA-2 lines appeared intermediate relative to wMelPop, but were shortened relative to tetracycline treated controls. For example, at $G_{31}$ post-transinfection the mean time to death (±SE) for wMelPop females (9.8±0.1 days) was noticeably shorter than that of wMelPopCLA-1 females (22.2±0.3 days), or wMelPopCLA-2 females (23.4±0.3 days). Mean time to death was increased for tetracycline-treated control lines, with wMelPop.T females (32.1±0.5 days), wMelPop-CLA-1.T females (34.6±0.5 days), and wMelPopCLA-2.T females (33.4±0.6 days) all having extended lifespan relative to infected counterparts. For females, the proportional hazard of death associated with carrying infection was significantly greater for individuals with wMelPop (relative risk ratio, 135.7; 95% confidence interval, 40.3-456.5), compared to those either carrying wMelPopCLA-1 (relative risk ratio, 30.0; 95% CI, 15.4-58.5) or wMelPopCLA-2 (relative risk ratio, 17.7; 95% CI, 10.5-30.7) (P<0.001 for all comparisons to wMelPop). The same trends were also observed for males. These results were consistent with those obtained from measurements at $G_{33}$ and $G_{35}$ post-transinfection (data not shown).

Figure 5:
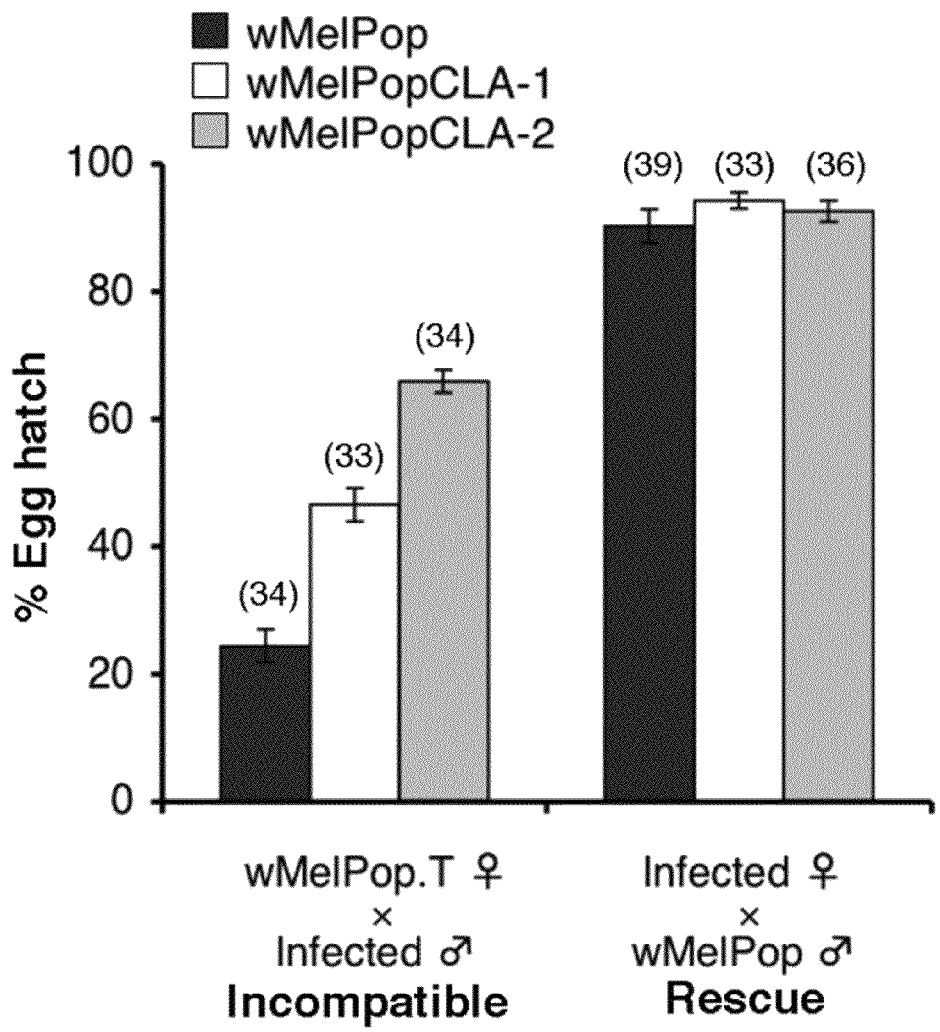
FIG. 5. Ability of wMelPop and wMelPopCLA lines to induce and rescue CI. Mean percentage egg hatch (±SE) for wMelPop.T females mated with infected treatment males (incompatible cross) and; infected treatment females mated with wMelPop males (rescue cross). Bracketed values above error bars represent the number of replicate crosses.

In order to examine effects of long-term cell culture on CI expression we established test crosses between uninfected and infected flies and examined hatch rates of the resulting eggs. Results from incompatible test crosses indicated that wMelPop.T females mated with wMelPop males produced embryos with a mean hatch rate of 24%, which was significantly lower than the same cross with wMelPopCLA-1 males or wMelPopCLA-2 males (Mann Whitney, P<0.001) (FIG. 5). A statistically significant difference in mean hatch rate for crosses with wMelPopCLA-1 males relative to those with wMelPopCLA-2 males (P<0.001) was also observed. In rescue tests, mean hatch rates of embryos produced from crosses between wMelPop males and wMelPop females; wMelPopCLA-1 females; or wMelPopCLA-2 females were not significantly different from one another. As such, lines infected with wMelPopCLA have a reduced ability to induce CI when compared to wMelPop. In contrast, the ability to rescue an incompatible cross appears unchanged in the cell-adapted lines.

Example 2

Stable Introduction of a Life-Shortening *Wolbachia* Infection into Mosquito *Aedes aegypti*

Materials and Methods

Mosquito Strains and Maintenance

The naturally uninfected JCU strain of *Aedes aegypti* was established from *A. aegypti* eggs that were field-collected from Cairns (Queensland, Australia) in 2005. For routine maintenance, eggs were hatched under vacuum for 30 min, and larvae reared at a set density of ~150 larvae in 3 L of distilled water in plastic trays (30×40×8 cm). Larvae were fed with 150 mg (½ tablet) fish food per pan per day (Tetramin Tropical Tablets, Tetra, Germany) until pupation. Adult mosquitoes were maintained in screened 30×30×30 cm cages enclosed within transparent plastic bags, with damp cotton wool to maintain elevated humidity (25±1° C., ~80% relative humidity (RH), 12:12 h light:dark). Adults were provided with constant access to 10% sucrose solution, and females (5 day old) supplied with a human blood source for egg production. PGYP1 and PGYP2 lines were maintained continuously without prolonged desiccation of eggs.

Embryonic Microinjection

Methods used for embryo injections were based upon those successfully used for the transfer of *Wolbachia* to both *Drosophila* and *A. aegypti* (Example 1; Xi et al., 2005). To collect eggs for microinjection, approximately ten gravid JCU females (~5 days post-blood meal) were placed in a *Drosophila* vial with a wet filter paper funnel, and the vial moved to a dark place to promote oviposition. Embryos were collected after allowing females to oviposit for ≤90 min. Pre-blastoderm stage embryos (grey in colour) (Lobo et al., 2006) were aligned on double-sided tape (Scotch 665, St. Paul, Minn.), briefly desiccated, and covered with water-saturated halocarbon 700 oil (Sigma-Aldrich) (Xi et al., 2005). Embryos were then microinjected in the posterior pole with wMelPop, purified as previously described from the *Aedes* cell line RML-12 (see Example 1), using an IM-200 micro-injector (Narishige, Tokyo, Japan). Microinjection needles were prepared from borosilicate microcapillaries (#30-0038, Harvard Apparatus, Kent, UK) using a PC-10 micropipette puller (Narishige, Tokyo, Japan). After injection, embryos were incubated at 80% RH and 25° C. for approximately 40 min, after which time excess oil was removed and embryos transferred to wet filter paper. Embryos were then allowed to develop for 4-5 days, before being hatched and reared to adulthood using the standard maintenance procedures outlined above.

Isofemale Line Rearing and Selection for Stable Infection

Females ($G_0$) resulting from microinjected embryos were isolated as pupae to assure virginity, and subsequently mated with JCU males. Following blood feeding and oviposition, $G_0$ females were sacrificed and DNA extracted using the DNeasy protocol (Qiagen). *Wolbachia* was detected in samples using PCR primers specific for the IS5 repeat element in wMelPop (see Example 1). $G_0$ females that tested negative for *Wolbachia* were discarded along with their progeny. Offspring from females that tested positive for *Wolbachia* by PCR screening were used as parental stock to select for stable infections. PGYP 1 females were outcrossed with JCU males for three generations ($G_0$-$G_2$), after which time this line was closed and infected females and males allowed to interbreed. Typically 50 JCU males and 50 virgin PGYP1 females were used in an outcross. Experimental selection to increase infection frequencies was applied to this line from $G_0$-$G_3$ (FIG. 8A). In the PGYP2 line, females were outcrossed with JCU males for five generations ($G_0$-$G_4$), after which time the line was closed. Experimental selection to increase infection frequency was applied to the PGYP2 line from $G_0$-$G_2$, and subsequently for one generation at $G_8$ (FIG. 8B).

Tetracycline-Treatment of Mosquito Lines

PGYP1 and PGYP2 lines were cleared of wMelPop infection at $G_8$ and $G_{11}$ respectively, by introducing a 1 mg/ml tetracycline solution (final concentration)-dissolved in 10% sucrose—into adult cages (Dobson and Rattanadechakul, 2001). Lines were treated with tetracycline for two generations (with a 14 day course of tetracycline) and then allowed to recover for at least two generations before being used in experiments. Tetracycline-treated lines were confirmed to be cured of wMelPop by PCR as described above. The tetracycline-cleared mosquito strains, designated PGYP1.tet and PGYP2.tet, were also re-colonized with resident gut microflora by adding 100 ml water used to rear untreated JCU larvae to the larval water of treated lines for two generations after tetracycline treatment had ceased.

Lifespan Assays

Three different experimental designs were used for lifespan assays: First, the lifespan of $G_6$ PGYP 1 mosquitoes was compared with those from the naturally uninfected JCU strain at two different temperatures. For these assays, larvae were hatched and reared at 25° C. or 30° C. using the standard method described above. After emergence, adult mosquitoes were maintained in 2.2 L plastic buckets at their treatment temperature; with 80% RH and a 12:12 h light:dark cycle in a controlled growth chamber (Model 620RHS, Contherm Scientific, New Zealand). For each strain at each temperature, six buckets of 50 mosquitoes (25 of each sex) were maintained and checked daily. Cotton balls soaked in 2% sucrose solution as a carbohydrate source were placed inside each cage and changed daily. Second, the lifespan of $G_9$ PGYP1 and JCU mosquitoes was compared under fluctuating abiotic conditions designed to simulate a summer day in Cairns, North Queensland, Australia. Mosquitoes were exposed to a diurnal cycle of 12 h light, 32° C., and 50% RH; and a nocturnal cycle 12 h dark, 25° C. and 80% RH in a controlled growth chamber as above. For this experiment a cohort of 300 adult mosquitoes (150 of each sex) from each strain were maintained in 30×30×30 cm cages. A sugar cube suspended 10 cm below the top of each cage was provided to necessitate flight to obtain a carbohydrate source. A human blood meal was provided to females in each cage daily for 15 min, in addition to a water-filled cup lined with filter paper as an oviposition substrate. Third, larger lifespan assays were conducted to compare survivorship of PGYP1, PGYP2, JCU and tetracycline-cleared strains. These assays were conducted at $G_{13}$ and $G_{15}$ for PGYP1 and PGYP2 lines respectively. For each strain, three replicate 30×30×30 cm cages of 200 mosquitoes (100 of each sex) were maintained at 25±1° C., 70-90% RH, 12:12 h light:dark in a temperature-controlled insectary, with 2% sucrose changed daily. For all three classes of experiments, the number of new deaths was recorded each day until all mosquitoes in the cages were dead. Mosquito survival was analysed using Kaplan-Meier Survival analysis, and log rank tests were used to determine the equality of the survival distributions between treatments.

Cytoplasmic Incompatibility (CI) Tests

Mass crosses were conducted between 35 virgin individuals (3 d old) of each sex from $G_9$ PGYP1 and JCU strains; $G_{13}$ PGYP1 and PGYP1.tet; and $G_{16}$ PGYP2 and PGYP2.tet strains to assess CI levels. Groups were allowed to mate for 2 days before females were blood-fed and isolated individually for oviposition. Eggs were hatched 120 hours after oviposition by submersion in nutrient-infused deoxygenated water (75 mg Tetramin/L) for 48 hr. To hatch any remaining eggs, egg papers were dried briefly and then resubmerged for a further 5 days before the final numbers of hatched larvae were recorded. All females used in crosses were checked for insemination by dissection of spermathecae followed by direct observation of sperm by light microscopy. CI expression was determined by comparing the percentage of hatched eggs from each of the crosses. Statistical significance of hatch rates for various crosses was determined using a Mann-Whitney U-Test. A Bonferroni correction was used to compensate for multiple comparisons. To examine the role of male age on CI, virgin $G_{17}$ PGYP1 and PGYP1.tet males were aged to 3, 10 and 17 d old prior to mating with 3 d old PGYP1.tet virgin females.

Maternal Transmission

The proportion of *Wolbachia*-infected progeny derived from the first and third reproductive cycles of $G_{17}$ PGYP1 females was assessed to provide an estimate of maternal transmission over lifespan. Cohorts of virgin PGYP1 females and uninfected wild-type JCU males were mass-mated. Five days after mating, females were blood-fed, and 72-96 hour post-blood meal, eggs were collected for three days. PGYP1 females were 9 days old at the time of oviposition for the first cycle, and 23 days old for the third cycle. After development, eggs were hatched and DNA extracted from larval offspring using the DNeasy protocol (Qiagen). In total, 515 larvae collected from 31 females (~17 larvae per female); and 527 larvae collected from five cohorts of 20 females (~105 larvae per cohort), were screened from the first and third reproductive cycles respectively. To establish the presence or absence of *Wolbachia*, PCR analysis was performed on individual larvae using IS5 repeat primers as previously described (see Example 1). To ensure that *Wolbachia* negative results were not a result of low quality DNA template, samples were also tested with primers specific for the single-copy *A. aegypti* gene, Ribosomal protein S17 (RpS17) (Cook et al., 2006): Forward 5'-CACTCCCAGGTCCGTGGTAT (SEQ ID NO: 7), Reverse 5'-GGACACTTCCGGCACGTAGT (SEQ ID NO: 8). If samples that were initially negative for *Wolbachia* tested positive for host DNA, they were screened once again with IS5 primers on a range of DNA template concentrations before infection status was finally assigned.

Results

Figure 8:
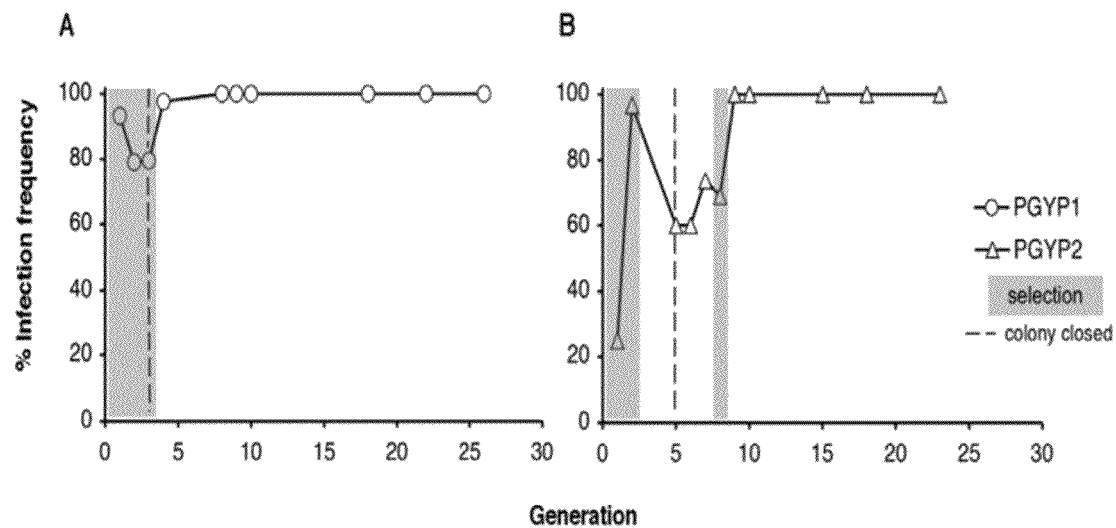
FIG. 8. *Wolbachia* infection frequencies of *A. aegypti* PGYP 1 and PGYP2 strains post-transinfection ($G_0$) (Panels A and B, respectively). Grey shaded regions represent periods of experimental selection for infection where only the offspring from females that tested positive for *Wolbachia* by PCR screening were used as parental stock. Broken lines indicate colony closure where outcrossing of PGYP females to uninfected JCU males ceased, and after which time males and females within the PGYP1 and PGYP2 colonies were allowed to interbreed. Mosquitoes (n=10 males and females per timepoint) from each line were assayed for wMelPop infection using PCR as described.

To facilitate the transfer of the life-shortening *Wolbachia* strain wMelPop that infects *D. melanogaster* (Min and Benzer, 1997) into the mosquito *A. aegypti*, we adapted the bacteria by continuous serial passage in mosquito cell culture for three years. A consequence of this culturing was a reduction in growth rates and associated virulence when transferred back into *Drosophila* (see Example 1). We purified the mosquito cell-line adapted isolate of wMelPop and microinjected it into naturally uninfected *A. aegypti* embryos (JCU strain). Surviving adult females were isolated, blood-fed, and after egg laying were assayed for *Wolbachia* infection using diagnostic PCR (see Example 1; Materials and Methods). Eight independent isofemale lines carrying the wMelPop infection were generated. Six of these lines were lost from $G_1$-$G_3$ (See Materials and Methods), and the remaining two lines formed stable associations. These two lines, 'PGYP1' and 'PGYP2' were chosen for further characterization, and after a period of experimental selection have remained persistently infected by wMelPop (100% infection frequency) until $G_{33}$ and $G_{30}$ respectively, when last assayed (FIG. 8).

Figure 6:
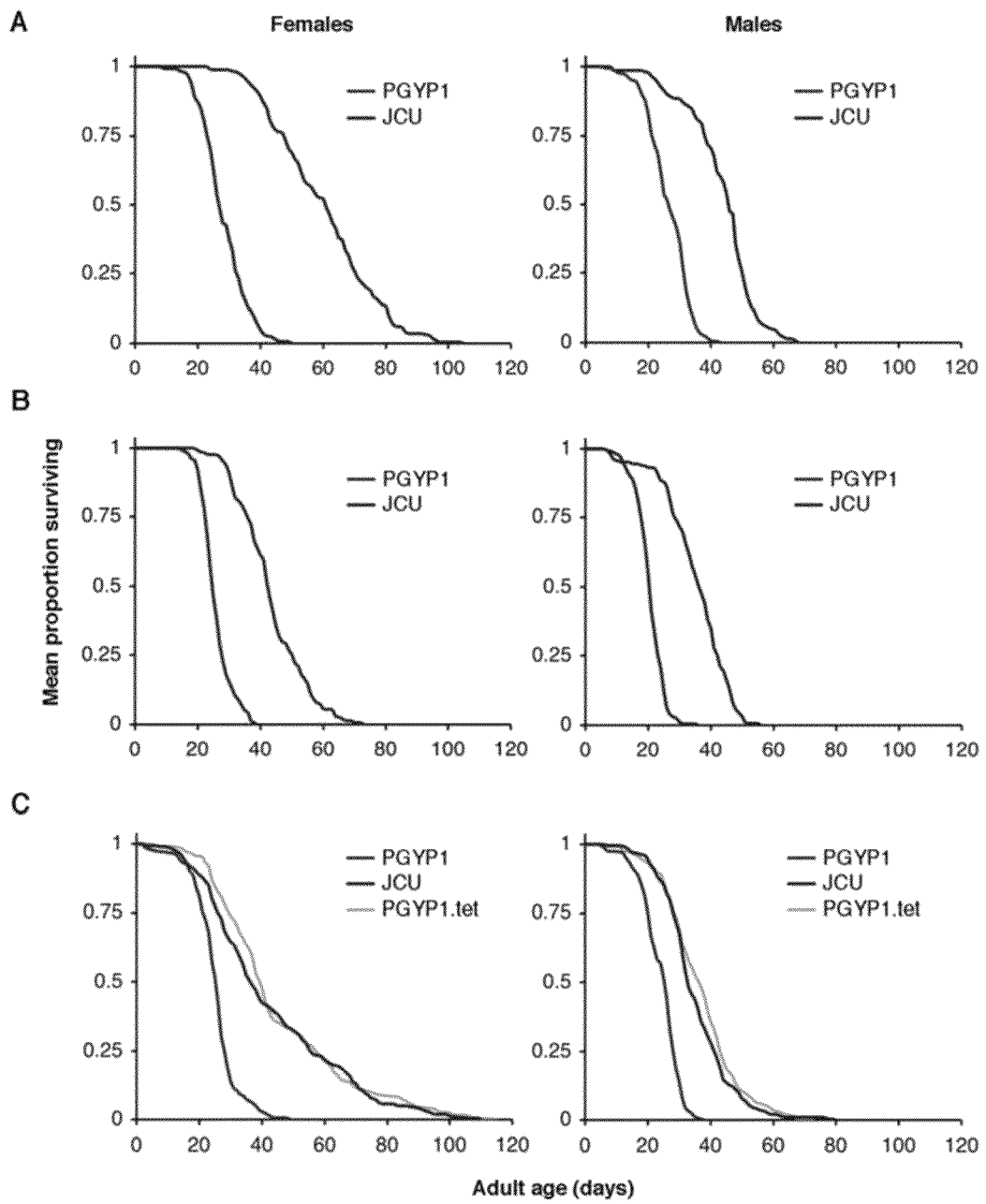
FIG. 6. Survival of wMelPop-infected PGYP1 *A. aegypti* (red lines) compared to the naturally uninfected JCU (blue lines) and tetracycline-cleared PGYP1.tet (grey lines) strains. Lifespan assays were initially conducted at $G_6$ post-transinfection by the comparison of PGYP1 and JCU strains at 25° C. (A) and 30° C. (B). For each strain, six replicate groups of 50 mosquitoes (25 of each sex) were maintained in an incubator at their respective test temperature, and 80% relative humidity. Subsequently, after tetracycline treatment at $G_{13}$ post-transinfection, survival of PGYP1 was compared to PGYP1.tet and JCU strains in larger cages under insectary conditions (C). For this assay, three replicate 30×30×30 cm cages of 200 mosquitoes (100 of each sex) were maintained for each strain at 25±1° C., 70-90% relative humidity, 12:12 h light:dark. In all three experiments mosquitoes were provided with 2% sucrose and cages checked daily for mortality.

In *Drosophila* species, wMelPop shortens the lifespan of adult flies by up to 50% (Min and Benzer, 1997; McGraw et al., 2002). We performed several lifespan assays in *A. aegypti* for a range of experimental conditions. As wMelPop-induced early death in *Drosophila* is temperature sensitive (Min and Benzer, 1997; Reynolds et al., 2003), we compared the lifespan of the newly generated wMelPop-infected PGYP1 line to the naturally uninfected JCU strain at 25° C. and 30° C. (FIGS. 6A and 6B).

In contrast to *Drosophila*, where the life-shortening phenotype is weakly expressed at 25° C. and strongly at 30° C., rapid mortality of PGYP1 mosquitoes ($G_6$) relative to the uninfected parental JCU strain was observed at both temperatures. Under lab conditions at 25° C. and 80% RH (FIG. 6A), the median adult longevity for PGYP1 females of 27.0 days was significantly different from the JCU control of 61.0 days (log-rank statistic 11.67, P=<0.0001). A similar trend was observed for males (FIG. 6A). At a higher temperature of 30° C. and 80% RH (FIG. 6B), the differential effect on median adult longevity was still apparent although the lifespan of all the mosquitoes was reduced: females PGYP1, 25.0 days; JCU, 43.0 days (log-rank statistic 11.50, P=<0.0001).

Figure 9:
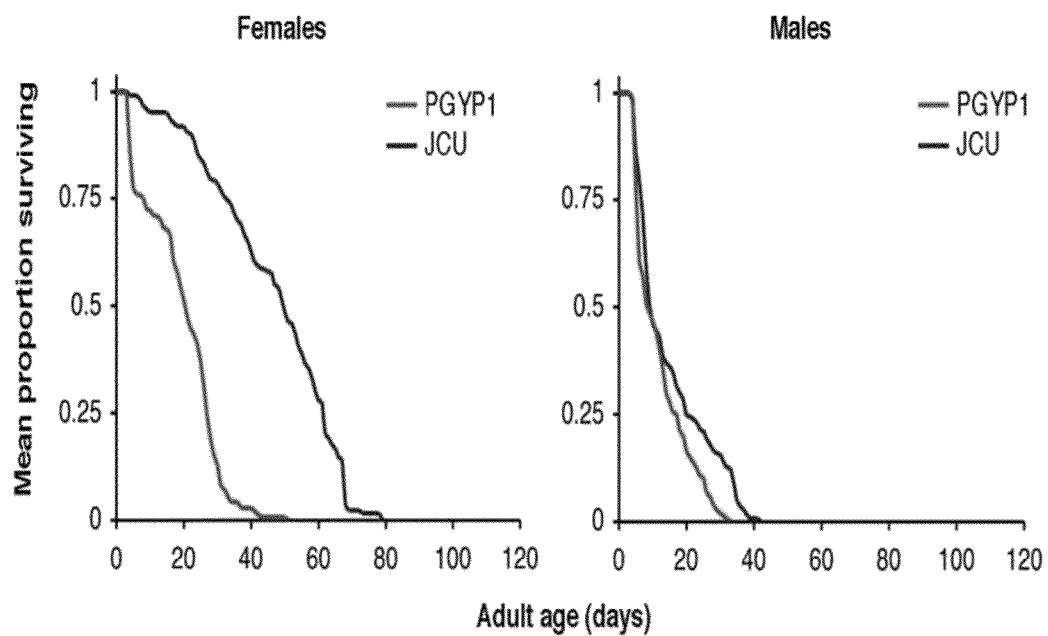
FIG. 9. Survival of wMelPop-infected PGYP1 *A. aegypti* (red lines) compared to the naturally uninfected JCU strain (blue lines) under fluctuating environmental conditions with daily blood feeding. $G_9$ PGYP1 and JCU strains were exposed to a diurnal cycle of 12 h light, 32° C., and 50% RH; and a nocturnal cycle 12 h dark, 25° C. and 80% RH designed to simulate a summer day in Cairns, North Queensland, Australia. For each strain a cohort of 300 adult mosquitoes (150 of each sex) were maintained in 30×30×30 cm cages. Females in each cage were provided with a human blood meal for 15 min each day, and a moist oviposition substrate. Cages were provided with a sugar cube as a carbohydrate source and checked daily for mortality.

To examine the effect of the wMelPop infection under more biologically realistic conditions, we exposed a cohort of PGYP1 ($G_9$) and JCU strains to a fluctuating temperature and humidity regime, and provided female mosquitoes with daily access to a human blood meal (FIG. 9). Under these conditions, the lifespan of PGYP1 females was reduced by more than half relative to JCU females. Median longevity was significantly different between treatments: PGYP1, 21.0 days; JCU, 50.0 days (log rank statistic, 10.13, P=<0.0001). A smaller difference in median survival times was observed for males from both strains (PGYP1, 9.0 days; JCU, 10.0 days), although overall PGYP 1 males still died at a significantly faster rate than JCU males (log-rank statistic=3.34, P=0.0009).

Figure 10:
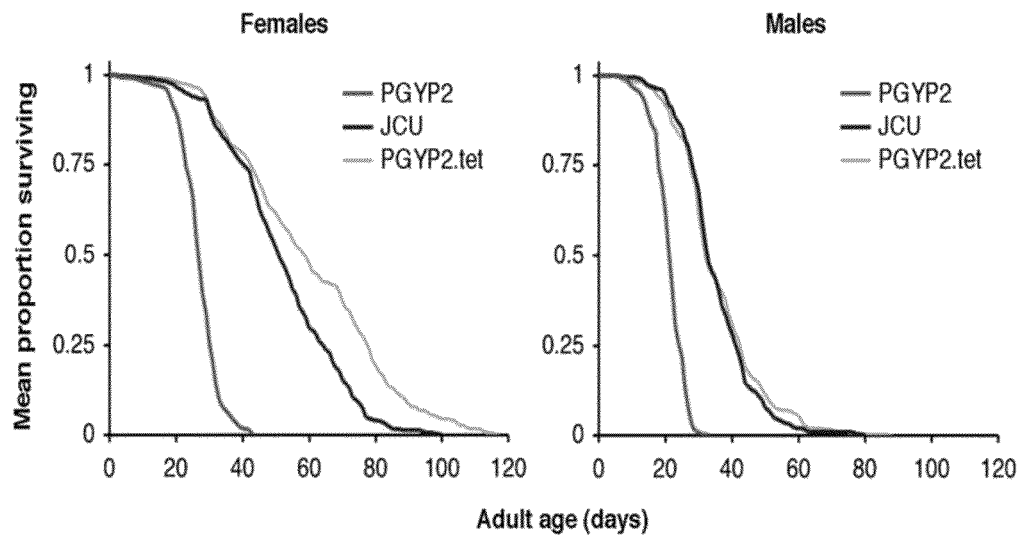
FIG. 10. Survival of wMelPop-infected PGYP2 *A. aegypti* (red lines) compared to the naturally uninfected JCU (blue lines) and tetracycline-cleared PGYP2.tet (grey lines) strains. For each strain, three replicate 30×30×30 cm cages of 200 mosquitoes (100 of each sex) were maintained under insectary conditions at 25±1° C., 70-90% RH, 12:12 h light:dark. Cages were provided with 2% sucrose and checked daily for mortality. Assays were conducted at $G_{15}$ post-transinfection.

To exclude the possibility that observed reductions in lifespan resulted from genetic drift during the establishment of the PGYP 1 strain, we generated an uninfected strain from PGYP1 (PGYP1.tet) by addition of the antibiotic tetracycline to the adult diet (Dobson and Rattanadechakul, 2001). After antibiotic curing of the wMelPop infection (Materials and Methods), no significant differences in the rate of mortality were observed between females or males of uninfected PGYP1.tet and JCU strains (e.g. females, log-rank statistic=1.23, P=0.2191). Both females and males from the PGYP 1 ($G_{13}$) strain had significantly reduced lifespan when compared to those from the PGYP1.tet strain (e.g. females, log-rank statistic=13.70, P=<0.0001), indicative of wMelPop-induced life-shortening (FIG. 6C). These results were confirmed using identical assays with the PGYP2 ($G_{15}$) strain as a biological replicate (FIG. 10).

Figure 7:
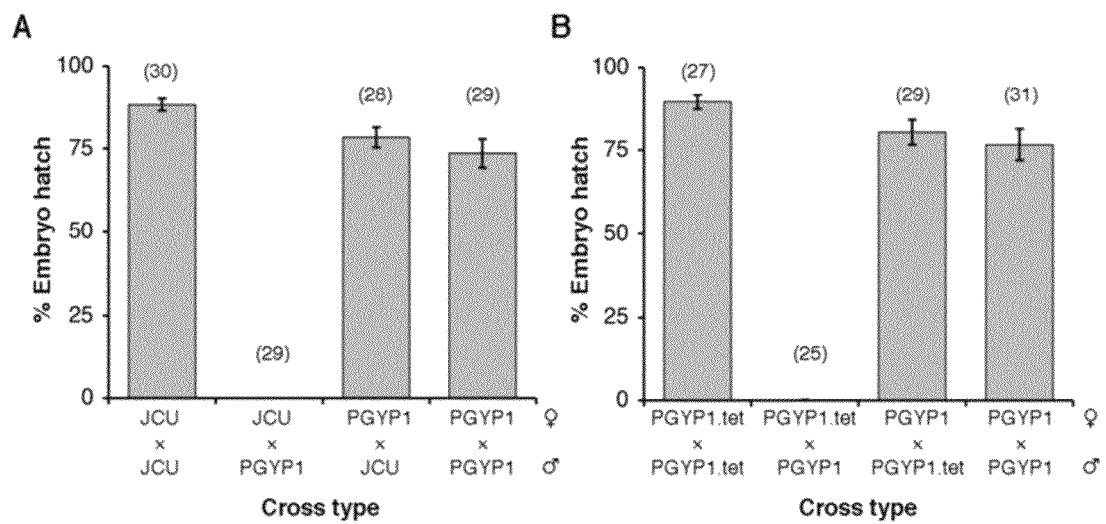
FIG. 7. *Wolbachia*-mediated cytoplasmic incompatibility resulting from crosses of the wMelPop-infected PGYP1 *A. aegypti* strain with the naturally uninfected JCU (A), and tetracycline-cleared PGYP1.tet strains (B). Female parents are listed first in each cross. Results are mean percent embryo hatch±standard error (minimum 1400 embryos total counted per cross), and number of replicates for each of the four cross types are shown in parentheses. Crosses were conducted as described (see Materials and Methods in Example 2).

To test for CI we made crosses between the PGYP1 and wild-type JCU and PGYP1.tet strains and measured egg hatch rates. Consistent with the induction of strong CI in *A. aegypti* (Xi et al., 2005), no eggs hatched from more than 2500 embryos obtained from crosses between male PGYP1 ($G_9$) and uninfected JCU females (FIG. 7A). Similarly, only 2 eggs hatched from more than 1900 embryos obtained from crosses between male PGYP1 ($G_{13}$) and the tetracycline-cleared PGYP1.tet females (FIG. 7B). In both assays, PGYP1 females were capable of rescuing CI, as indicated by the high egg hatch seen in PGYP1×PGYP1 crosses.

In its natural *D. melanogaster* host wMelPop infection induces CI that quickly diminishes with male age (Reynolds et al., 2003). This effect could slow the invasion of the strain into natural populations. Crosses between uninfected *A. aegypti* females and wMelPop-infected males up to 17 days old resulted in a complete absence of egg hatch from more than 9500 embryos (Table 1), indicating wMelPop infection induced CI that is insensitive to male age.

Figure 11:
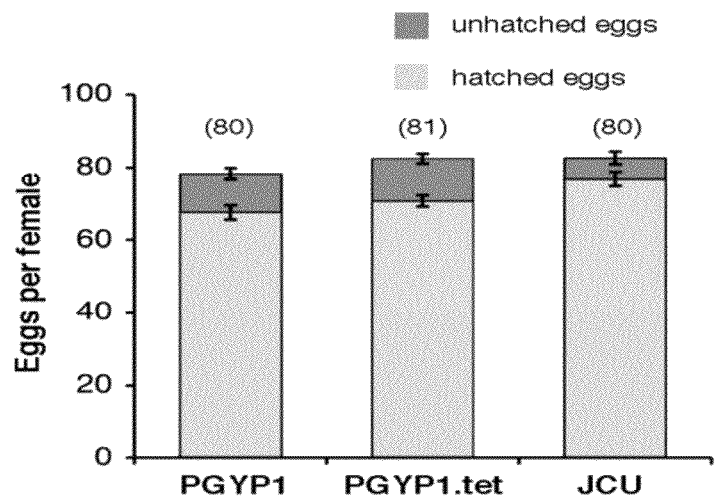
FIG. 11. Fecundity and egg viability of wMelPop-infected PGYP1 *A. aegypti* compared to tetracycline-cleared PGYP1.tet and naturally uninfected JCU strains at $G_{13}$ post-transinfection. Five day old females were fed on human blood, and 96 hours later were isolated individually for egg laying. Eggs hatched 120 h after oviposition, and the percentage of hatched eggs determined. A total of 86% of PGYP1, 86% of PGYP1.tet and 92% of JCU strain eggs hatched. Error bars represent SEM of the total number of eggs and hatched eggs. The numbers of replicates for each strain are shown in parentheses.
Figure 12:
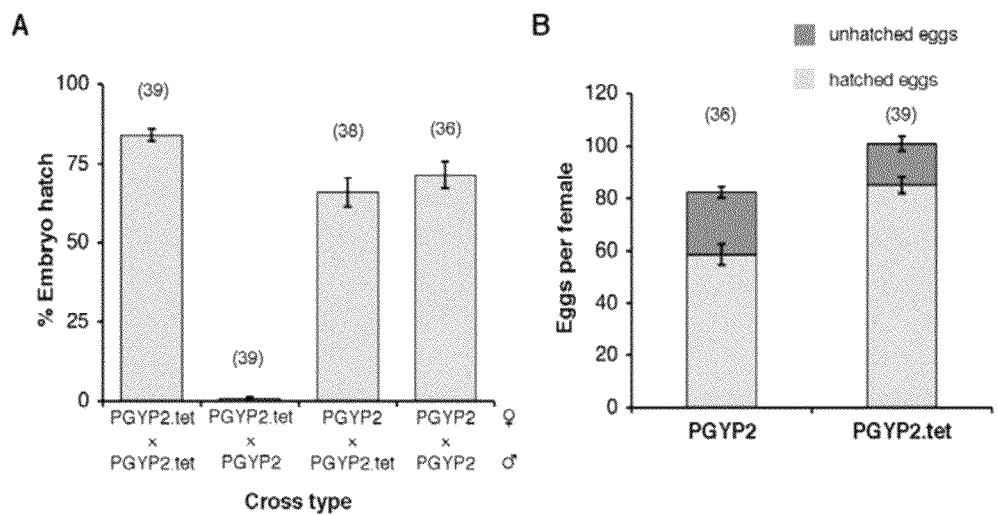
FIG. 12. CI crossing pattern and reproductive fitness of wMelPop-infected PGYP2 *A. aegypti* at $G_{16}$ post-transinfection. (A) For CI assays, PGYP2 *A. aegypti* were crossed with the tetracycline-cleared PGYP2.tet strain as described above. Female parents are listed first in each cross. Results are mean percent embryo hatch±standard error (minimum 2900 embryos total counted per cross), and number of replicates for each of the four cross types are shown in parentheses. (B) To evaluate fecundity and egg viability differences between PGYP2 and PGYP2.tet strains, five day old colony females were fed on human blood, and 96 h post-blood meal females isolated individually for egg laying. Eggs were hatched 120 h after oviposition, and the percentage of hatched eggs determined. Error bars represent SEM of the total number of eggs and hatched eggs, and numbers of replicates for each strain are shown in parentheses.

Overall, no significant differences in fecundity between PGYP1, PGYP1.tet or JCU strains were observed at $G_{13}$ post-transinfection (FIG. 11). An evaluation of CI and reproductive fitness in PGYP2 at $G_{16}$ revealed that the wMelPop infection induced very strong CI, but unlike PGYP1 had a 19% fecundity cost when compared to its tetracycline-cleared counterpart (FIG. 12). In *D. simulans*, fecundity costs associated with the wMelPop infection were initially high after transinfection, but subsequently attenuated, while the life-shortening effect remained stable (McGraw et al., 2002). Further studies are required to determine if this will be the case for PGYP2, and whether observed differences in reproductive fitness between PGYP1 and PGYP2 are related to *Wolbachia* or host genotypes.

High maternal inheritance of *Wolbachia* from infected females to their progeny is a key parameter for successful population invasion. The maternal transmission rate predicts stable prevalence of the infection once it has invaded a population under the action of CI (Hoffmann and Turelli, 1997). To estimate maternal transmission rates of wMelPop over the lifespan of *A. aegypti*, we used the polymerase chain reaction to determine the proportion of *Wolbachia*-infected progeny derived from the first and third reproductive cycles of PGYP1 females ($G_{17}$) mated with uninfected wild-type JCU males. Of the 515 larvae screened from 31 females (~17 larvae sampled per female) from the first reproductive cycle (females aged 9 days old), 99.74±0.26% were infected. This estimate of maternal inheritance was not significantly different from that obtained from the third reproductive cycle (females aged 23 days old) in which 527 larvae were screened from five cohorts of 20 females (~105 larvae sampled per cohort) and were 99.45±0.37% infected (Mann Whitney, P=0.208).

Example 3

Increased Locomotor Activity and Metabolism of Aedes Aegypti Infected with a Life-Shortening Strain of *Wolbachia Pipientis*

Materials and Methods

Experimental Organisms

The wMelPop-infected *Aedes aegypti* line (PGYP1) used in this study was generated as previously described (see Example 2). In brief, the *Wolbachia* strain, wMelPop, native to *Drosophila melanogaster* (Min and Benzer, 1997) was transferred into *Ae. aegypti* by embryonic microinjection. Descendants of this isofemale line were outcrossed for several generations to the original recipient line of mosquitoes and selected for stable infection before closing the colony. At generations 8 & 9 post-transinfection, an aposymbiotic control line was created by antibiotic treatment of the *Wolbachia* infected line (see Example 2). All experiments reported here were carried out on mosquitoes at generations 14-16 post trans-infection (i.e. 4-6 generations post treatment), with replicates representing different generations. Mosquitoes were reared under standard conditions (25° C., 12:12 LD, 80% RH) (Gerberg et al., 1994). Larvae were reared in plastic trays at a density of 150 per three liters of water and supplied with a daily dose of 0.15 g TetraMin aquarium fish food (Tetra, Germany). Adults were separated by sex and maintained as virgins in cages (30×30×30 cm) of ~150 individuals. Adults were supplied with a basic diet of 10% sucrose solution administered through cotton pledgets. The adult ages of 3, 15, and 25 days of age were selected to represent the periods when 100%, ~90%, and ~20% of the wMelPop infected population was still surviving, respectively (see Example 2).

Videorecording of Mosquito Locomotion

Our locomotor assay was based on several previously published models (Allemand et al., 1994; Bonatz et al., 1987; Grobbelaar et al., 1967; Kawada and Takagi, 2004; Liseichikov and Zakharevskii, 1978; Mankin, 1994; Reynolds and Riley, 2002; Rowley et al., 1987; Sbalzarini and Koumoutsakos, 2005), but was most heavily influenced by Williams and Kokkinn (Williams and Kokkinn, 2005). Mosquitoes were placed in an observation chamber during experiments and their motion captured via a video camera. The observation chamber was constructed using white (sides and back) and transparent Perspex (front pane) and contained distinct cells that allowed for the simultaneous observation of 10 individual mosquitoes, one per cell. Mosquitoes were provided with 10% sucrose solution ad libitum during observation periods dispensed through dental cotton wicks (1×ø0.5 cm). The wicks placed in each observation cell also provided constant humidity (80-85% RH). Mosquitoes were transferred from rearing cages to observation chambers 20 min prior to recording of activity to allow them to adapt to the new environment. Recording began daily at 14:30 pm, was paused during the hours of darkness (21:00-07:00) and was completed at 12:30 the following day to allow time to transfer in the next set of mosquitoes. After each observation period mosquitoes were aspirated out of the chamber and sacrificed. The chambers were cleaned with ethanol (80%) and food supply replaced prior to subsequent observation periods. No mosquito mortality was observed during the observations. A total of three replicates each of 10 mosquitoes were studied per sex×strain×age per study chamber.

A two-color camera (DR2-13S2m/C-CS, Point Grey Research, Vancouver, BC, Canada) was fitted with a CCTV lens (12VM412ASIR, Tamron, Commack, N.Y., USA) and fixed on a mounting bracket 110 cm from the chamber. The distance of the camera to the object, the zoom, and the focus and iris aperture were optimized to reduce barreling and distortion of images. A flat light source emitting light intensity was placed 10 cm behind the chamber, which provided sufficient lighting for the camera sensor to capture high quality images but did not increase ambient temperatures. The light source power switch was synchronized with the room lights using a timer. The entire experimental setup was enclosed in cardboard to minimise intrusion of additional stimuli.

The file format used for recording, Audio Video Interleave (AVI), is limited to a maximum size of 2 GB, which amounted to approximately 8 min of video footage. To obtain a continuous video recording, we developed a program called Mossiecap that recorded multiple sequential 1.5 GB AVI files. This file size captured six minutes of video (i.e. 10 files=60 min) at 12 frames $s^{-1}$. Each day's footage (~420 GB) was recorded onto an external hard drive connected to a desktop computer. The contents of each hard drive were then transferred to the hierarchical storage management (HSM) system at The University of Queensland. Video files stored on the HSM were then evenly distributed to local disks on 20 workstations located in the Visualization and Advanced Computing (ViSAC) laboratories at The University of Queensland. Mossiefly, a custom program developed in Matlab (The MathWorks, Inc, Natick, Mass.) was used to process videos for motion detection and tracking. This program detected and tracked movement (walking and flying separately) of individual mosquitoes and digitised the coordinates and time for each movement. The files containing data from movement detection were then analysed using Mossiestat, a program developed in Matlab that summarised the movement data captured with Mossiefly into numerical values used for statistical analysis. A total measure of activity (summation of time spent flying and walking) reported per hour was used for all subsequent statistical analysis as it was more informative than examining the variables independently.

Metabolic Rate

Closed-system respirometry was used to measure $CO_2$ production ($\dot{V}_{CO2}$) in the mosquitoes. $CO_2$ production has been shown extensively to be an accurate measure of the metabolism for small and highly aerobic organisms such as insects (Lighton, 1991; Lighton and Duncan, 2002; Van Voorhies et al., 2004). Our experiment was designed to determine whether metabolic rate was significantly different between wMelPop-infected and -uninfected mosquitoes in each of two, day time intervals lasting 4 hours. Fifteen individual mosquitoes were measured for each sex×strain×age×interval combination. These measurements were replicated 3 times. Mosquitoes were discarded after the recording interval and replaced with fresh mosquitoes from the same rearing cage.

An ADInstruments gas analyzer (ML205) and a PowerLab (85P) analog-to-digital converter connected to a computer running data acquisition software (ADInstruments, Chart 5) were used to measure $CO_2$ production from mosquitoes. Before each experiment, the gas analyser was calibrated with gas of a known $CO_2$ content. Individual mosquitoes were loaded into 25 ml syringes, mounted with a three-way valve stopcock. Before closing the three-way valve the syringe was carefully flushed with room air to remove possible $CO_2$ traces. Immediately after closing the 15 syringes, a separate syringe was filled with air and kept as a control sample for initial room air $CO_2$ concentration. After the 4 h interval, the syringes were injected into the gas analyser at 2 ml $s^{-1}$ until 5 ml of air remained. The gas concentrations for each mosquito were used to calculate mosquito metabolic rate. The dry mass of each mosquito was obtained after freezing them for 48 h at −20° C. and desiccating the tissue in a dry vacuum pump. Dry mass was measured with an electronic balance (Sartorius BP211D) to the closest 0.01 of a milligram. Mosquitoes were not weighed before metabolic rate experiments because immobilisation methods (i.e. $CO_2$ asphyxiation) may alter metabolic rates.

The following formulas based on (Bartholomew et al., 1985) were used for calculations of metabolic rates:

$$\dot{V}_{CO_2}(mlCO_2 h^{-1}) = V_a * V_b * t^{-1}$$

where $V_a$ was the increase in volume of carbon dioxide in the samples (calculated from the difference between final and initial $CO_2$ fractional concentrations), $V_b$ was the effective volume in the syringe (25 ml minus the mosquito volume, estimated as 1.01*body mass), and t was the elapsed time in hours. Due to variation in mass between male and female, mosquitoes metabolic rate was allometrically scaled using the following formula based on (Fuery et al., 1998):

$$\text{Scaled MR}(mlCO_2 h^{-1}) = ((\overline{M}/M)^{-0.75}) * \dot{V}_{CO_2}$$

where $\overline{M}$ is the mean mass of male and female mosquitoes used for each of the metabolic experiments, and M is the mass of individual mosquitoes. This formula assumes that $CO_2$ production is proportional to the $mass^{(0.75)}$ (West et al., 2002).

Statistical Analysis

Transformations (square root) of the activity measures and the scaled metabolic rate were necessary to generate normal distributions. General linear models were then constructed in Statistica Release 8 (StatSoft) for each of the sexes separately to explore the effects of age, infection status, time of day and replicate on each of the activity and metabolic rate datasets separately. T-tests were then employed to specifically test for differences in metabolic rates between infected and uninfected mosquitoes at each of the three ages.

Results

Mosquito Activity

Figure 13:
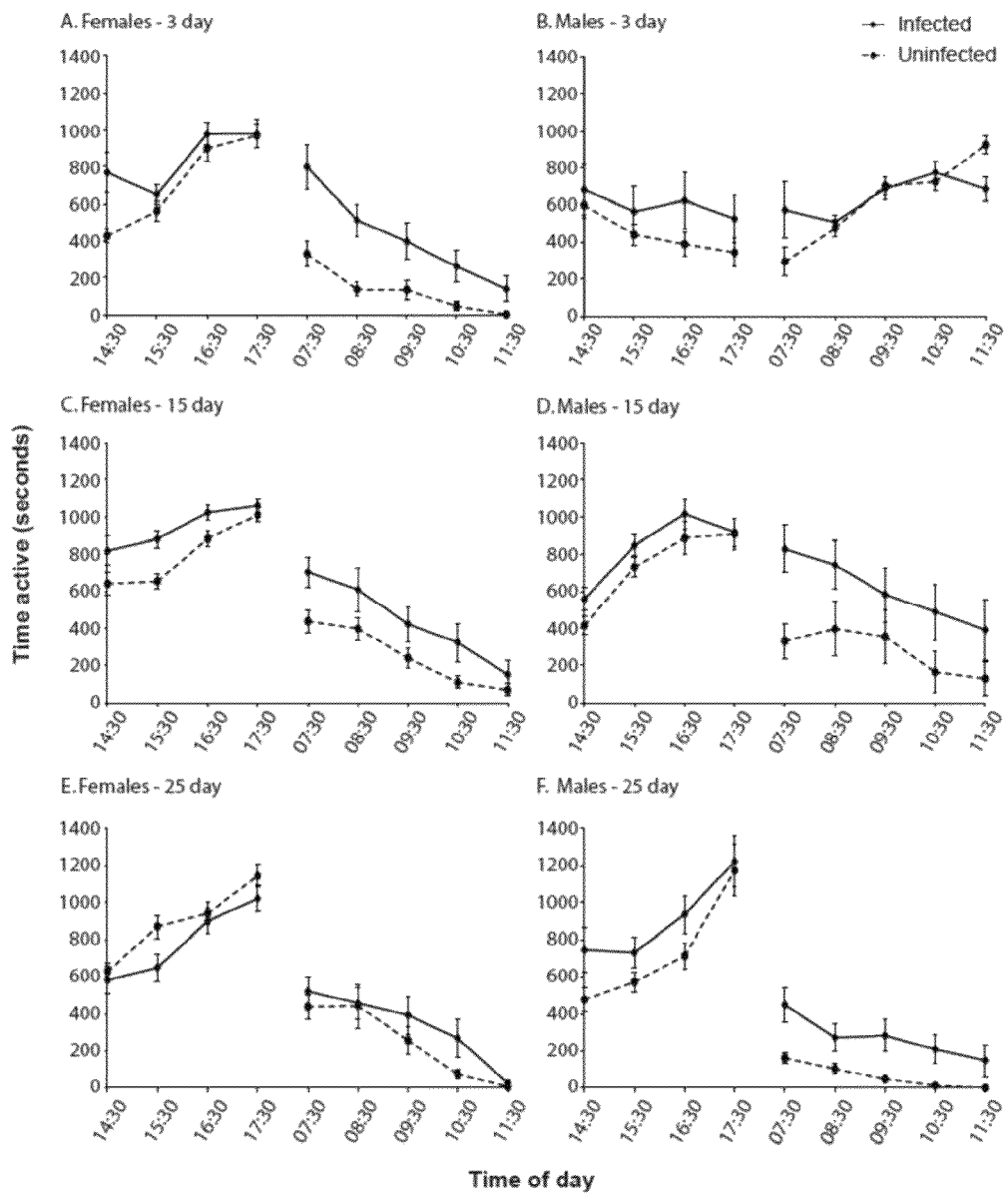
FIG. 13. Mean total time active±sem per 1 hour window for infected and uninfected males and females at 3 adult ages. Times on X-axis denote the beginning of the hour session. Lights were turned on daily at 07:00 and off at 19:00. Each point represents 10 mosquitoes×3 replicate recording days.

On average, *Wolbachia* infected individuals were more active during the day than their uninfected counterparts at each of the three adult ages examined (FIG. 13). Increases in activity were significant for both females (d.f.=1, F=54.8, P<0.0001) and males (d.f.=1, F=33.3, P<0.0001). Median increases in activity over the daytime period ranged from 1.0- to 2.5-fold higher for infected mosquitoes depending on the adult age. Age itself also played a role in mosquito activity (females: d.f.=2, F=20.7, P<0.0001, males: d.f.=2, F=13.1, P<0.0001). In general, both infected and uninfected, male and female, mosquitoes showed decreasing activity with age (FIG. 13). Only males, however, demonstrated a significant interaction between age and infection status (d.f.=2, F=5.1, P<0.01), where the increase in activity due to infection was enhanced with age (FIGS. 13B, D, &F).

Mosquito Metabolic Rate

Figure 14:
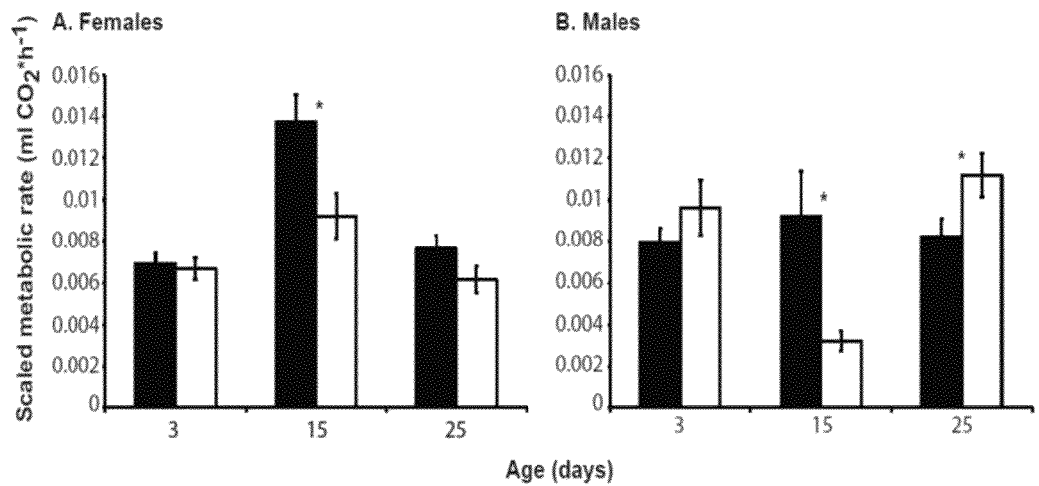
FIG. 14. Mean metabolic rate±sem based on two 4 hour windows (07:30-11:30 and 11:30-3:30) for infected (black bars) an uninfected (white bars) males and females at 3 adult ages. Each bar represents data from 15 mosquitoes×3 replicates×2 windows.

Metabolic rate was measured for separate sets of mosquitoes during two daytime windows, 07:30-11:30 and 11:30-15:30. The data from the two windows were combined after they were shown not to differ from one another using a general linear model (data not shown). In females (FIG. 14A), both infection status (d.f.=1, F=9.7, P=0.002) and age (d.f.=2, F=15.7, P<0.0001) were significant predictors of metabolic rate. On average infected females had higher metabolic rates than uninfected, with young mosquitoes showing no difference and 15 day old mosquitoes showing the greatest increase (d.f.=58, t=2.6, P<0.01). Female mosquitoes, both infected and uninfected, were most active at 15 days of age (FIG. 14A). In males, infection played a much less consistent role in metabolic rate over the ages examined (FIG. 14B). Infection alone was not a factor (d.f.=1, F=0.81, P=0.36) in determining metabolic rate, while age was statistically significant (d.f.=2, F=15.7, P<0.0001). There was, however, a significant interaction between age and infection (d.f.=2, F=16.7, P<0.0001). This interaction can be seen between 15 and 25 day old males (FIG. 14B), where at 15 days of age infected males have higher metabolic rates (d.f.=55, t=4.1, P<0.001) and at 25 days of age they have lower rates (d.f.=58, t=−2.40, P<0.05).

Example 4

Wolbachia and Virus Protection in Insects

Materials and Methods

Fly Stocks

All fly lines were maintained on standard cornmeal diet at a constant temperature of 25° C. with a 12 hour light/dark cycle. The Oregon RC (ORC) line was obtained from the Bloomington *Drosophila* stock centre at Indiana University in 2004, whereas the Oregon R (OR) and $w^{1118}$ lines have been maintained long term in the O'Neill lab. The Champetières (Champ) stock was obtained in 2005 from the *Drosophila* Genetic Resource Centre at Kyoto Institute of Technology (stock number 103403) and maintained in the Johnson lab.

*Drosophila* C virus isolate EB (Johnson and Christian, 1998) was plaque purified, passaged in *Drosophila* (DL2) cells and purified by centrifugation through a 10-40% sucrose gradient as previously described (Hedges and Johnson, 2008). The cricket paralysis virus (CrPV) (Johnson and Christian, 1996) and the Flock House virus (FHV) isolate we previously described (Johnson et al., 2001) were used in the current study. DL2 cells were infected with either CrPV or FHV and cells harvested two days post infection. Cells were lysed by two rounds of freeze thawing and lysates were clarified by centrifugation for 20 min at 5000 g. Virus was pelleted through a 20% sucrose cushion by centrifugation at 100000 g for 3 hours. Virus was resuspended in 50 mM Tris, pH 7.4, aliquoted and stored at −80° C. A fresh aliquot was thawed for each experiment.

The concentration of tissue culture infectious units (IU) of each virus preparation was
determined essentially as previously described (Scotti, 1980). Briefly, 50 µl of a suspension of DL2 cells (1×10$^6$ cells/ml) was transferred to individual wells of a flat bottomed 96 well tissue culture tray and cells were allowed to attach for at least 1 hour. A ten-fold dilution series was prepared in standard cell culture medium for titration. Each virus dilution was used to inoculate 8 wells (50 µl per well). The plates were incubated at 27° C. for 4-5 days before scoring for cytopathic effects (CPE) and the concentration of IU in the virus sample calculated as described previously (Scotti, 1980).
Survival Assays For survival assays 4-6 day old adult male *Drosophila* were infected by microinjection of virus into the upper lateral part of the abdomen. For negative controls flies were injected with PBS. Samples were injected into flies anaesthetised with carbon dioxide, using needles pulled from borosilicate glass capillaries and a pulse pressure micro-injector. Virus was diluted to a standard concentration (DCV 1.8×10$^8$ IU/ml, CrPV 1.8×10$^8$ IU/ml and 1.8×10$^8$ IU/ml FHV) in PBS and approximately 100 nl was injected into each fly. For each fly line assayed, three groups of 15 flies were injected with virus and one group of 15 flies were injected with PBS. Flies were maintained in vials at a constant temperature of 25° C. with a 12 h light/dark cycle and mortality was recorded daily. Mortality that occurred within 2 days of injection was deemed to be due to injury. Negligible mortality (<10% in all cases) was observed in negative controls (data not shown). Each experiment was repeated in triplicate. Survival curves were compared using Kaplan-Meier analysis (Statview).
Diagnosis of *Wolbachia* and DCV Infection Five flies were pooled from each fly line and genomic DNA was extracted using the previously described STE method (O'Neill et al., 1992). The DNA was PCR screened for presence of *Wolbachia* using the diagnostic wsp primer set 81F and 691R (Zhou et al., 1998) and the integrity of the DNA was confirmed using the 12S primer set 12SA1 and 12SB1 (Simon et al., 1994). All fly stocks were confirmed to be DCV free (data not shown).
Tetracycline Treatment All *Wolbachia* infected fly lines used were treated with 0.03% tetracycline (Hoffmann et al., 1986) to generate uninfected fly lines. Following the tetracycline treatment flies (designated ORCT or $w^{1118}$ T) were held for more than five generations to recover before being used for experiments.
RT-qPCR Analysis of Virus RNA concentration in flies Flies from the ORC and ORCT lines injected with DCV as described above were harvested immediately following injection (0 day time point), 2 days or 7 days post infection. Four flies were pooled, RNA extracted, random primed cDNA synthesised and the amount of DCV RNA quantified using the primers DCV-rt-fw1 5' AGGCT-GTGTTTGCGCGAAG 3' (SEQ ID NO: 9) and DCV-rt-rv1 5'AATGGCAAGCGCACACAATTA3' (SEQ ID NO: 10) as previously described (Hedges and Johnson, 2008). For each time point shown four pools flies were independently assayed.

Results

Figure 15:
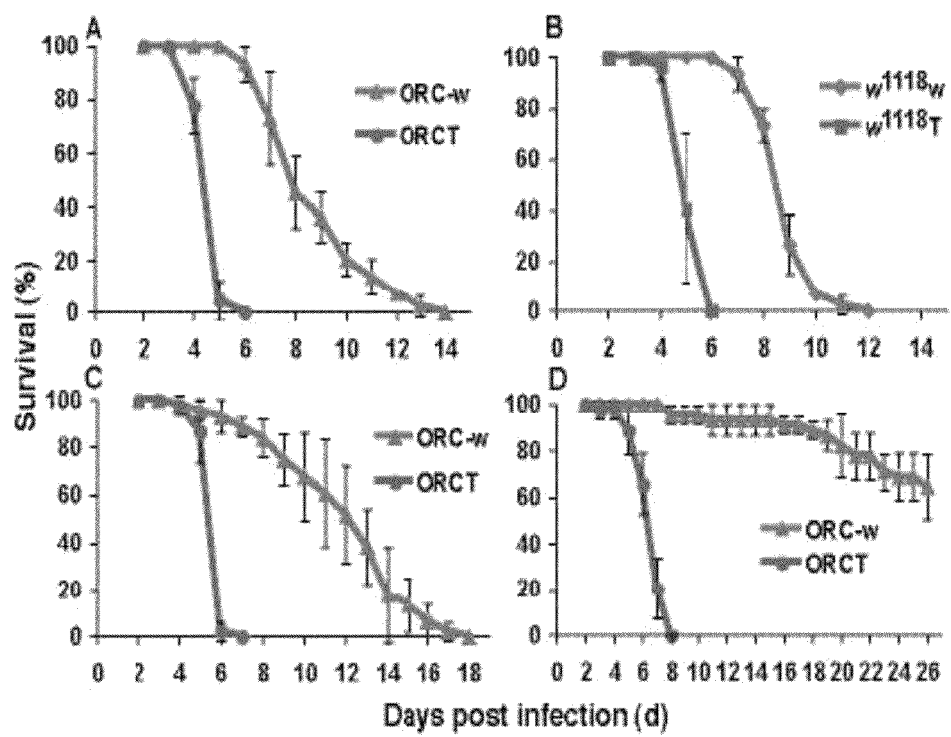
FIG. 15. Infection with *Wolbachia* protects flies from virus-induced mortality. (A) Comparison of the survival of *Wolbachia* infected (w) or uninfected Oregon RC (ORCT) flies following challenge with DCV (B) Comparison of the survival of *Wolbachia* infected (w) or uninfected (T) $w^{1118}$ flies following challenge with DCV (C) Comparison of the survival of *Wolbachia* infected (w) or uninfected Oregon RC (ORCT) flies following challenge with CrPV (D) Comparison of the survival of *Wolbachia* infected (w) or uninfected Oregon RC (ORCT) flies following challenge with FHV. For all panels the data shown represents the mean of triplicates and the bars indicate standard error. For each panel the survival curves were significantly different for *Wolbachia* infected versus uninfected flies (Kaplan-Meier analysis, $p<0.0001$ in each case).
Figure 17:
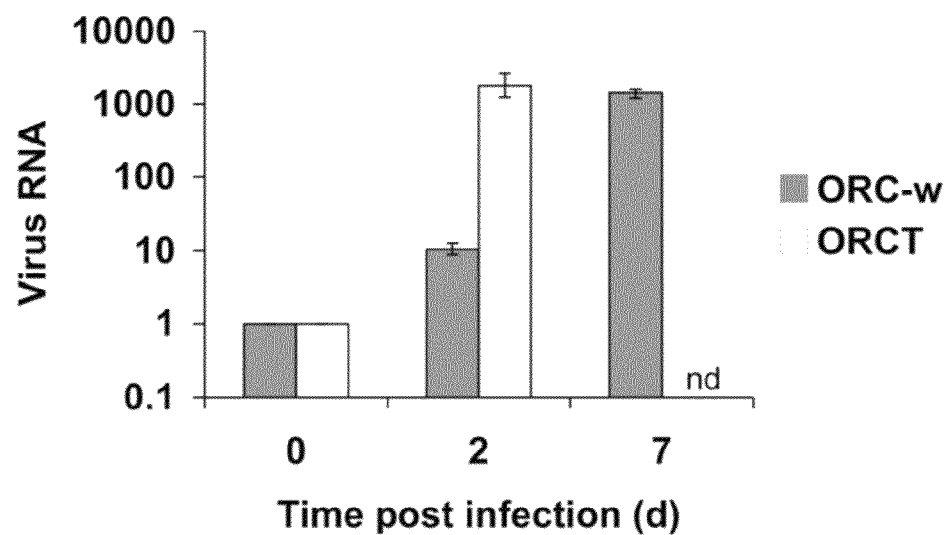
FIG. 17. Virus RNA accumulation is delayed in *Wolbachia* infected ORC flies. Infected flies were collected 0, 2 and 7 days post infection and assayed for virus RNA. Values shown are in arbitrary units and are relative to time 0 values. Data shown represents the mean of four replicates and the bars indicate standard error.

We compared the survival of flies infected with DCV in the presence or absence of *Wolbachia* infection (FIGS. 15 and 16) (Materials and Methods). In flies from the standard laboratory strain Oregon RC, *Wolbachia* infection delayed DCV-induced mortality compared to Oregon RC flies cured of *Wolbachia* infection (FIG. 15A). The delay in mortality corresponded with a delay in virus accumulation in *Wolbachia* infected flies (FIG. 17). The experiment was repeated with the fly strain $w^{1118}$ with similar results observed (FIG. 15B). The survival curves of Oregon RC and $w^{1118}$ *Wolbachia*-free flies were similar to those of two wild type laboratory populations (Champetières and Oregon R) that are naturally uninfected with *Wolbachia* (compare FIGS. 15A and 15B with FIG. 16). Oregon RC and $w^{1118}$ flies are infected with two closely related strains of *Wolbachia*, wMelCS and wMelPop, respectively (Riegler et al., 2005). These results indicate that these strains of *Wolbachia*, in different genetic backgrounds of *Drosophila*, have an antiviral effect. Two further viruses were tested using the survival bioassay; cricket paralysis virus (CrPV; Dicistroviridae) a natural *Drosophila* pathogen and Flock House virus (FHV; Nodaviridae). The latter is unrelated to DCV and CrPV and is pathogenic in adult flies (Wang et al., 2006) although natural infections have not been reported. Like DCV, both CrPV and FHV induce rapid mortality when injected into adult *Drosophila*. All, Oregon RC flies infected with *Wolbachia* and CrPV died within 17 days post infection (FIG. 15C). In contrast, the *Wolbachia*-free Oregon RC flies all died within seven days of infection.

Similarly, *Wolbachia*-free flies challenged with FHV died within 8 days of infection, whereas 26 days post infection only 35% of the *Wolbachia*-infected flies had succumbed to FHV induced mortality (FIG. 15D). These results indicate that the antiviral effect observed in *Wolbachia*-infected *Drosophila* functions to protect flies from diverse RNA viruses.

Example 5

Variation in Antiviral Protection Mediated by Different *Wolbachia* Strains in *Drosophila Simulans*

Materials and Methods

Viruses

Plaque purified DCV isolate EB (Hedges and Johnson, 2008) and FHV (Johnson et al., 2001) were propagated and purified from DL2 cells (Schneider, 1972). DL2 cells were maintained in Schneider's media supplemented with 10% FBS, 1× glutamine and 1× penstrep (Invitrogen) at 27.5° C. Cells grown in 75 cm² flasks were infected with either DCV or FHV at a low multiplicity of infection (<1) and harvested at 4-5 dpi. Cells were lysed by two rounds of freeze-thawing and cell debris removed by centrifugation at 5,000 rpm for 5 min. The virus was purified from the supernatant by pelleting through a 6 ml 10% sucrose cushion at 27,000 rpm at 12° C. for 3 hours in a SW28 swing bucket rotor (Beckman). The resuspended virus was layered onto a continuous 10-40% w/v sucrose gradient and centrifuged at 27,000 rpm at 12° C. for 3 hours in a SW41 swing bucket rotor (Beckman). The virus-containing fractions were harvested, diluted in 50 mM Tris pH 7.4 and virus was pelleted by centrifugation at 27,000 rpm, 12° C. for 3 hours. The virus was resuspended in 50 mM Tris pH 7.4 at 4° C. overnight, aliquoted and stored at −20° C. The concentration of tissue culture infectious units (IU) of each virus preparation was determined by replicate $TCID_{50}$ analysis on two separate frozen aliquots, as previously described (see Example 4).

Flies and *Wolbachia*

All *Wolbachia* infected fly lines were obtained from the culture collection in the O'Neill lab and were maintained on standard cornmeal diet at a constant temperature of 25° C. with a 12-hour light/dark cycle. The *D. simulans* fly line Me29 is infected with wMel. The wMel infection was established by injection of *Wolbachia* containing cytoplasm from *D. melanogaster* Wien 5 embryos into *D. simulans* NHaTC embryos (Poinsot et al., 1998). The other *D. simulans* lines are naturally infected with *Wolbachia* strains as previously described and are listed in Table 2 (Hoffman et al., 1986; Mercot and Poinsot, 1998; O'Neill and Karr, 1990; and Hoffman et al., 1996).

Preparation of *Wolbachia*- and Virus-free Fly Lines

Virus-free populations of each of the *Wolbachia* containing fly line were prepared essentially as previously described (Brun and Plus, 1980). Briefly, flies were aged for at least 20 days, transferred to fresh media (supplemented with dry yeast) and allowed to lay eggs for up to 16 hours. The eggs were collected from the surface of the media and treated for 4 minutes in 1.7% (w/v) sodium hypochlorite solution to remove the chorion. After treatment the eggs were thoroughly rinsed with water, transferred to moist filter paper and placed on fresh virus-free media. Virus-free flies were maintained separately from untreated stocks.

To generate fly lines free of *Wolbachia* each virus-free *Wolbachia* infected fly line was treated with 0.03% tetracycline (Hoffman et al., 1986). Following the tetracycline treatment flies were held for more than four generations to recover before being used for experiments.

Survival Bioassays

*Drosophila* were infected with DCV, FHV or mock infected by microinjection of virus or PBS into the upper lateral part of the abdomen. Samples were injected using needles pulled from borosilicate glass capillaries and a pulse pressure micro-injector into 4-7 day old male flies that were anaesthetised with carbon dioxide. For each fly line assayed, three groups of 15 flies were injected with virus and one group of 15 flies were injected with PBS. After injection flies were maintained in vials at a constant temperature of 25° C. with a 12 h light/dark cycle and mortality was recorded daily. Mortality that occurred within one day of injection was deemed to be due to injury. Each experiment was replicated using independent cohorts of flies. Survival curves were compared using Kaplan-Meier analysis and log-rank statistics reported (GraphPad Prism). For each assay described in this paper a fresh aliquot of either DCV or FHV was defrosted and diluted to $1 \times 10^8$ IU/ml before use.

Virus Accumulation Assays

The accumulation of infectious DCV particles in both *Wolbachia* infected and uninfected flies was measured. For each of the five fly lines, groups of flies with and without *Wolbachia* were injected with DCV as for survival bioassays. At designated times post injection, two pools of four live DCV injected flies were collected and frozen at −20° C. Flies from all *Wolbachia* infected and uninfected fly lines were collected at 2 dpi. For Me29, DSR and CO flies infected with *Wolbachia* samples were also collected at 10 days post injection; for N7NO and DSH containing *Wolbachia* and all tet-treated lines there were not enough live flies remaining at 10 days for collection. For CO-*Wolbachia* flies an additional collection was included at 30 dpi.

Each pool of four flies was homogenised in 100 µl of PBS with two 3 mm beads (Sigma-Aldrich) using a Mini Bead-Beater-96 (Biospec Products) for 60 seconds. The homogenates were clarified by centrifuging at 14 K for 8 minutes. The virus-containing supernatant was aliquoted and stored at −20° C. Virus titre was determined using the $TCID_{50}$ assay as previously described (see Example 4). The two replicates for each fly population were assayed on different days to control for between-day variation in $TCID_{50}$ assays. Statistical analysis of the data was done using unpaired t tests to compare the geometric means of the duplicate samples between flies of each line with and without *Wolbachia* at 2 dpi (GraphPad Prism).

Analysis of *Wolbachia* Density

For each fly line 200 eggs were collected and incubated on fresh food with a constant temperature of 25° C. for 10 days. Freshly emerged flies were collected for 8 hours, aged to 4 days old and then five male flies from a single collection were pooled. For each fly line a total of 10 pools of flies were collected from independent bottles and the DNA extracted using a DNeasy Blood and Tissue Kit as per the Manufacturer's instructions (Qiagen). The relative ratio of *Wolbachia* to fly genomic DNA was determined by quantitative PCR. Each 10 µL qPCR reaction included 5 µL of Sybr Green qPCR Supermix-UDG (Invitrogen), 1 µL of DNA template and 1 µM each of the forward and reverse primers. Primers for *Wolbachia* were designed from an alignment of the sequence of the WSP genes from all five *Wolbachia* strains (wspFQALL 5' GCATTTGGTTAYAAAATGGACGA 3' (SEQ ID NO: 11) and wspRQALL 5' GGAGTGATAG-GCATATCTTCAAT 3') (SEQ ID NO: 12) and for the host gene RPS17 (Dmel.rps17F 5' CACTCCCAGGTGCGTGG-TAT 3' (SEQ ID NO: 13) and Dmel.rps17R 5' GGAGACG- GCCGGGACGTAGT 3' (SEQ ID NO: 14)). Reactions were done in duplicate in a Rotor-gene thermal cycler (Corbett Life Sciences) with the following conditions: one cycle of 50° C. 2 min, 95° C. 2 min, followed by 40 cycles of 95° C. 5 sec, 60° C. 5 sec, 72° C. 10 sec. A third technical replicate was done where necessary and DNA extracted from flies without *Wolbachia* was used as a negative control. Ratios were calculated in Qgene and statistical analysis included Mann-Whitney t test to compare differences of the means.

Accession Numbers

EF423761 wsp wRi; DQ235409 wsp wAu; AF020074 wsp wNo; AF020073 wsp wHa; NM_079278 RPS17

Results

*Wolbachia* Strain wMel can Protect *D. simulans* from DCV

Figure 18:
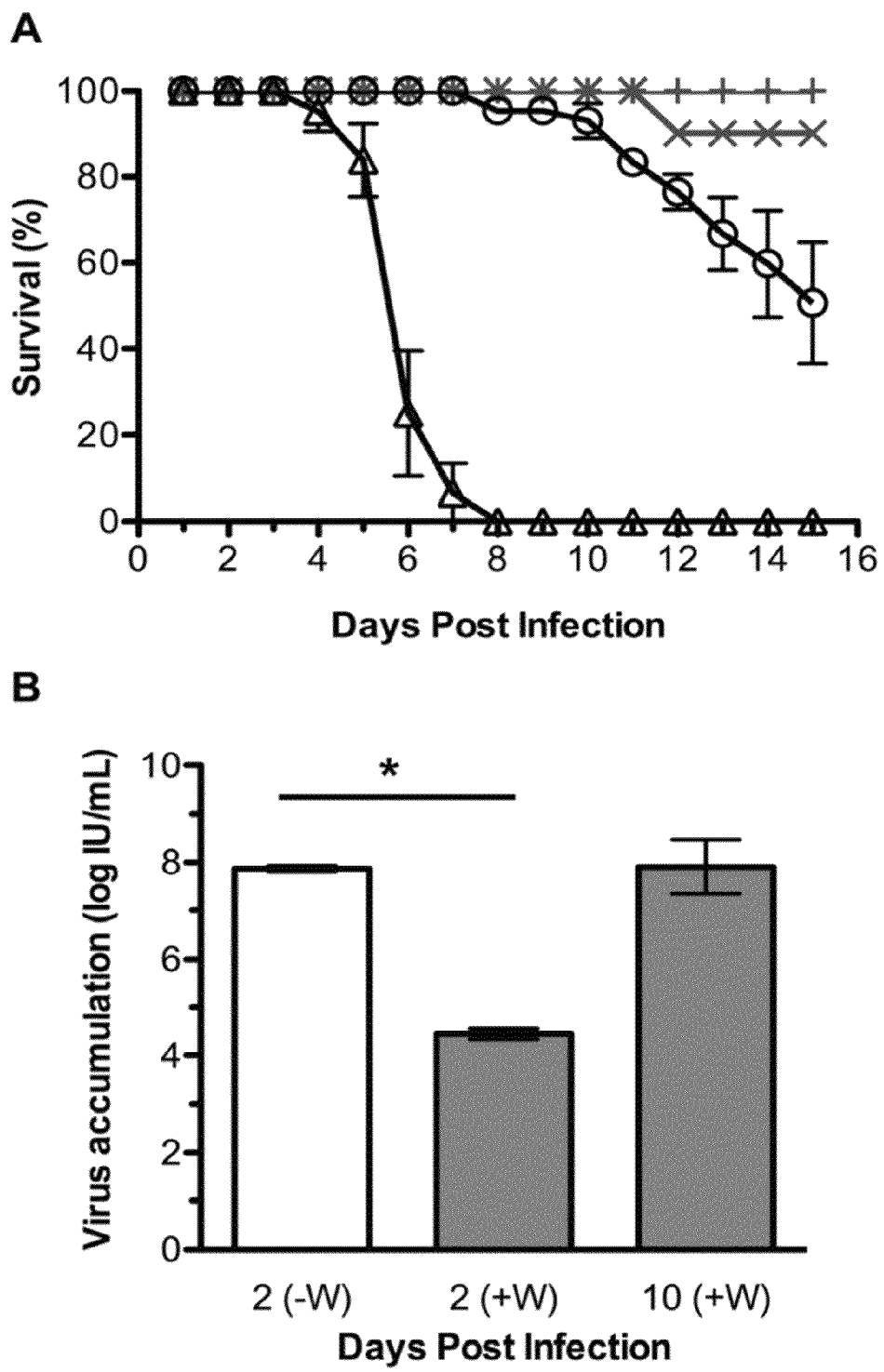
FIG. 18. *Wolbachia* strain wMel provides antiviral protection in *D. simulans*. A. Graph shows survival of flies infected with DCV (black line) or mock infected (grey line). wMel-infected (circle and plus sign) or uninfected (triangle and cross) flies. The survival of DCV infected flies with and without *Wolbachia* is significantly different ($p<0.0001$). Error bars represent SEM calculated from three replicate vials. This is a representative experiment which was repeated twice more with similar results. B. Graph showing accumulation of infectious DCV in wMel infected (grey bars) or uninfected (white bar) flies. Bars represent means from two replicates with SEM shown, and * indicates a significant difference between the means of day 2 samples ($p<0.05$, unpaired t test).

*Wolbachia* strains closely related to wMel have previously been shown to protect their natural host *D. melanogaster* from accumulation of DCV particles and DCV-induced mortality (Teixeira et al., 2008; see also Example 4). To establish whether wMel can protect *D. simulans* from DCV, we assayed Me29, a *D. simulans* line that was transinfected with wMel (Poinsot et al., 1998) (Table 2). Me29 flies infected with wMel and the genetically paired population that had been cured of *Wolbachia* infection were challenged with DCV and mortality was recorded for 15 days (FIG. 18A). For flies both with and without *Wolbachia* the mortality in PBS injected controls was negligible. All DCV injected wMel-free flies died by 8 days post infection (dpi), with a median survival time of 6 days. In contrast, at 15 dpi about 50% of wMel infected flies remained alive. These results indicate that the presence of wMel mediates a significant decrease in DCV induced mortality in Me29 flies.

The accumulation of infectious DCV particles was assayed in Me29 flies with and without wMel. The titre of infectious virus in homogenates from flies collected 2 dpi was significantly different in flies with and without wMel (p<0.002; FIG. 18B). The titre of virus in flies without *Wolbachia* was estimated to be about 2600-fold greater than in Me29 flies infected with wMel. By 10 dpi there were no surviving *Wolbachia*-free flies and the virus titre in the surviving wMel infected flies had increased to a level similar to that of *Wolbachia*-free flies at 2 dpi. This indicates that the presence of wMel in Me29 flies delays rather than prevents DCV accumulation.

*D. simulans Wolbachia* Strains and Protection from DCV Induced Mortality

Figure 19:
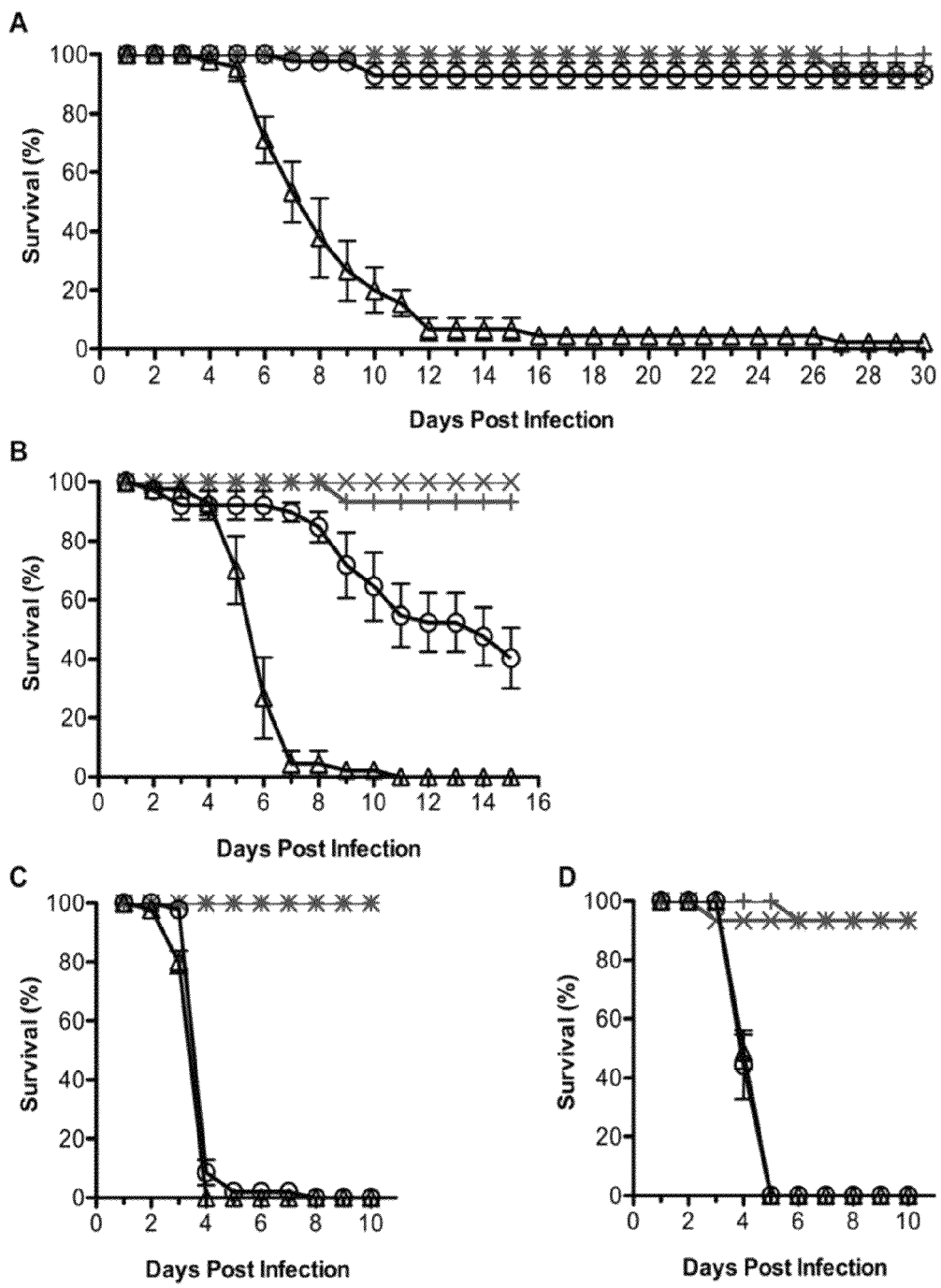
FIG. 19. Antiviral protection of different *Wolbachia* strains in *D. simulans*. Graphs show survival of flies infected by wAu (A), wRi (B), wHa (C), and wNo (D) challenged with DCV (black line) or mock infected (grey line). Flies with *Wolbachia* (circle and plus sign) and without *Wolbachia* (triangle and cross). Error bars represent SEM calculated from three replicates. The survival of DCV infected flies with and without *Wolbachia* is significantly different for wAu ($p<0.0001$), wRi ($p<0.0001$), and wHa ($p<0.01$), using log rank test on Kaplan-Meier curves. Experiments were replicated on at least two additional independent cohorts of flies, and the results for all respective replicates of experiments shown in panel A, B and D were similar, however the replicates for panel C varied (see results in Example 5).

*D. simulans* populations are naturally infected with a range of *Wolbachia* strains. To analyse whether diverse strains could protect from DCV induced mortality we assayed four *D. simulans* lines CO, DSR, DSH and N7NO, which are naturally infected with wAu, wRi, wHa and wNo, respectively (Table 2). Each of the four fly lines was treated with tetracycline to produce a genetically paired line without *Wolbachia* infection. Flies with and without *Wolbachia* were challenged by injection with DCV or mock infected with PBS (FIG. 19). In all cases less than 10% mortality occurred in the mock-infected flies, indicating that in the absence of virus fly survival was stable over the course of the experiments. The CO flies without *Wolbachia* had a median survival time of 8 days following DCV injection (FIG. 19A). Strikingly, the wAu-infected CO flies survived DCV infection; more than 90% were alive when the experiment was terminated at 30 dpi. The wRi-infected DSR flies had significantly better survival (p<0.0001) than *Wolbachia*-free DSR flies (FIG. 19B). The median survival times following DCV infection were 14 dpi as compared to 6 dpi for flies with and without wRi, respectively. Thus presence of either wAu or wRi in *D. simulans* can mitigate DCV-induced mortality.

Not all *Wolbachia* strains protected flies from DCV induced mortality. The median survival time of DSH and N7NO flies challenged with DCV was 4 days regardless of *Wolbachia* infection status for fly lines infected by wHa or wNo, respectively (FIGS. 19C and 19D). While there was a small but statistically significant (p=0.001) difference between the survival curves for the DSH flies with and without wHa infection for the representative experiment shown in FIG. 19C, a significant difference was evident in only 2 out of 4 experiments replicated on independent cohorts of flies (data not shown). Taken together, the minor difference in survival and non-reproducible nature of the result suggests that it is unlikely that this difference is biologically relevant, and as such we interpret the results as indicating that there is no protection against DCV induced mortality in the DSH flies infected with wHa. There was no difference between the survival curves of N7NO flies with and without wNo infection (p=0.7). To investigate whether protection would be evident for these lines challenged with reduced amounts of virus we decreased the concentration of DCV injected by 10- or 100-fold. Even at these lower doses of virus no *Wolbachia*-mediated antiviral protection was observed in DSH and N7NO flies (data not shown).

Accumulation of DCV in Flies with and without *Wolbachia*

Figure 20:
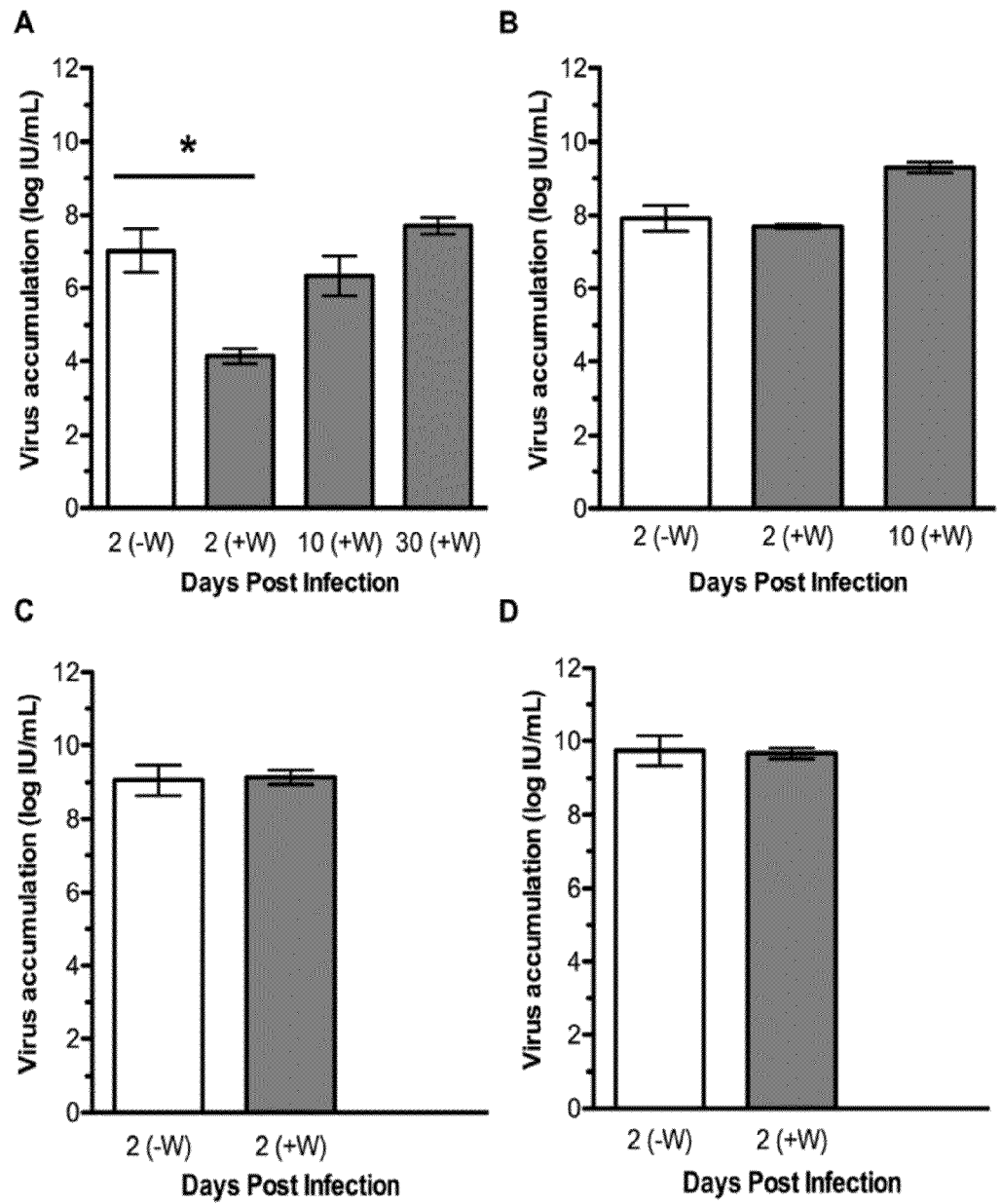
FIG. 20. The effect of different *Wolbachia* strains on the accumulation of DCV in *D. simulans*. Graphs show accumulation of infectious DCV in flies with (grey bar) or without (white bar) wAu (A), wRi (B), wHa (C), and wNo (D). Bars represent means from two replicates with SEM shown, and * indicates a significant difference between the means of day 2 samples ($p<0.05$, unpaired t test).

DCV accumulation was assayed in each *D. simulans* line in the presence or absence of *Wolbachia* (FIG. 20). DCV infected flies were assayed at 2 dpi and the DCV titre was compared for each fly line with and without *Wolbachia* infection. The average DCV titre was approximately 800-fold lower in CO flies infected with wAu compared to paired *Wolbachia*-free flies, and an unpaired t test showed this to be a significant difference (p<0.05; FIG. 20A). Interestingly, although wAu infected flies survived DCV infection (FIG. 19A), virus continued to accumulate beyond 2 dpi and high titres of DCV were observed in wAu-infected flies harvested at both 10 and 30 dpi (FIG. 20A). This shows that these flies did not clear the virus infection. The titre of DCV was similar when comparing flies with and without *Wolbachia* at 2 dpi for each of the three other fly lines assayed (FIG. 20B-D).

*D. simulans Wolbachia* Strains and Protection from FHV Induced Mortality

Figure 21:
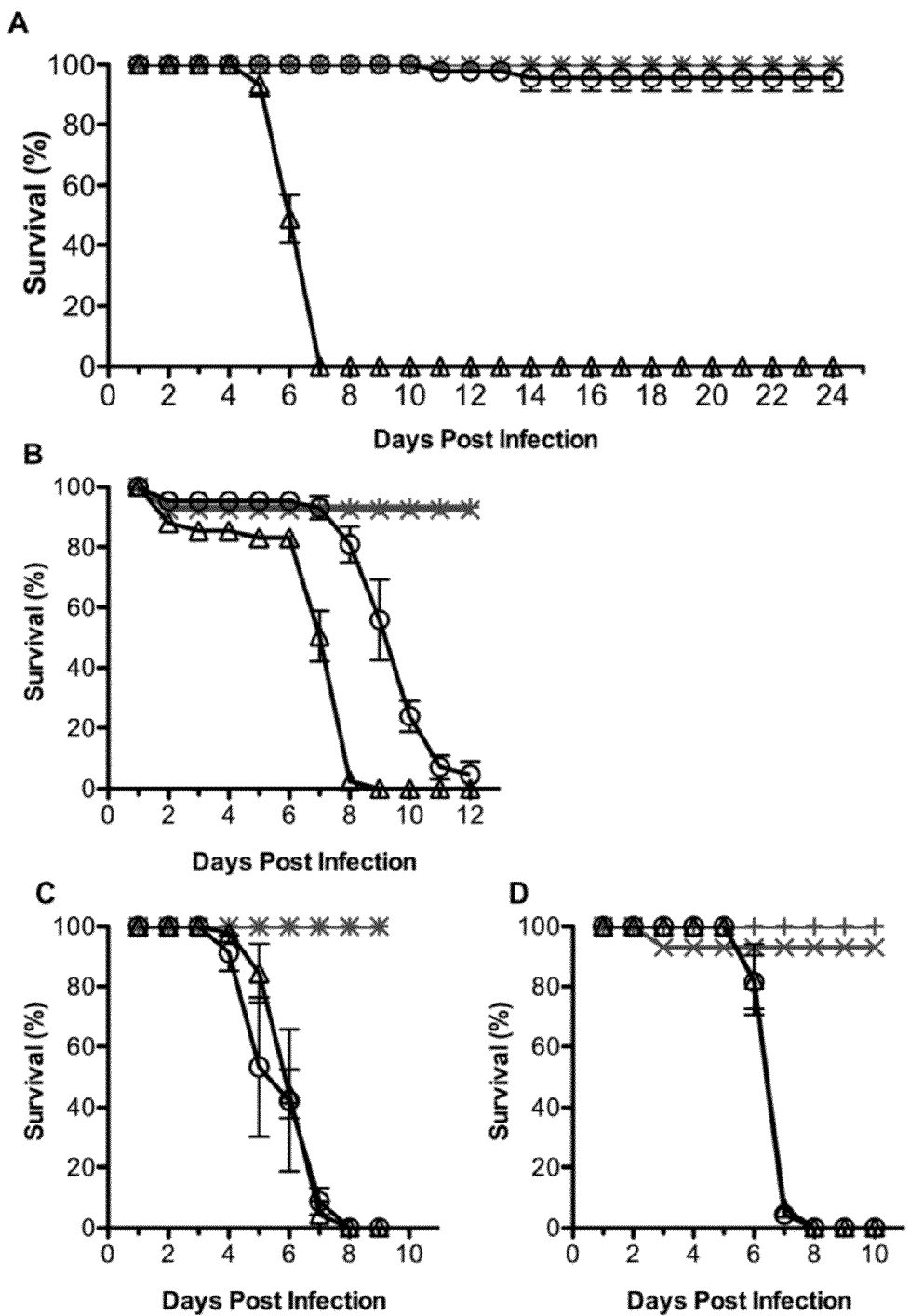
FIG. 21. The effect of different *Wolbachia* strains on the accumulation of FHV in *D. simulans*. Graphs show survival of flies infected by wAu (A), wRi (B), wHa (C), and wNo (D) challenged with FHV (black line) or mock infected (grey line). *Wolbachia* infected (circle and plus sign) and uninfected (triangle and cross) flies. Error bars represent SEM calculated from three replicates. The survival of FHV infected flies with and without *Wolbachia* is significantly different for wAu and wRi ($p<0.0001$, log rank test on Kaplan-Meier curves). For each fly line a similar result was recorded in a replicate experiment.

Having identified that some but not all *Wolbachia* strains mediate protection against DCV in the *D. simulans* lines tested, we next investigated whether antiviral protection was consistent across different viruses. Flies with and without *Wolbachia* were challenged by injection with FHV or mock infected with PBS (FIG. 21). In all cases mortality in the mock-infected control flies was negligible. The CO flies without *Wolbachia* infection reached 100% mortality within 7 days of injection with FHV (FIG. 21A). Similar to challenge with DCV the wAu-infected flies survived FHV infection; more than 90% were alive when the experiment was terminated at 24 dpi. The wRi-infected DSR flies had significantly better survival (p<0.0001) than *Wolbachia*-free DSR flies (FIG. 21B). The median survival times or DSR flies challenged with FHV were 10 days as compared to 7 days with and without wRi, respectively. Thus median time to death was reduced in both DCV and FHV infections for wRi-infected DSR flies. No virus-induced mortality was observed in wAu-infected CO flies for either virus.

Not all of the fly lines were protected from FHV-induced mortality by *Wolbachia* infection. The median survival time of DSH flies challenged with FHV was 6 days regardless of the presence or absence of wHa (FIG. 21C) and there was no significant difference in the survival curves (p=0.4). For the N7NO line there was no difference between the survival curves with and without wNo infection (p=0.5; FIG. 21D).

Wolbachia Density in Fly Lines

Figure 22:
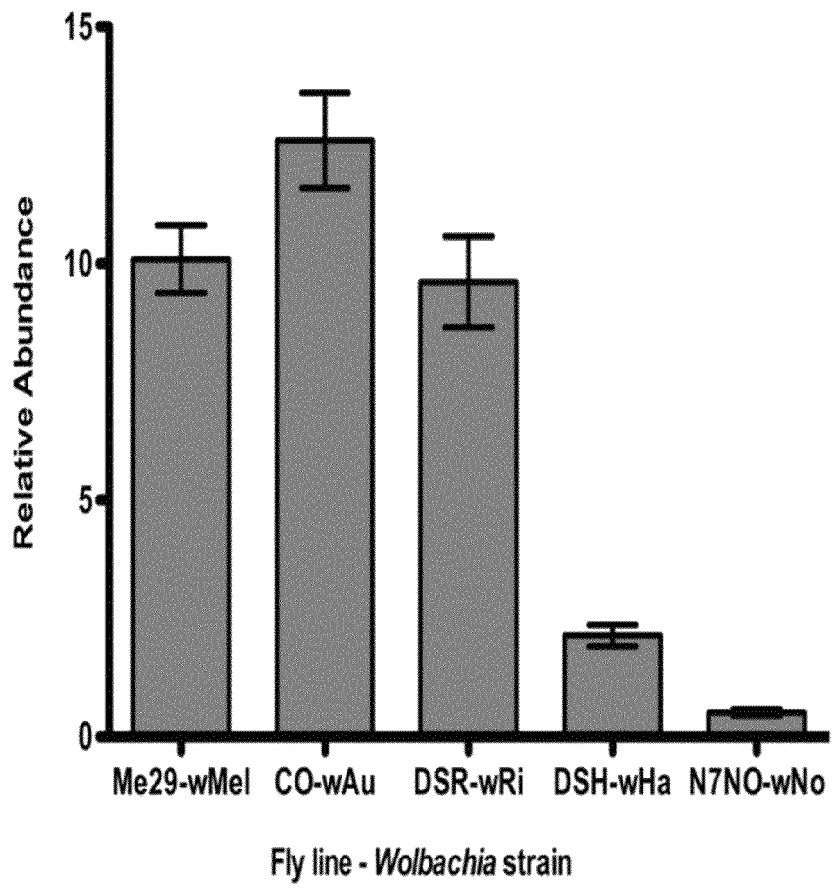
FIG. 22. Relative-density of *Wolbachia* strains in *D. simulans*. For each fly line the graph shows the relative abundance of *Wolbachia* to host genomic DNA estimated using quantitative PCR. Bars represent the mean of 10 replicates and error bars are SEM.

To investigate whether virus protection correlated with the density of the *Wolbachia* in the fly lines, we utilized quantitative PCR to determine *Wolbachia* density from pools of 5 male flies from each fly line. Estimates of abundance for a single copy *Wolbachia* gene were determined and then normalized against abundance of a single copy host gene to determine relative abundance of *Wolbachia* (FIG. 22). The three *Wolbachia* strains (wMel, wRi and wAu) that gave strong antiviral protection in the *D. simulans* lines, were significantly more abundant in these flies than the strains that gave no protection (wHa and wNo).

Dengue Interference by wMel and wMelPop in Mosquitoes

As shown in FIG. 54, dengue virus interference is generated by both wMel and wMelPop-CLA in mosquitoes.

Example 6

A *Wolbachia* Symbiont in *Aedes Aegypti* Limits Infection with Dengue, Chikungunya and *Plasmodium*

Materials and Methods

Mosquitoes

Five different *A. aegypti* lines were used including the original inbred wMelPop-CLA infected line (PGYP1) and its tetracycline-cured counterpart PGYP1.tet (see Example 2). A genetically diverse line derived from PGYP 1, named PGYP1.out was generated by backcrossing PGYP1 for three generations to F1 males of 52 independent field-collected isofemale lines from Cairns, Australia. A further two generations of backcrossing were conducted with F2 field-collected material before the colony was used in experiments. This backcrossing scheme is expected to replace 96.9% of the original inbred genotype. A tetracycline-cured counterpart (PGYP1.out.tet, −Wolb) was generated by antibiotic treatment of backcrossed adults, followed by two generations of recovery and recolonization with gut bacteria as previously described (see Example 2). A genetically diverse wild type line was also generated at the same time from field-collected material sourced from 245 ovitraps across seven suburbs of Cairns, Australia in late 2008 and named Cairns3. For the malaria experiments, a susceptible *A. fluviatilis* strain (Rodrigues et al., 2008) was used in parallel with PGYP1.out (+Wolb) and PGYP1.out.tet (−Wolb) *A. aegypti* mosquitoes. Insects were kept in a controlled environment insectary at 25 C, ~80% RH and a 12 hour light regime. Larvae were maintained with fish food pellets (Tetramin, Tetra) and adults were offered 10% sucrose solution, ad libitum. Adult females were bloodfed on human volunteers for egg production. Three to five day old female mosquitoes were used for the DENV and malaria infection experiments. Seven day old females were used for the CHIKV experiments.

Viruses

Dengue Virus

Dengue virus serotype 2 (DENV-2) (92T) was isolated from human serum collected from a patient from Townsville, Australia, in 1992. Virus stocks were passaged five times in *Aedes albopictus* cell line (C6/36) grown in RPMI 1640 medium supplemented with 10% fetal calf serum (FCS), penicillin (100 µg/ml), streptomycin (100 µg/ml), and 1× glutamax (Invitrogen), and maintained at 28° C. Supernatants were collected 5 days after infection, separated into 0.5 ml aliquots, and then frozen at −80° C. Virus used in microinjection experiments was obtained from thawed stocks of above and had a titer of 107.6 CCID50 per ml. To prepare the DENV-2 for oral feeding, the frozen virus stock was passaged once more through C6/36 cells and the supernatant was harvested at 5 days and then mixed directly with blood to formulate a bloodmeal for feeding. Virus solution with higher titer (108.85 CCID50/ml) was obtained by harvesting the viral supernatant and the intracellular virus from cell lysates.

Chikungunya Virus

CHIKV strain 06113879, isolated from a viremic traveler returning from Mauritius to Victoria, Australia in 2006 was provided by the Victorian Infectious Diseases Research Laboratory, Melbourne, Australia. Cultures were grown at 37° C. in Vero (African green monkey kidney) cells for 4 days before the supernatant was harvested and frozen at −80° C. This CHIKV stock was passaged once more in Vero cells and the virus was concentrated from 1.8 L of infected culture supernatant via ultracentrifugation at 10 000 g for 17 hrs at 4° C. Pelleted virus was resuspended in 20 ml of Opti-MEM® reduced serum medium (Gibco BRED, Invitrogen, California) supplemented with 10% FCS before aliquots of the prepared virus were frozen at −80° C. The stock concentration had a final viral titer of 108.0 CCID50/ml.

Exposure of Mosquitoes to Viruses

Intrathoracic Injection with DENV-2

Female mosquitoes were briefly anesthetized with $CO_2$ and placed on a glass plate over ice. Insects were handled with forceps under a dissecting scope and injected into their thorax (pleural membrane) with a pulled glass capillary and a hand-held microinjector (Nanoject II, Drummond Sci.). Sixty-nine nanoliters of DENV-2 stock was injected into each mosquito, which corresponds to approx. 2,750 virus particles/mosquito. After injection mosquitoes were transferred to 1 L plastic cages within polystyrene boxes and these boxes were maintained inside an environmentally controlled incubator 12:12 (L:D) h, 27° C. and 70% RH. Sucrose solution and apple slices were provided on top of each cage. Mosquitoes were collected from each cage 5 and 14 days after infection and 5 dpi (days postinfection) samples were dissected into abdomen and thorax plus head. Samples were placed on dry ice and then transferred to −80° C. until RNA extraction (see below). Fourteen days after thoracic injection eight mosquitoes were collected from each cage, briefly anesthetized with CO2 and placed on a glass plate over ice. Wings and legs were removed with forceps and their mouthparts were introduced into a 1 cm piece of polypropylene tubing (0.61×0.28 mm, Microtube Extrusions, NSW, Australia) filled with light mineral oil (Novak et al., 1995). Females were allowed to salivate into these capillaries for 5 minutes at room temperature, and then the capillaries were rinsed into 20 µl of fetal calf serum with a Hamilton syringe. Samples were centrifuged at 14,000 g for 2 minutes and kept frozen (−80° C.) for further virus detection using a cell culture enzyme immunoassay (CCEIA). Mosquito whole bodies were frozen on dry ice and kept at −80° C. for quantitative PCR virus detection.

Oral Feeding with DENV-2 and CHIKV

Mosquitoes were starved for 24 hrs and then transferred to 1 L or 2.5 L plastic feeding containers. Prior to feeding, DENV-2 was harvested from C6/36 cell culture supernatant and diluted 1:5 in defibrinated sheep's blood. For the CHIKV experiments, frozen aliquots of stock virus were rapidly thawed, and diluted in washed defibrinated sheep blood and 1% sucrose. Blood-virus mixtures were maintained at 37° C. for 1 h and 4 h for DENV-2 and CHIKV, respectively, using membrane feeders (Rutledge et al., 1964) and covered with a porcine intestine as the membrane. After feeding, mosquitoes were anesthetized using $CO_2$ and partially and non-engorged mosquitoes were discarded. Fully engorged mosquitoes were maintained on a 15% sucrose solution at 12:12 (L:D) h, 27-28° C. and 70% RH. To determine DENV-2 infection and dissemination rates, up to 40 mosquitoes were processed separately at 7 and 14 d post-exposure. To follow the replication and dissemination of CHIKV, 10-30 mosquitoes were processed on days 0, 2, 4, 7, 10 and 14 post-exposure. Mosquitoes were anesthetized using $CO_2$, and the legs (for DENV-2) and legs and wings (for CHIKV) from each mosquito were removed, and these and the remaining body and head were stored separately at −80° C. Samples were processed using the CCEIA method (DENV-2) or qRT-PCR (CHIKV) described below. Differences in the frequency of DENV-2 infection and dissemination between mosquito lines were analyzed using chisquare goodness of fit tests after the 7 or 14 d extrinsic incubation period for DENV-2 and at 14 d for CHIKV (Zar, 1999).

Cell Culture Enzyme Immunoassays

Titration of DENV-2 and CHIKV stocks and blood/virus mixtures was performed using a CCEIA method similar to that previously described (Broom et al., 1998). For DENV-2, C6/36 cell monolayers (60-90% confluent) in 96-well plates were inoculated with 50 μl/well of virus dilutions and plates were incubated at 28° C. with 5% $CO_2$ for 5 d. Cell monolayers then were fixed and examined for DENV-2 antigens using a cocktail of *flavivirus* cross-reactive monoclonal antibodies (4G4 and 4G2) (Hall et al., 1991). For CHIKV, all titrations were performed in Vero cells, which were incubated at 37° C. with 5% CO2. After 7 d plates were examined for cytopathic effect (CPE), which was confirmed using the CCEIA and the broadly reactive alphavirus monoclonal antibody, B10.

*Plasmodium gallinaceum*

Two to three day-old White Leghorn chickens were infected through intraperitoneal or intradermal injection of *Plasmodium gallinaceum* 8A strain parasitized blood (Rodrigues et al., 2008). Parasitemia was determined every other day through Giemsa-stained blood smears. Ten microscopic fields were examined under immersion oil to count one hundred red blood cells and determine the ratio of infected cells. Presence of gametocytes and rising parasitemia was ensured in order to enhance the chance of mosquito infection. Before infection mosquitoes were deprived of sugar solution overnight and on the next morning chickens were placed on top of the cages and mosquitoes were fed for about 45 minutes. Only bloodfed female mosquitoes were kept for further observations. Four independent experiments were performed with independent cohorts. Seven days after bloodfeeding mosquitoes had their midguts dissected in 1×PBS and after staining the midguts with 0.2% Mercurochrome solution oocysts were counted under a microscope (DIC, 100×). Fifteen days after infection mosquitoes were collected and DNA was extracted (Qiagen Blood & Tissue kit) for *Plasmodium* detection. For *P. gallinaceum* detection around 1 ng of genomic DNA was used in quantitative PCR reactions as described below. Primers for the *Plasmodium* spp. 18S ssu rRNA gene (Schneider and Shahabuddin, 2000) were used for the parasite sequence amplification and *A. aegypti* Actin primers were used as a host control gene (see primer sequences in Table 6). Analyses were performed with qGENE (Joehanes and Nelson, 2008) and Mann Whitney-U tests (STATISTICA V8, StatSoft, Inc.) to compare relative abundance between lines.

Quantitative DENY PCR Analysis

Individual frozen mosquito whole bodies or body parts were placed into 2 ml screw cap vials with a glass bead (2 mm diameter, Sigma-Aldrich). 200 μl of Trizol (Invitrogen) was added and the sample homogenized for 150 s using a Mini BeadBeater (Biospec Products). Tubes were incubated at room temperature for 5 min, 40 μl of chloroform was added to each tube and samples were thoroughly vortexed for 10 s. Tubes were centrifuged for 15 min at 14,000 g at 4° C. and the supernatant containing the RNA was transferred to new tubes. RNA was precipitated by adding 40 μl of isopropanol and incubated at −20° C. overnight. Samples were centrifuged at 12,000 g for 10 min at 4° C. to pellet the RNA. Pellets were washed with 200 μL of 70% ethanol and after centrifugation (7,500×g for 5 min at 4° C.) ethanol was removed and pellets were dried for 10 min in a fume hood. RNA was resuspended in 25 μL of RNAse-free milli-Q water and tubes were incubated for 10 min at 56° C. Samples were maintained at −80° C. until further analysis. cDNA synthesis was based on the protocol described by Richardson (Richardson et al., 2006), which allowed us to determine both the genomic (+RNA) and replicative (anti-genomic) virus forms (−RNA). Briefly, 0.5 μg of each RNA (2 μg for saliva samples) was mixed with 0.625 μM of either the DENV-2 NS5 forward or reverse primer (see Table 6) plus 0.2 mM dNTPs in separate cDNA reactions. Samples were incubated at 86° C. for 15 min and 5 min on ice, then 5× first strand buffer and 100U of Superscript III (Invitrogen) was added to a total volume of 20 μl. Samples were incubated at 25° C. for 10 min, followed by 42° C. for 50 min and 10 min at 95° C. to inactivate the transcriptase. Negative controls (no template) were included in each reaction. For DENV-2 detection, cDNA samples were diluted 1:10 with milli-Q water. The qPCR reaction consisted of 2 μl of the diluted cDNAs, 5 μl of Sybr Green mix (Invitrogen) and 1 μM of each primer (see above), in 10 μl total volume. Reactions were performed in duplicate in a Rotor-gene thermal cycler (Corbett Life Sciences) with the following conditions: 50° C. 2 min, 95° C. 2 min, 45 cycles (95° C. 5 s, 60° C. 5 s, 72° C. 10 s) followed by the melting curve (68° C. to 95° C.). Melting curves for each sample were analyzed after each run to check specificity. A standard curve was created by cloning the DENV-2 NS5 fragment into pGEM®T-Easy (Promega). After linearization with Pst I the plasmid was serially diluted into known concentrations and run in parallel, in order to determine the absolute number of DENV-2 copies contained in each sample. Mann-Whitney U tests were employed (STATISTICA V8, StatSoft, Inc.) to examine the effect of *Wolbachia* infection on dengue number for each for each paired strain combination (PGYP1×PGYP1.tet; PGYP1.out×PGYP1.out.tet)×body part (whole, abdomen, thorax)×age (5 or 14 d) post inoculation. The tests were based on the means from each of 4 independently replicated experiments.

CHIKV qRT-PCR Analysis

Individual frozen mosquito bodies and heads or legs and wings were homogenized for 3 min in 1 ml of Opti-MEM® reduced serum medium respectively using glass beads and a mechanical homogenizer (Spex Industries, Edison, N.J.). The supernatant from each sample was removed for potential virus isolation and stored at −80° C. The remaining mosquito pellet from each sample was resuspended in equal volumes (200 μl) of Opti-MEM® reduced serum medium and TRIzol® LS reagent (Invitrogen Life Technologies, California) and homogenized again as described above. After incubation at room temperature for 5 min and addition of 40 μl of chloroform, the entire homogenate for each sample was then vortexed for 15 sec and transferred to a pre-spun Phase Lock Gel™ Heavy tube (5 Prime, GmbH, Germany). The lysed contents of each tube were allowed to settle for 5 min at room temperature and organic and aqueous phases were separated by centrifugation at 16 000 g for 10 min at room temperature. Aqueous phases were recovered from each tube before total RNA was extracted at room temperature using a modification of the RNeasy Mini Kit protocol (Qiagen, Australia) and on column-DNase treatment. RNA was eluted from the column with 30 μl of RNasefree H$_2$O and a final centrifugation step for 1 min. All RNA samples were stored at −80° C. prior to analysis by qRT-PCR. RNA standards were produced for the relative quantification of CHIKV RNA copy numbers normalized to RNA levels of the ribosomal *A. aegypti* housekeeping gene RpS17 (see Table 6).

Immune Genes

PGYP1.out and PGYP1.out.tet mosquitoes were analyzed by RT-qPCR for a selection of immune genes. Two biologically independent cohorts of ten sugar-fed, 5-6 day old, female mosquitoes were collected and analyzed from each mosquito line. Total RNA was extracted from whole mosquitoes using TRI REAGENT (Molecular Research Center, Inc.) or RiboZol (AMRESCO). The RNA samples were DNase treated (Promega) and reverse transcribed using random primers and SuperScript III Reverse Transcriptase (Invitrogen). Quantitative PCR was carried out as per Platinum SYBR Green protocol (Invitrogen). The sequences of the primers used for qPCR are detailed in Table 6. Primer sequences for REL1, REL2, CECG and DEFC were obtained elsewhere (Xi et al., 2008) and the other primers were designed using gene sequences obtained from VectorBase. The temperature profile of the qPCR was 95° C. for 2 min, 50° C. for 2 min and 40 cycles of 95° C. for 10 s, 60° C. for 10 s and 72° C. for 20 s. The house-keeping gene RpS17 (Cook et al., 2006) was used to normalize expression. Target gene to house-keeping gene ratios were obtained for each biological replicate using QGene 4.2 (Joehanes and Nelson, 2008). Treatment effects on the expression ratios were examined using Mann Whitney-U tests in STATISTICA V8 (StatSoft, Inc.) and fold change was calculated by the REST method (Pfaffl et al., 2002).

Immunofluorescence

Following the removal of legs and wings, 14 dpi mosquitoes were fixed overnight at 4° C. in 4% (w/v) paraformaldehyde in PBS, containing 0.5% (v/v) Triton X-100. Fixed mosquitoes were dehydrated in an ethanol series of 50, 70, 90, 95, 100% ethanol, followed by two toluene treatments and then infiltrated with paraffin wax (Paraplast-Xtra, McCormick Scientific) at 60° C. Paraffin-embedded mosquitoes were sectioned using a rotary microtome to obtain 8 μm sections that were adhered to superfrost plus slides (Menzel-Gläser). Slides were dried, deparaffinated in 100% xylene, rehydrated in an ethanol series and then washed in PBS-T before being blocked overnight in 2% (w/v) bovine serum albumin (BSA) in PBS-T at 4 C. Sections were then incubated simultaneously for 1 hour with antirabbit WSP (1:100) and anti-dengue (1:10) 4G4 or anti-*Plasmodium* CSP (Krettli et al., 1988) antibodies (1:100) (both monoclonal, developed in mouse), diluted in blocking solution. Tissue sections were washed twice with PBS-T and the slides were then incubated simultaneously with Alexa-conjugated secondary antibodies (Alexa-488 developed in rabbit or Alexa-594, developed in mice, respectively, Molecular Probes, Invitrogen) diluted 1:1000 each in blocking solution for 1 h at room temperature. After two washes in PBS-T, the slides were incubated in DAPI for 10 min, rinsed in PBS-T and then mounted using an antifading reagent (ProLong, Invitrogen). Immunostaining was analyzed with a Zeiss Axio Imager II epifluorescence microscope equipped with an Axiocam camera, using the same exposure conditions for each filter channel. Photos are representative of at least 10 mosquitoes of each treatment.

Fluorescence In Situ Hybridization

FISH was done using a modified protocol adapted from GeneDetect.com. Briefly, paraffin-embedded mosquitoes were sectioned and de-paraffinated as described above. Sections were then dehydrated in an ethanol series and hybridised overnight at 37° C. in a hybridization buffer containing 4×SSC, 50% formamide, 250 mg/ml dextran sulfate, 250 μg/ml poly(A), 250 μg/ml tRNA, 250 ug/ml salmon sperm DNA, 100 mM DTT and 0.5×Denhardt's solution and 200 ng of *Wolbachia* specific 16S rRNA probes (W2: 5'-CTTCTGT-GAGTACCGTCATTATC-3' (SEQ ID NO: 15) and W3: 5'-AACCGACCCTATCCCTTCGAATA-3" (SEQ ID NO: 16)) labelled at the 3' end with rhodamine. Both probes are 100% homologous to both wMelPop and wFlu. Following overnight hybridizations, sections were washed twice in 1×SSC containing 10 mM DTT and twice in 0.5×SSC containing 10 mM DTT for 15 min each at 55° C., followed by a 10 min wash at 0.5×SSC containing 10 mM DTT and 1 μg/ml DAPI. Slides were briefly rinsed in water, mounted using an antifading reagent (ProLong, Invitrogen) and observed and photographed as described in the immunofluorescence method.

Western Blot Analysis

Total protein from 5 mosquitoes of each treatment was extracted using protein lysis buffer containing 50 mM Tris pH 7.4, 140 mM NaCl, 0.5% (v/v) Triton X-100, 1.5 μg/ml DNaseI and protease inhibitors (Roche). Samples were boiled for 10 min in the presence of protein loading buffer, run on a 12% Laemmli SDS gel and transferred to a nitrocellulose membrane (Immobilon-P, Millipore) through the semidry Transblot SD (BioRad). Because the 4G4 antidengue antibody recognizes a conformational epitope, −mercaptoethanol was omitted from the sample loading buffer. Membranes were blocked with 5% non-fat dried milk in TBS-T overnight at 4 C, and then probed with antiwsp polyclonal antibody (Braig et al., 1998) (diluted 1:1,000 in 5% (w/v) skim milk in TBS-T) or anti-dengue (4G4) monoclonal antibody (1:100 dilution) for 1 h at room temperature. After 3 washes in TBS-T, membranes were incubated with anti-rabbit or anti-mouse IgG alkaline phosphatase conjugated antibody (Sigma) (1:4,000) for 1 h, respectively. Following washing in TBS-T blots were developed with NBT/BCIP (Promega). Western blots on *Wolbachia*-infected mosquitoes revealed a single band around 26 kDa that corresponds with the correct molecular weight of wsp (25540 Da) (Braig et al., 1998), whereas the 4G4 antibody revealed a band of around 50 kDa in dengue-positive mosquitoes.

*Wolbachia* Density in *Aedes* Spp. Mosquitoes

A standard curve was created by cloning a *Wolbachia* wsp gene fragment (Braig et al., 1998) into pGEM T-Easy (Promega). After linearization with Pst I the plasmid was serially diluted into known concentrations and run in parallel, in order to determine the absolute number of *Wolbachia* copies contained in each mosquito sample. Mann-Whitney U tests were employed (STATISTICA V8, StatSoft, Inc.) to examine the density of *Wolbachia* in both mosquito species.

PCR Amplification of *Wolbachia* Sequences from *A. fluviatilis*

The *Wolbachia* surface protein gene wsp was amplified using the primers 81F and 691R that amplify a wide range of *Wolbachia* strains (Braig et al., 1998). PCR cycling conditions were as follows: 94° C. 3 min, (94° C. 30 s, 52° C. 30 s, 68° C. 90 s)×35 cycles, then 68° C. 10 min. The reaction mixture contained 625 nM of each primer, 125 μM dNTPs, 1.5 mM MgSO4, 20 ng of mosquito DNA and 0.5 μL, of proof-reading Elongase enzyme mix (Invitrogen) in a final volume of 25 μl. PCR products were separated in 1% agarose gels and stained with ethidium bromide. Six independent PCR amplicons were cloned into the pGEM T Easy vector (Promega) and six clones were sequenced with T7 and M13R universal primers using the AB Big Dye terminator Version 3.1 kit with fluorescent sequencing (FS), AmpliTaq DNA polymerase (Perkin-Elmer) and analysed on (AB) 3730x1-96 capillary sequencer. Sequencing was done at the Australian Genome Research Facility (AGRF). Sequence similarity searches were performed using the BLAST algorithm (Altschul et al., 1997) at NCBI, and a phylogenetic tree was constructed using DNAstar (Lasergene). A partial wsp gene sequence from wFlu has been deposited in GenBank (Accession number GQ917108).

Relative Quantification of CHIKV RNA Copy Numbers

RNA standards were produced for the relative quantification of CHIKV RNA copy numbers normalized to RNA levels of the ribosomal *A. aegypti* housekeeping gene RpS17. Firstly, a CHIKV RNA synthetic transcript was produced by RT-PCR amplification of a 588 bp fragment from the CHIKV strain 06113879 using primers designed from its deduced partial E1 structural gene sequence (GenBank accession number EU404186) (see Table 6). The one-step RT-PCR was performed using the Superscript® III One-Step RT-PCR System with Platinum® Taq High Fidelity (Invitrogen Life Technologies, California) according to the manufacturer's instructions with 400 nM of each primer and 5 μl of CHIKV RNA in a final reaction volume of 50 μl. Amplification was performed in an Eppendorf Mastercycler epgradient S (Eppendorf, Germany) and included one cycle at 50° C. for 15 min for reverse transcription, an inactivation step at 94° C. for 2 min, 40 cycles of 94° C. for 2 min, 59° C. for 30 sec and 68° C. for 2.5 min and final extension at 68° C. for 5 min. Amplicon DNA was purified using the QIAquick Gel Extraction Kit (Qiagen, Australia) and supplied instructions and then cloned into the plasmid vector pGEM®-T Easy (Promega). After the presence and orientation of the insert DNA was verified by nucleotide sequencing, the plasmid was linearized for in vitro RNA transcription by digestion with SpeI. Synthetic RNA transcripts were then prepared using the Riboprobe® T7 System (Promega) before multiple treatments with DNase 1 (RQ1 RNase-Free DNase; Promega Corporation, WI, USA). The final CHIKV transcript of 654 bp was stored in single use aliquots at −80° C. and RNA levels were determined by spectrophotometry immediately prior to use. For the housekeeping gene RpS17 RNA standard, total RNA from whole *A. aegypti* mosquitoes was extracted as before with the exception that on-column DNase treatment was omitted. In this instance, RNA was DNase treated and stored as described for the CHIKV RNA transcript. To enable a direct comparison of CHIKV RNA copy numbers in prepared mosquito body plus head, and legs plus wings samples, two specific one-step qRT-PCR real-time TaqMan® assays were developed targeting the CHIKV E1 and *A. aegypti* RpS17 genes respectively. Both were performed using the ABI 7500 Fast Real-Time PCR System (PE Applied Biosystems, Foster City, Calfornia) and all reaction mixes, amplification parameters, result analysis and CHIKV primer and probe sequences were used as previously reported. Primers and dual labelled probe (5'-FAMCAGGAGGAGGAACGTGAGCGCAG-TAMRA-3") (SEQ ID NO: 17) for the RpS17 housekeeping assay were derived from the *A. aegypti* RpS17 gene sequence—GenBank accession number AY927787. Standard curves for qRT-PCRs were generated using triplicate 15-fold serial dilutions of either the CHIKV T7 RNA transcript or the prepared RpS17 reference RNA. Equivalent CHIKV RNA copy numbers normalized to reference RpS17 RNA levels were then calculated for the CHIKV infected mosquito samples by comparing threshold cycle numbers (Ct) with the respective standards.

Results

*Wolbachia* and Dengue Virus

We tested the effect of *Wolbachia* on vector competence in two mosquito genetic backgrounds: the original inbred PGYP1 line, which was stably transinfected with wMelPop-CLA (see Example 2) and the same strain after 5 generations of backcrossing to the F1 progeny of wild-caught *A. aegypti*, collected in Cairns, Australia and named PGYP1.out. These mosquito strains were compared to tetracycline-treated counterparts that were genetically identical but lacked the *Wolbachia* infection, named PGYP1.tet and PGYP1.out.tet, respectively. In addition, a wild-type strain of *A. aegypti* established from field-collected material in Cairns, Australia (Cairns3) was used as an additional negative control.

Figure 23:
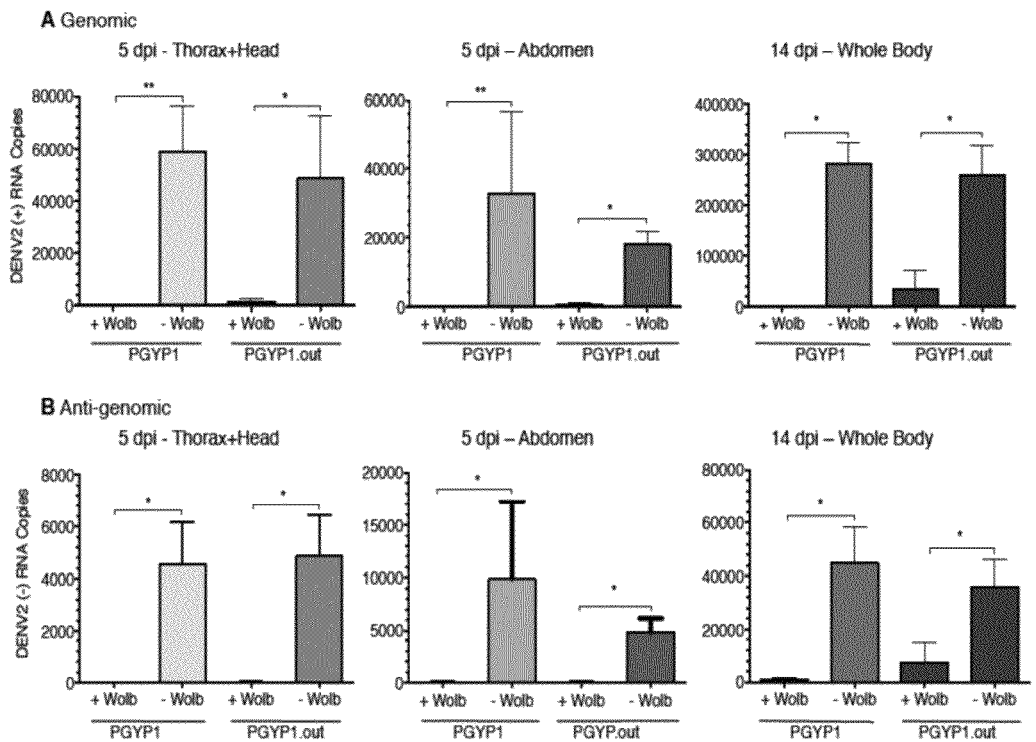
FIG. 23. Quantitative PCR analysis of dengue virus in mosquitoes. Two strains of *Wolbachia*-harbouring (+Wolb) *A. aegypti* mosquitoes (PGYP1 and PGYP1.out) and their tetracycline treated counterparts (−Wolb) (PGYP1.tet and PGYP1.out.tet) were intrathoracically injected with DENV-2. The quantity of DENV-2 RNA present was estimated by quantitative real-time PCR. A) Quantity of genomic RNA (+RNA) in thorax and head 5 days post-infection (dpi), abdomen 5 dpi and whole mosquito 14 dpi. B) Quantity of anti-genomic RNA (−RNA) in thorax and head 5 dpi, abdomen 5 dpi and whole mosquito 14 dpi. Bars represent grand means±SEM calculated across four independent replicate experiments. *$P<0.05$ by Mann-Whitney U test.
Figure 24:
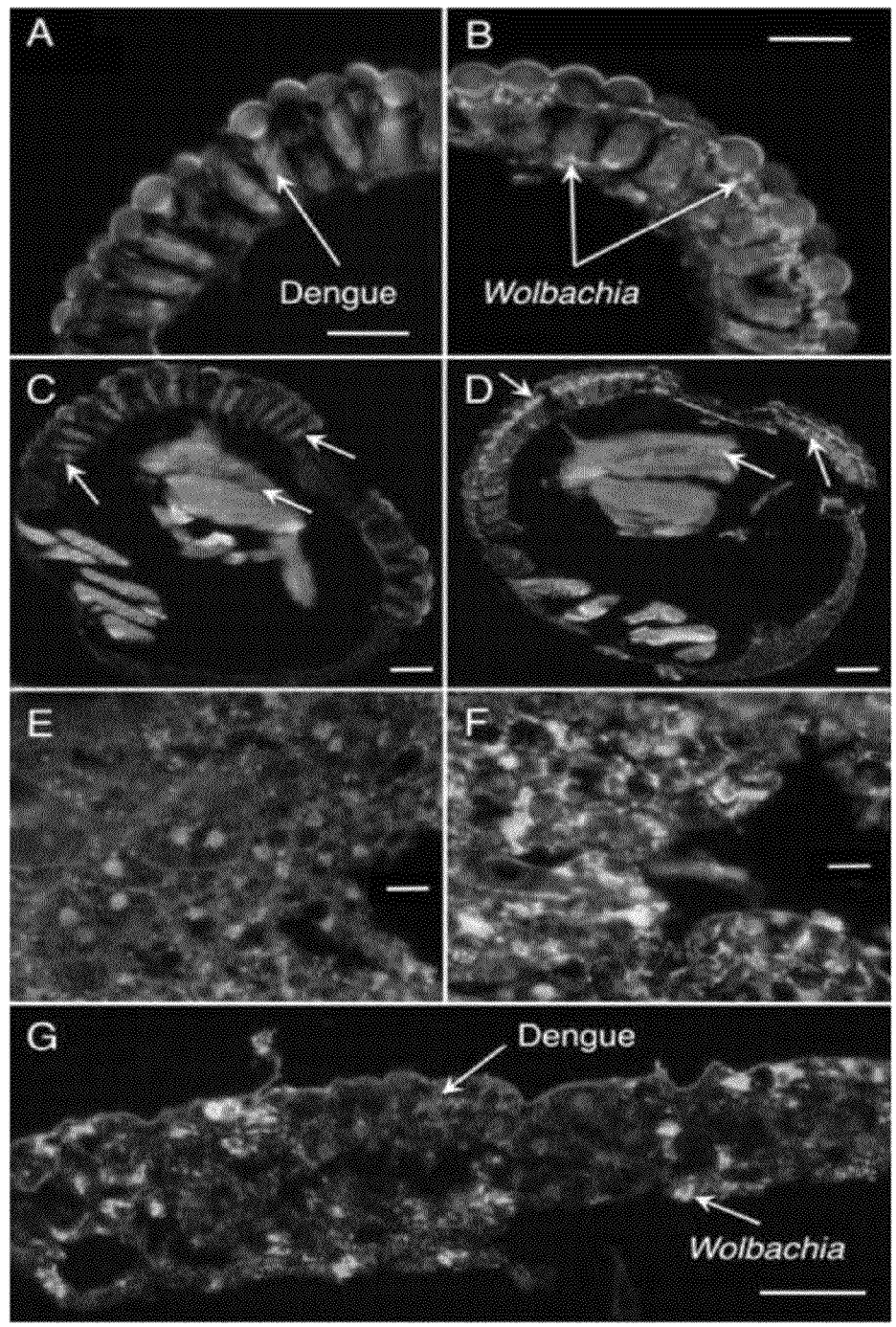
FIG. 24. Localization of *Wolbachia* and dengue virus in *A. aegypti* mosquitoes. Double immunofluorescence staining of mosquito paraffin sections showing the localization of dengue virus (in red) and *Wolbachia* (in green). Sections were probed simultaneously with polyclonal anti-wsp antibody (*Wolbachia*) and monoclonal anti-DENV antibody 4G4, followed by anti-rabbit-Alexa 488 (green) and anti-mouse-Alexa 594 (red) conjugated antibodies, respectively. DNA (blue) is stained with DAPI. In panels A, B, E, F, G the red, green and blue channels are merged. C and D show only red and green channels merged. (A, C, E) PGYP1.tet (−Wolb) mosquitoes, 14 days post DENV-2 thoracic 39 injection. Dengue virus is visible in ommatidia cells (A, C) and fat tissue (E). (B, D, F) PGYP1 mosquitoes (+Wolb), 14 days post DENV-2 thoracic injection. *Wolbachia* can be seen in ommatidia cells and brain (B, D) and fat tissue (F). In contrast no dengue virus was detected. (G) Cellular exclusion of DENV-2 by *Wolbachia*, where the presence of both *Wolbachia* and DENV-2 was observed at very low frequency in a small number of *Wolbachia*-infected outcrossed mosquitoes, 14 days post DENV-2 injection. Dengue is only apparent in cells lacking *Wolbachia* however. Scale bars: A-D, G: 50 µm; E,F: 20 µm. See also FIG. 28.
Figure 28:
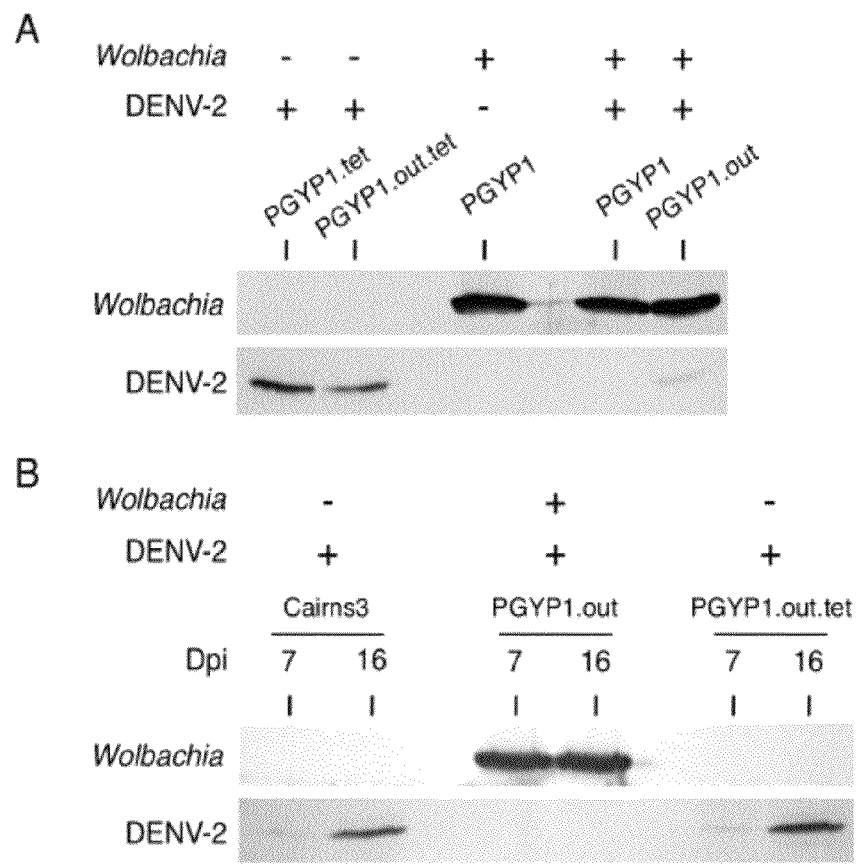
FIG. 28. *Wolbachia* and/or dengue proteins detected in *A. aegypti* mosquitoes. Western blots showing the presence of *Wolbachia* and/or dengue virus in *A. aegypti* mosquitoes infected with DENV-2 using wsp polyclonal antibody for *Wolbachia* detection and 4G4 monoclonal antibody for DENV-2 detection. The expected infection status (*Wolbachia* or DENV-2) of the mosquitoes used is indicated above each blot. (A) 14 days after thoracic injection with DENV-2, (B) 7 and 16 days after oral feeding with DENV-2.

Mosquitoes were fed an artificial blood meal spiked with DENV-2 in four independent experiments to examine possible interactions with *Wolbachia*. The presence of DENV-2 in whole mosquito bodies was examined 7 and 14 days post exposure using a cell culture enzyme immunoassay (CCEIA) (Knox et al., 2003). In three separate experiments no *Wolbachia*-infected mosquitoes (PGYP1.out) tested positive for DENV-2, but DENV-2 infection rates in *Wolbachia*-uninfected mosquitoes (PGYP1.out.tet and Cairns3) ranged from 30-100% (Table 3, Exp 1-3). The body viral infection rates in PGYP1.out.tet mosquitoes ranged from 30-100% after 7 d and 48-97% after 14 d, while the body viral infection rates in Cairns3 ranged from 50-95% after 7 d and 57-95% after 14 d. The disseminated viral infection rates measured through the presence of virus in mosquito legs in tetracycline-treated *A. aegypti* ranged from 10-23 and 37-43% after 7 and 14 d respectively. Disseminated infections in *Wolbachia*-free wildtype Cairns3 strain of *A. aegypti* ranged from 5-13% and 20-33% after 7 and 14 d, respectively (Table 3) (P<0.001, chi-square). In one experiment (Table 3, Exp 4) when mosquitoes were fed the highest titer (107.8 Logs) of DENV-2 a small number of *Wolbachia*-infected mosquitoes tested positive for DENV-2 at both 7 and 14 days post infection (5 and 8%, respectively) but this was significantly fewer than *Wolbachia* uninfected controls (63-78% and 70-75%, respectively) (P<0.001, chi-square). To provide a more conservative test of *Wolbachia*-mediated interference, mosquitoes were intrathoracically injected with DENV-2. These experiments circumvented the midgut barrier to infection (Woodring et al., 1996) and allowed for the delivery of a repeatable inoculating dose (around 2,750 infectious particles/mosquito) of DENV-2 that produced consistent high-titre infections in control mosquitoes. Accumulation of genomic (+RNA) and antigenomic (−RNA) RNA strands was assessed at 5 and 14 d post-injection by quantitative real time PCR using DENV-2 specific primers (Richardson et al., 2006). At both time points, the amount of DENV-2 RNA present was reduced by up to 4 logs in both the PGYP 1 and PGYP1.out *Wolbachia*-infected strains compared to their paired tetracycline treated counterparts (FIG. 23, Table 5). Furthermore, when mosquito saliva collected from mosquitoes 14 d post injection was tested for the presence of infectious virus by CCEIA, none of the *Wolbachia*-infected mosquitoes samples tested positive for virus. A dramatic reduction in viral protein synthesis was also observed by immunofluorescent microscopy (IFA) (FIG. 24A-F) and Western blot analysis (FIG. 28). Double immunofluorescent staining of paraffin sections of *Wolbachia*-uninfected control mosquitoes 14 days post-injection showed DENV-2 infection predominantly in mosquito fat body as well as ommatidia (FIG. 24A-F) and nervous system. DENV-2 was not detected in any of these tissues in *Wolbachia*-infected mosquitoes (PGYP1 and PGYP1.out) whereas *Wolbachia* was clearly visible in the fat tissue, ommatidia (FIG. 24), brain, ovaries, and Malpighian tubules. Only in a few rare individuals was DENV-2 detected in patches of fat tissue in PGYP1.out mosquitoes. However in these cases *Wolbachia* and DENV-2 were not co-localized in the same cells and DENV-2 was only seen in occasional patches of cells that were not infected with *Wolbachia* (FIG. 24G). The presence of DENV-2 in some injected PGYP1.out mosquitoes was also confirmed by Western blot (FIG. 28A).

*Wolbachia* and Chikungunya Virus

We then went on to determine if the virus interference phenotype would extend to the alphavirus CHIKV. The virus strain used in the experiments contained the alanine to valine mutation in the membrane fusion glycoprotein E1 gene (E1-A226V), which has been linked to increased infectivity in *A. albopictus*. An Australian population of *A. aegypti* was recently shown to also be a highly efficient laboratory vector of this virus strain. Mosquitoes were exposed to a blood/virus mixture containing 106.4 CCID50/ml of CHIKV, and at various timepoints post exposure, mosquitoes were processed for quantification of the number of viral RNA copies using qPCR and CHIKV-specific primers and probes. Immediately after feeding, the number of CHIKV genomic (+RNA) RNA copies in the body and head were comparable for all three lines, suggesting that they imbibed similar amounts of virus (Table 4). The median number of copies then decreased in all three lines on days 2, prior to it increasing in the PGYP1.out.tet and Cairns3 mosquitoes to its highest level at day 14-post exposure. The day 14 infection rates were 87% and 79% for the PGYP1.out.tet and Cairns3 controls and 17% for the *Wolbachia* infected PGYP1.out line (P<0.001, chi-square). In all three groups, CHIKV RNA was detected in the legs and wings immediately after feeding, as percentage of dissemination (Table 4). This may represent either direct contact between the legs and/or wings and the blood/virus mixture or a rupture of the mesenteron, which released virus directly in the hemolymph (Turell, 1988). After day 0, CHIKV was not detected in the legs and wings of any PGYP1.out (+Wolb) mosquitoes. In contrast, on all days post exposure, virus was detected in the legs and wings of PGYP.out.tet and Cairns3 control mosquitoes (−Wolb) and by day 14, the virus was detected in the legs and wings of 100% and 90%, respectively, of mosquitoes which had positive bodies and heads (P=0.125, chi-square).

*Wolbachia* and *Plasmodium*

Figure 25:
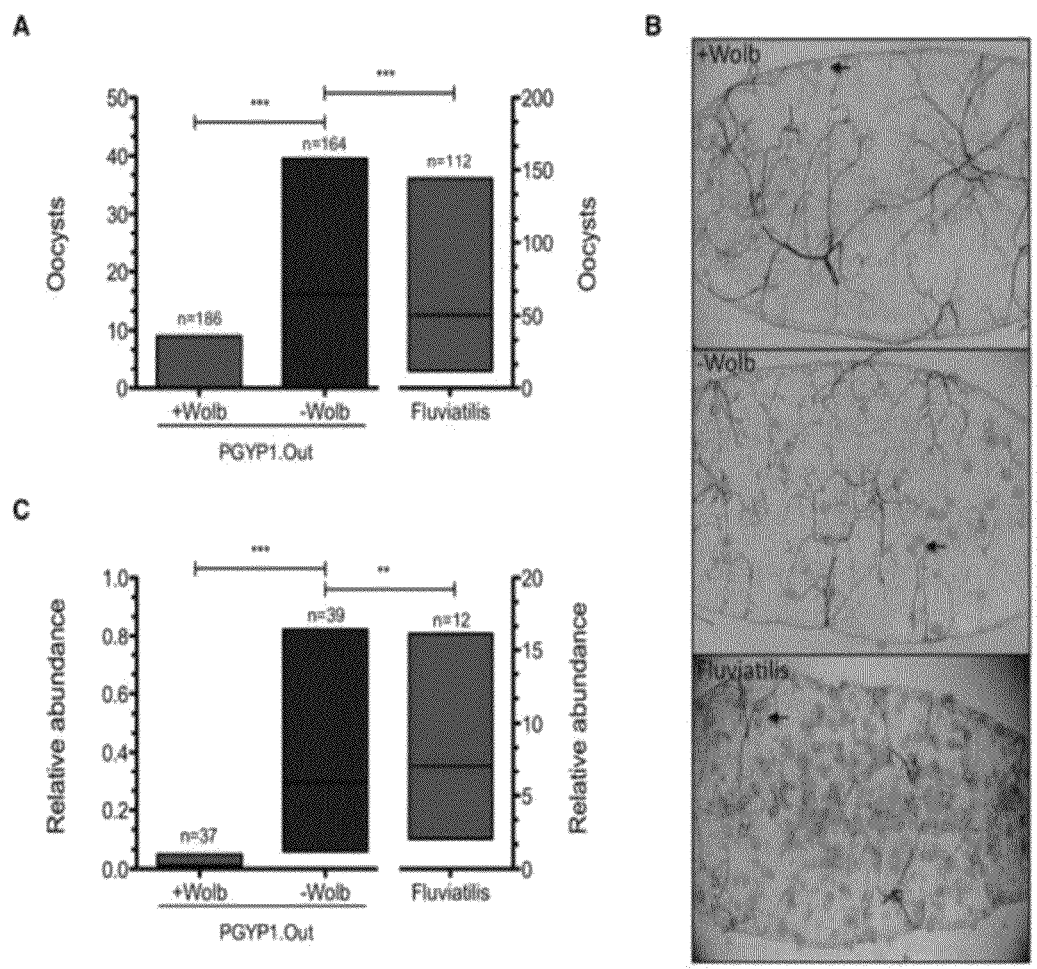
FIG. 25. *Plasmodium gallinaceum* detection in *Aedes* spp. mosquitoes. *A. aegypti* and *A. fluviatilis* mosquitoes were fed on *P. gallinaceum* infected chickens and parasites infection was detected by different means. A) Box plots of median numbers and 25 (bar below median) and 75% (above median) percentiles of oocyst intensities, seven days post-infection in wMelPop infected (PGYP1.out, +Wolb) or uninfected (PGYP.out.tet, −Wolb) *A. aegypti* and in *A. fluviatilis* mosquitoes (***$P<0.0001$ by Mann-Whitney U test). B) Mercurochrome staining of mosquito midguts showing representative localization of *Plasmodium gallinaceum* oocysts (arrows) in wMelPop (+Wolb) infected and uninfected (−Wolb) and in *A. fluviatilis* mosquitoes, seven days post-infection (100× magnification). C) Quantitative PCR analysis 15 days after infection showing the relative abundance 40 of *Plasmodium* 18S ssu rRNA sequences in comparison to Actin gene ($P<0.005$, *$P<0.0001$ by Mann-Whitney U test). See also FIG. 29.
Figure 29:
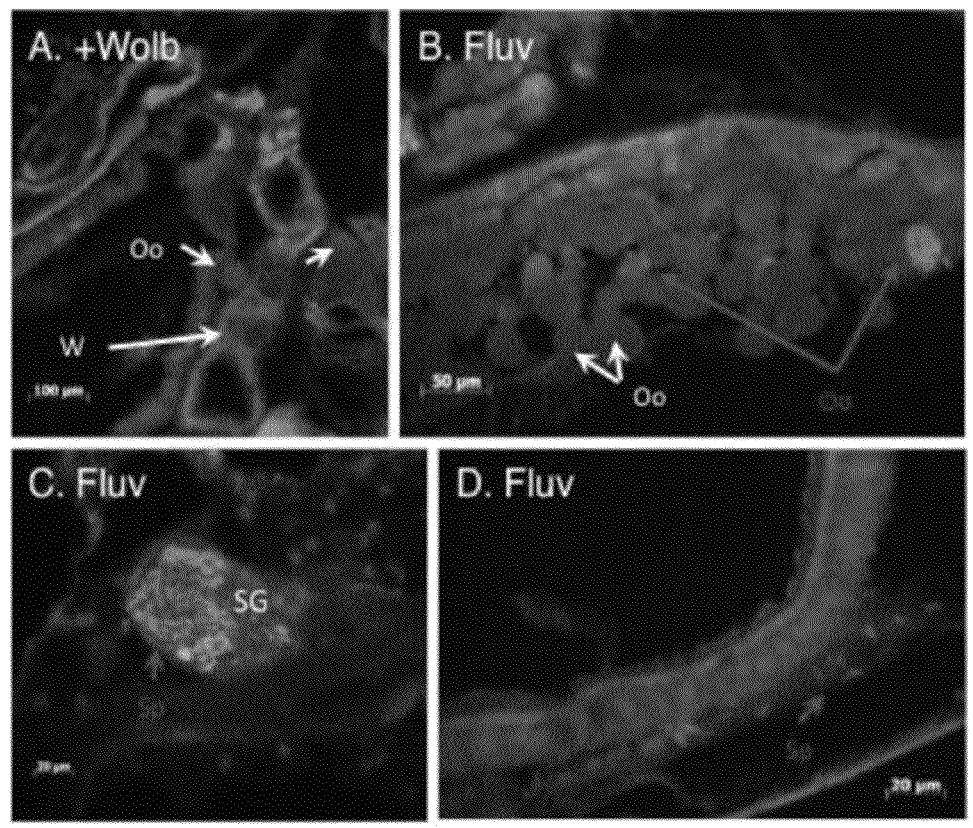
FIG. 29. *P. gallinaceum* distribution and maturation in *Aedes* spp. mosquitoes 7 and 14 days post infection. A) DAPI (blue) staining of an oocyst (Oo) in the gut of a PGYP1.out (+Wolb) mosquito, 7 days postinfection (dpi) with *Plasmodium gallinaceum*. The presence of numerous wMelPop *Wolbachia* (red) nearby Malpighian cells is detected by FISH. B) Immunofluorescence localization of two mature oocysts (red Oo) among immature oocysts (white Oo) in the gut epithelia of *A. fluviatilis*, 7 dpi with *P. gallinaceum*. C, D) Immunofluorescence showing the presence of mature *P. gallinaceum* sporozoites (Sp, red) in the salivary gland (SG) and gut epithelia of *A. fluviatilis*, 15 dpi.

Considering that the viral interference effect appeared robust for two unrelated arboviruses we then went on to test for the effect on the protozoan parasite *P. gallinaceum*. While not a human pathogen, this species of malaria parasite is known to be able to infect *A. aegypti* mosquitoes in the laboratory. *Wolbachia* infected and uninfected *A. aegypti* mosquitoes (PGYP1.out and PGYP1.out.tet strains) as well as a susceptible strain of *Aedes fluviatilis* were fed in parallel on *P. gallinaceum* infected chickens. *A. fluviatilis* has a broad geographical distribution in Latin America and has been used in the laboratory as a safe avian malaria (*P. gallinaceum*) model vector, as it does not naturally transmit DENV or yellow fever virus (Tason de Camargo and Krettli, 1981). Seven days post-feeding on infected chickens, mosquito midguts were dissected and the number of *Plasmodium* oocysts counted. The presence of wMelPop-CLA *Wolbachia* significantly reduced the oocyst load in *A. aegypti* mosquitoes (P<0.0001, Mann-Whitney U test) (FIGS. 25A and 25B) by 67 to 88%, in four independent experiments, in comparison to tetracycline treated mosquitoes. Furthermore, the proportion of mosquitoes that contained oocysts in the midgut was significantly lower in PGYP1.out (43%), than in PGYP1.out.tet (74%) or *A. fluviatilis* (88%). To quantify the difference in parasite loads, fifteen days after infection mosquitoes were collected and the DNA was extracted. The relative abundance of *Plasmodium* genomic DNA was measured by the 18S ssu rRNA gene (Schneider and Shahabuddin, 2000) and normalized to the mosquito Actin gene using qPCR and the results showed the same pattern of interference as observed from oocyst count data. In PGYP1.out mosquitoes *Plasmodium* genomic DNA was 26-fold less abundant than in PGYP1.out.tet lines (FIG. 25C). Immunofluorescence analysis using an anti-CSP (*Plasmodium* circumsporozoite protein) monoclonal antibody shows the presence of mature oocysts in both mosquito species (FIG. 29B), but very rarely in *Wolbachia*-infected mosquitoes.

Figure 30:
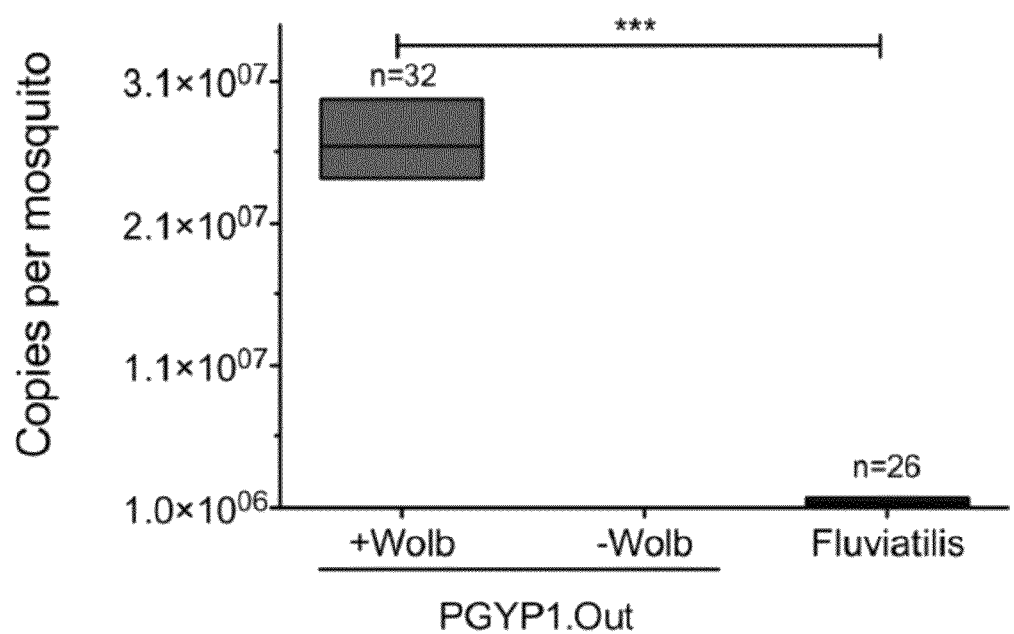
FIG. 30. *Wolbachia* density in *Aedes* spp. mosquitoes. Box plots of median numbers and 25 and 75% percentiles of number of *Wolbachia* copies per mosquito, based on standard curve analysis for the wsp gene. wMelPop-CLA infected PGYP1.out strain (+Wolb) or PGYP1.out.tet uninfected (−Wolb) strains of *A. aegypti* and *A. fluviatilis* mosquitoes (***$P<0.0001$ by Mann-Whitney U test).
Figure 31:
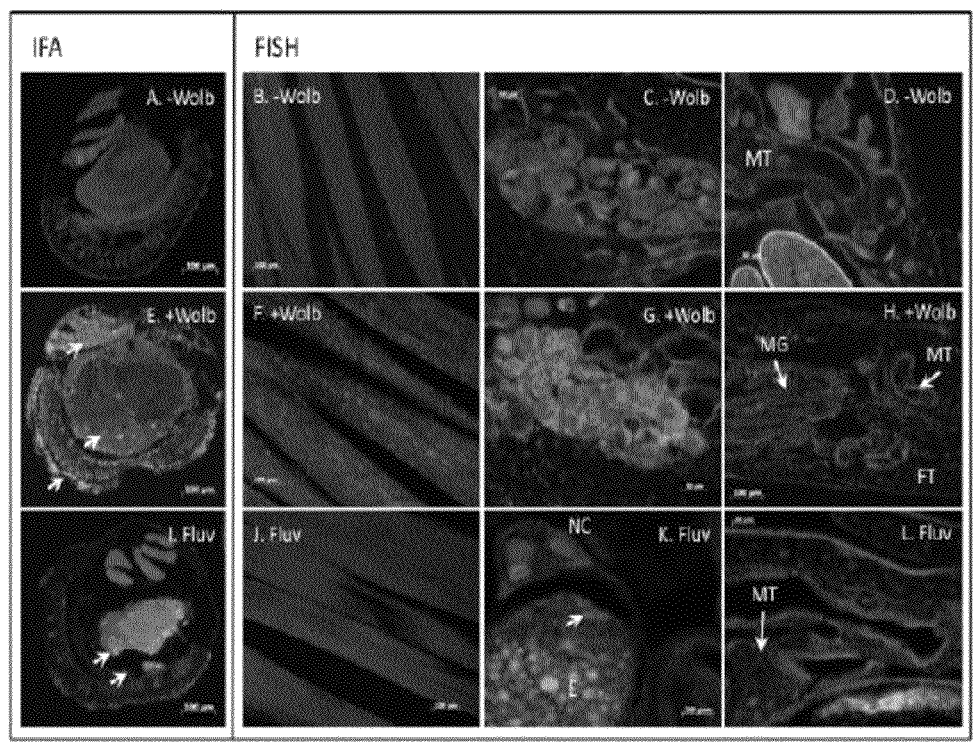
FIG. 31. wMelPop-CLA and wFlu *Wolbachia* distribution in *Aedes* spp. mosquitoes. The first column (A, E, I) shows the localization of wMelPop-CLA (E) and wFlu (I) *Wolbachia* (green) in *A. aegypti* and *A. fluviatilis* heads. Both *Wolbachia* strains are localized by immunofluorescence using a *Wolbachia* specific polyclonal anti-wsp antibody and visualized using rabbit-Alexa 488 (green). B, C, D) FISH showing the absence of *Wolbachia* in thoracic muscle, developing oocytes and Malpighian tubules of uninfected mosquitoes. F, G, H) wMelPop-CLA *Wolbachia* is present at high densities in the thoracic muscle, embryos, Malpighian tubules (MT), fat tissue (FT) and around the midgut (MG) of PGYP1.out mosquitoes (+Wolb). J, K, L) wFlu *Wolbachia* is absent in the thoracic muscle of *A. fluviatilis* (J), but is present in the nurse cells (NC), apical part of embryos (E) and in the Malpighian tubules (MT), although the densities are much lower than those observed for wMelPop-CLA-transinfected *A. aegypti* (+Wolb). IFA Micrographs (A, E, I) were taken using a filter for Alexa 488 (green, *Wolbachia*), Alexa 594 (contrast) and DAPI (DNA, blue) and then merged. FISH Micrographs (B-D, FH, J-L) were taken using a filter for Alexa 488 (contrast), Alexa 594 (red, *Wolbachia*) and DAPI (DNA, blue) and then merged.

When we incubated the mosquito sections with an anti-*Wolbachia* (wsp) antibody we serendipitously discovered a *Wolbachia* infection in *A. fluviatilis* mosquitoes indicating that this species of mosquito was naturally infected with *Wolbachia*. PCR using *Wolbachia* general wsp primers (Braig et al., 1998; Zhou et al., 1998) amplified a fragment from all *A. fluviatilis* tested. Sequence of the amplified DNA indicated that this *Wolbachia* strain (named wFlu) belongs to the *Wolbachia* B supergroup and is distantly related to wMelPop-CLA. qPCR analysis revealed that the density of wFlu in *A. fluviatilis* is about 20-fold lower than the density of wMelPop-CLA in *A. aegypti* (FIG. 30). We then examined the tissue localization of *Wolbachia* in both mosquito species and whereas wMelPop-CLA is distributed throughout most tissues of the mosquito including the fat body, anterior midgut, muscle, nervous tissue, malpighian tubules and ovaries, wFlu is present only in ovaries, malpighian tubules and less frequently in the head, but absent from ommatidia (FIGS. 26 and 31).

Immunity Genes

Figure 27:
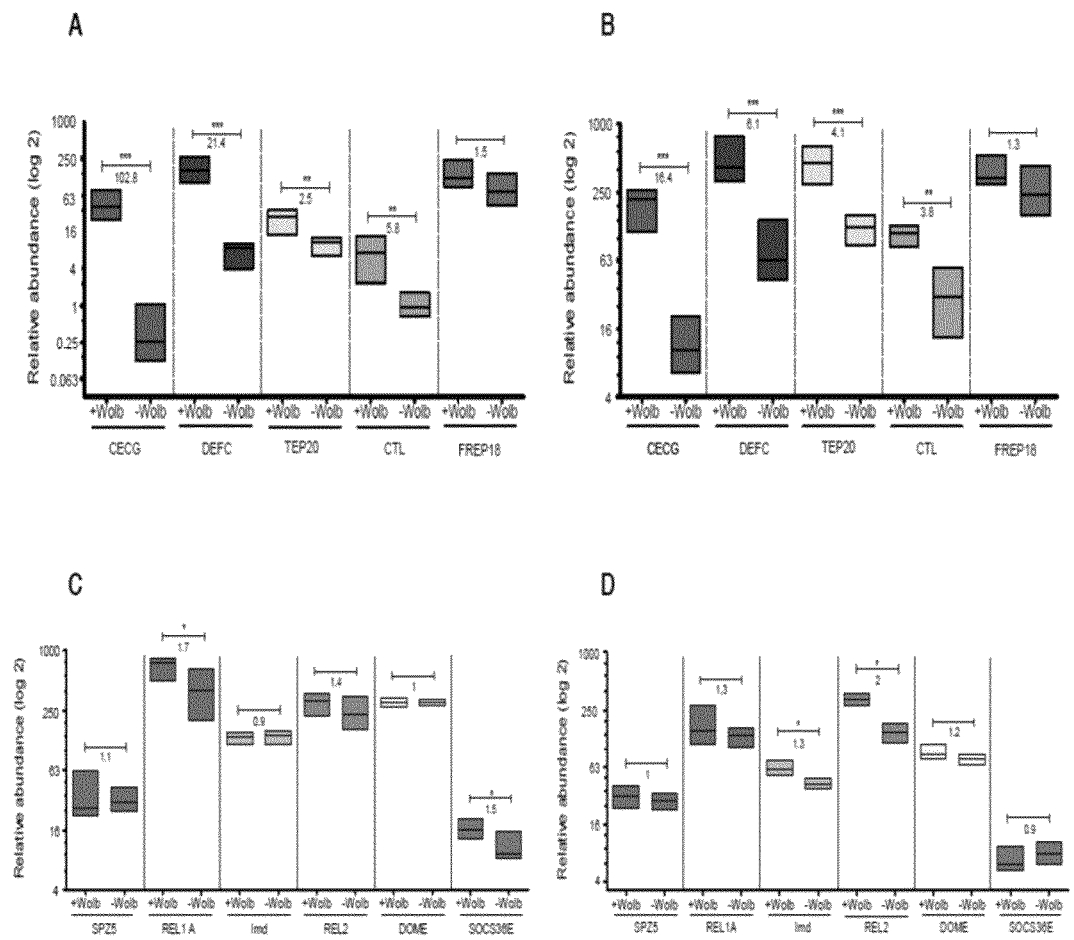
FIG. 27. Immune gene regulation in response to *Wolbachia* infection. RTqPCR analysis of mRNA expression from selected immune genes of 5-6 day old PGYP1.out and PGYP1.out.tet mosquitoes. Graphs show the target gene to house-keeping gene ratio calculated for the genes indicated from the immune pathways. Box plots of median numbers and 25 (bar below median) and 75 (above 41 median) percentiles of 10 individual mosquitoes analyzed from a single cohort. Results from two independently reared cohorts are shown (cohort 1 A and C; cohort 2 B and D). Statistically significant medians by Mann Whitney-U test (*$P<0.05$, $P<0.01$ and *$P<0.001$) are indicated and the corresponding foldchange for the gene is shown above the box plots.

To examine whether resistance of *Wolbachia* infected mosquitoes to pathogen infection may be related to stimulation or priming of the mosquito innate immune system, we quantified the expression of a sample of immune genes. It was recently demonstrated that some immune genes are differentially regulated in *A. aegypti* mosquitoes infected with dengue virus (Xi et al., 2008). Interestingly, regulation of the immune pathway genes in these mosquitoes was also stimulated by their natural gut microbiota and rearing mosquitoes aseptically, and so depleting their bacterial flora, resulted in a 2-fold increase of dengue virus in the midgut (Xi et al., 2008). We chose a subset of the genes that were shown to be upregulated upon dengue virus infection to assess the effect of *Wolbachia* infection on the mosquito immune system. The expression levels of eleven immune pathway genes in the wMelPop-CLA infected PGYP1.out and its uninfected control line were compared for two independently reared cohorts of mosquitoes (FIG. 27). In each of the experiments four genes encoding representatives of the immune effector molecules cecropin, defensin, thio-ester containing proteins (TEP) and C-type lectins were significantly upregulated in the presence of wMelPop-CLA, whereas FREP18 (fibrinogenrelated protein 18) levels remained unchanged (FIG. 27 A and B). In contrast, while a statistically significant (P<0.05) differential mRNA expression between mosquitoes with and without *Wolbachia* was observed for a subset of the genes from the Toll, IMD and Jak/STAT signaling pathways (FIG. 27C Experiment 1-Rel 1A and SOCS36E; FIG. 27D Experiment 2—IMD and Rel 2) these differences were inconsistent across the two experiments, suggesting that the variation between cohorts was greater than any differences induced by *Wolbachia*. In addition, in these cases the fold-change of mRNA expression was low (below 2-fold), whereas the effector genes were induced as much as 100-fold by the presence of *Wolbachia* (FIGS. 27A and 27B). These results indicate that the presence of wMelPop-CLA in mosquitoes stimulates expression of at least some immune effector genes, although a clear stimulation of the classical innate immune signaling pathways was not repeatably identified.

Example 7

A Virulent *Wolbachia* Infection Decreases the Viability of the Dengue Vector *Aedes Aegypti* During Periods of Embryonic Quiescence Materials and Methods Mosquito Strains and Maintenance wMelPop-infected PGYP1 and tetracycline-cleared PGYP1.tet strains of *Aedes aegypti* (see Example 2) were maintained at 25° C., 75-85% relative humidity, with a 12:12 h light:dark photoperiod. Larvae were reared in plastic trays (30×40×8 cm) at a set density of 150 larvae in 3 L distilled water, and fed 150 mg fish food (TetraMin Tropical Tablets, Tetra, Germany) per pan every day until pupation. Adults were kept in screened 30×30×30 cm cages, and provided with constant access to 10% sucrose solution and water. Females (5 days old) were blood-fed using human blood for egg production. For routine colony maintenance, eggs from PGYP 1 were hatched 5-7 days post-oviposition (i.e. without prolonged desiccation) to initiate the next generation. All fitness experiments with PGYP 1 were conducted at $G_{20}$ to $G_{22}$ post transinfection.

Pre-imaginal Development and Survivorship

Eggs (120 h old) from PGYP 1 and PGYP1.tet strains were hatched synchronously in nutrient-infused deoxygenated water for 1 h. After hatching, individual first instar larvae (n=156 per strain) were placed into separate plastic 30 mL plastic cups with 20 mL of water, and fed 1 mg powdered TetraMin suspended in distilled water each day until pupation. The number of days spent in each pre-imaginal life stage (i.e., $1^{st}$, $2^{nd}$, $3^{rd}$ and $4^{th}$ instars, pupae), mortality at each stage, and sex of eclosing adults were recorded every 24 h. Stage-specific development and eclosion times for each strain were compared using Mann-Whitney U (MWU) tests conducted in Statistica Version 8 (StatSoft, Tulsa, Okla.).

Adult Wing Length Measurements

As an indicator of adult body size, wing lengths of PGYP1 and PGYP1.tet mosquitoes (n=50 of each sex) derived from the pre-imaginal development time assay were measured (Nasci, 1986). Wing lengths of males and females from each strain were compared using MWU tests.

Viability of Quiescent Embryos Over Time

PGYP 1 and PGYP1.tet females were blood-fed on human blood, and 96 h post-blood meal isolated individually for oviposition in plastic *Drosophila* vials with wet filter paper funnels. After oviposition, egg papers were kept wet for 48 h, after which time they were removed from vials, wrapped individually in paper towel, and conditioned for a further 72 h at 25° C. and 75-85% relative humidity. Egg batches were then moved to their respective storage temperature of 18° C., or 25° C. in glass desiccator jars; maintained at a constant relative humidity of 85% with a saturated KCl solution (Winston and Bates 1960). For each temperature, 20 oviposition papers from each strain were hatched at seven time points at 7 day-intervals (5 to 47 days post-oviposition) by submersion in nutrient-infused deoxygenated water for 48 h. To hatch any remaining eggs, oviposition papers were dried briefly then submersed for a further 5 days and before the final number of hatched larvae was recorded. Regression analysis was used to detect trends in the viability of eggs from each strain over time. MWU tests were used to compare viability of eggs between strains at the same storage age.

Lifetime Productivity Measurements

Replicate 30×30×30 cm cages containing 200 individuals of each sex from PGYP1 and PGYP1.tet strains were maintained over multiple gonotrophic cycles, with ad libitum access to 10% sucrose solution and water, for the duration of their lifespan. During each cycle, females were provided with a human blood meal for 2×10 min periods on consecutive days, and 96 h post-blood meal a random sample of females (n=48) was collected from each cage and isolated individually for oviposition. Following a set 24 h period for oviposition, females were returned to their respective cages and the proportion of females laying eggs determined. Eggs were conditioned and hatched 120 h post-oviposition as described above, and the total number of eggs (fecundity) and hatched larvae (fertility) from each female were recorded. To ensure that gravid females not sampled for oviposition could also lay eggs every cycle, oviposition cups were introduced into each stock cage (96 h post-blood meal) for a period of 48 h. Females were then blood fed to initiate the next gonotrophic cycle.

Cages were sampled until all females in the population were dead, which occurred after 7 and 16 gonotrophic cycles for PGYP 1 and PGYP1.tet strains respectively. To ensure PGYP1.tet females did not become depleted of sperm, young males (3 days old) were supplemented to this cage after 8 gonotrophic cycles. An analysis of covariance (ANCOVA) was used to examine the relationship between mosquito fecundity/fertility and the covariates mosquito age and infection status. Regression analysis was used to detect trends in fecundity/fertility of mosquitoes from each strain over their lifespan. Student's t-test was used to compare the fecundity/fertility of mosquitoes from both strains of the same age.

Results

Pre-imaginal Development and Adult Size

Figure 32:
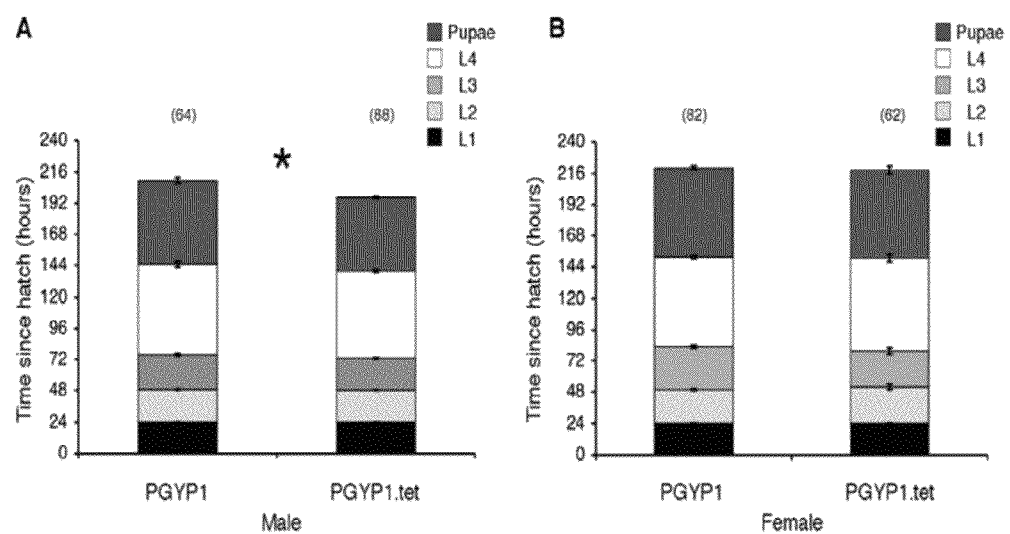
FIG. 32. Pre-imaginal development times of (A) males and (B) females from the wMelPop-infected PGYP1 and tetracycline-cleared PGYP1.tet *A. aegypti* strains. Average development time±SE for each immature stage is shown. Numbers of replicates for each strain are denoted in parentheses above error bars. Asterisks indicate a significant difference in the time to eclosion between strains ($P<0.001$, MWU test).

No significant differences in development times for larval stages of wMelPop-infected PGYP1 or tetracycline-cleared PGYP1.tet males (FIG. 32A) were found (MWU, P>0.05 for all comparisons). In contrast, the mean development time for male PGYP1 pupae (64.88±1.38 h) was significantly greater relative to PGYP1.tet (57.00±1.25 h) (MWU, U=1892.00, P<0.001), resulting in a longer cumulative time to eclosion for this strain (MWU, U=1484.50, P<0.001). For females (FIG. 32B), development times for immature stages were not significantly different between strains; except for third instar larvae where PGYP 1 development times were increased by ~5 h relative to PGYP1.tet (MWU, U=1929.00, P=0.013). Despite this delay, eclosion times for PGYP1 females were not significantly different from PGYP1.tet (MWU, U=2185.50, P=0.15). Overall, the survivorship of immature stages from both strains to adulthood was identical (96.15%).

Figure 33:
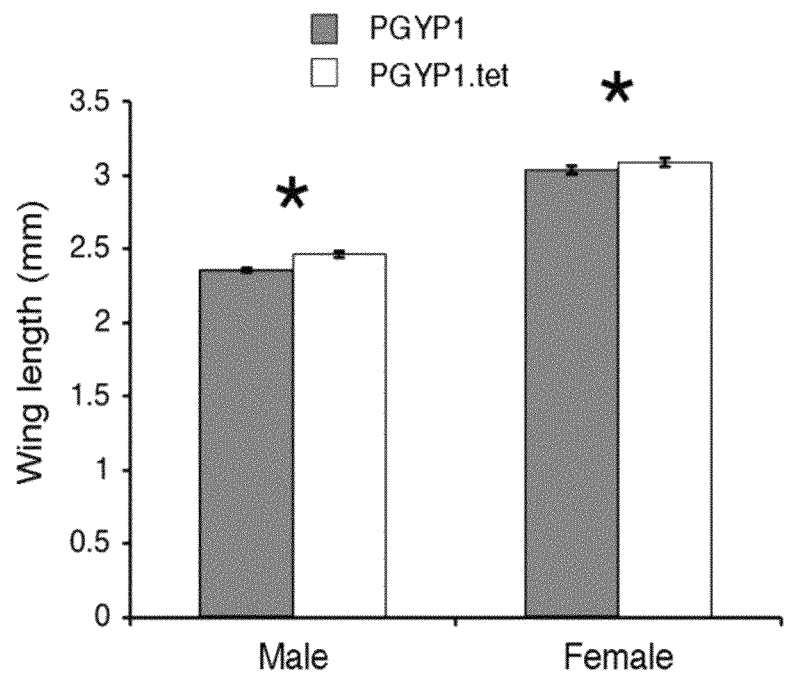
FIG. 33. Wing-size comparisons of PGYP 1 and PGYP1.tet strains. Average wing lengths and standard error bars are shown. Asterisks indicate values significantly different from one another ($P<0.05$, MWU test).

A comparison of the wing lengths of newly emerged adults from both strains revealed a minor, yet statistically significant adult size cost to wMelPop infection for both sexes (FIG. 33). Wing lengths of PGYP1 males (2.36±0.01 mm, n=50) were significantly shorter than those of PGYP1.tet males (2.46±0.02 mm, n=50) (MWU, U=661.50, P<0.0001). A smaller size difference (MWU, U=955.00, P=0.04) was found between PGYP1 females (3.03±0.03 mm, n=50) and PGYP1.tet females (3.09±0.03 mm, n=50).

Viability of Quiescent Embryos Over Time

Figure 34:
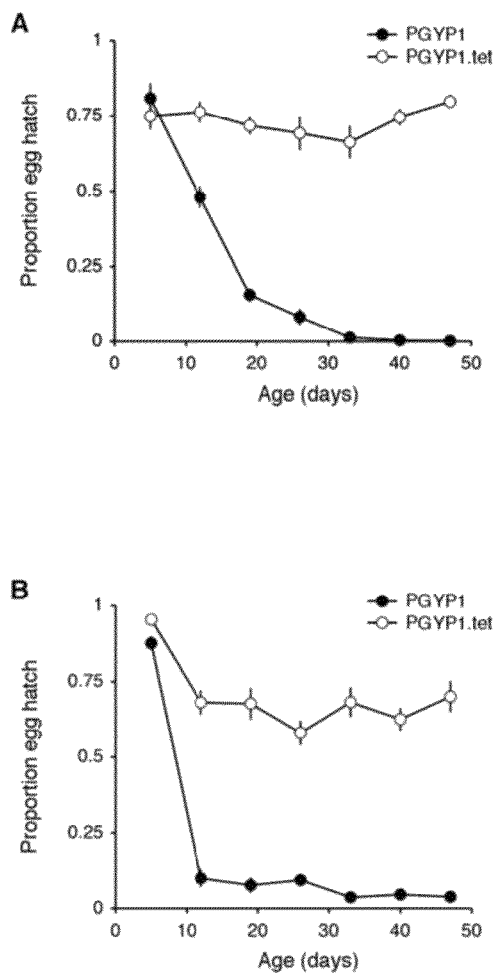
FIG. 34. Viability of quiescent embryos from PGYP1 and PGYP1.tet strains over time at different temperatures. After embryonic maturation (120 h post oviposition), eggs were stored at either: (A) 25° C. and (B) 18° C., with 85% relative humidity. Average proportion of eggs hatching (n=20 oviposition papers per time point) and standard error bars are shown.

The viability of quiescent embryos from the wMelPop-infected PGYP1 strain decreased over time at 25° C. and 18° C., whereas viability of embryos from of the tetracycline-treated PGYP1.tet strain was relatively stable at both storage temperatures (FIG. 34). At 25° C. (FIG. 34A), there was no significant difference in embryonic viability between PGYP1 (80.93±5.12%) and PGYP1.tet strains (74.96±4.37%) at 5 days post oviposition (MWU, U=146.50, P=0.1478). As quiescent embryos aged, however, PGYP1 embryonic viability decreased rapidly over time ($R^2=0.6539$, $F_{1,140}=260.73$, $P<0.0001$), such that by 40 days post oviposition very few PGYP1 eggs hatched (0.44±0.24%). In contrast, PGYP1.tet embryonic viability remained relatively constant over time ($R^2=0.0005$, $F_{1,140}=0.07$, $P=0.7897$) with ~75% of quiescent eggs hatching at each time point. An analogous trend was observed at 18° C. (FIG. 34B), where initially hatch rates were comparable between the two strains, but subsequently a greater loss in embryonic viability was observed for PGYP1 ($R^2=0.4035$, $F_{1,140}=93.34$, $P<0.0001$) relative to PGYP1.tet ($R^2=0.0803$, $F_{1,140}=12.05$, $P<0.001$). This was particularly evident at 12 days post oviposition where embryonic viability declined more rapidly in PGYP1 (9.88±2.96%) compared to PGYP1.tet (68.06±4.12%) after being moved to a cooler storage temperature (MWU, U=5.00, P<0.0001).

Reproductive Output Over Lifespan

Figure 35:
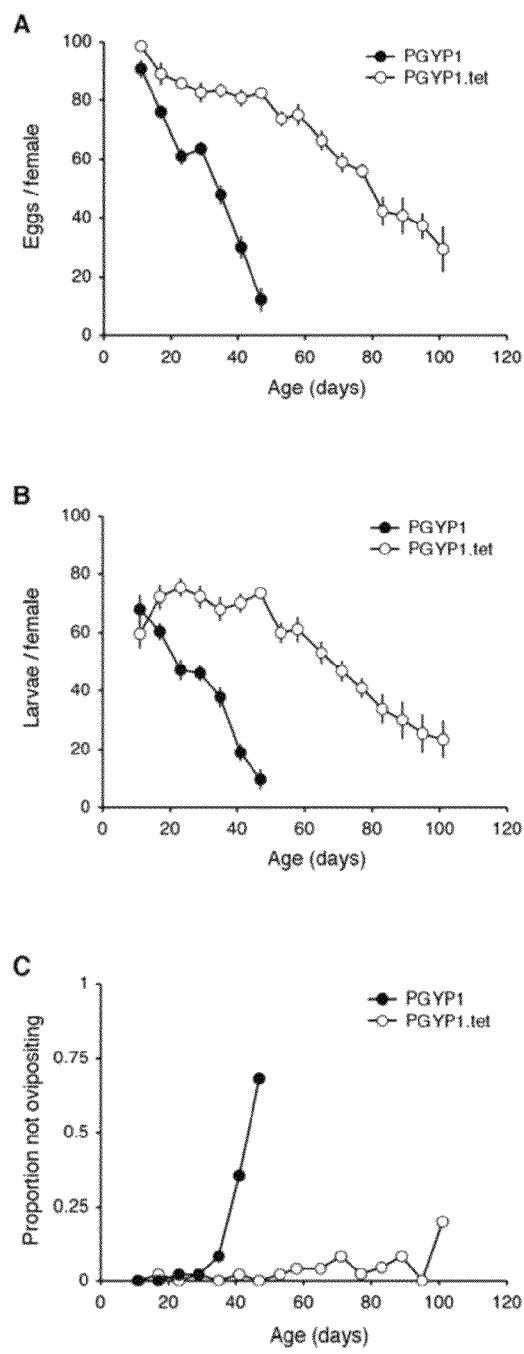
FIG. 35. Age-associated decline of fecundity in PGYP1 and PGYP1.tet strains. (A) Average number of eggs oviposited per female±SE. (B) Average number of larvae produced per female±SE, and (C) Proportion of sampled females that did not oviposit. Females were assayed over successive gonotrophic cycles until death (n=48 females per time-point). As death occurred over time, samples sizes decreased below 48 females in cycle 7 for PGYP1 females (n=22), and in cycles 13-16 for PGYP1.tet females (n=22, 12, 5, and 5 respectively).

PGYP1 and PGYP1.tet females had similar reproductive outputs in terms of the number of eggs oviposited and the number of viable larvae hatched per female during their first gonotrophic cycle (FIG. 35A and B). However, during subsequent cycles both fecundity (FIG. 35A) and fertility (FIG. 35B) of PGYP1 females decreased at an accelerated rate relative to those from the PGYP1.tet strain (ANCOVA, P<0.0001 for both comparisons). As PGYP1 females aged, the average number of larvae produced per female decreased such that by the second cycle a 15% cost to reproductive output was observed relative to uninfected PGYP1.tet females, which progressively declined to a 40% cost by the fifth cycle (t-tests, P<0.05 for all comparisons). A large proportion of PGYP 1 females that were randomly sampled for oviposition at the six and seventh gonotrophic cycles did not produce eggs (FIG. 35C), leading to a further decline in fecundity and fertility of this strain (FIG. 35A and B). This appeared to be due to defects in feeding behaviour, as many of these older PGYP1 females were observed to be unsuccessful in obtaining a blood meal (data not shown). Such a dramatic decrease in oviposition rates was not evident for PGYP1.tet females as they aged (FIG. 35C).

Example 8

*Wolbachia* Infection Reduces Blood-Feeding Success in the Dengue Fever Mosquito, *Aedes Aegypti*

Materials and Methods

Mosquito Rearing

For all experiments two laboratory lines of *Aedes aegypti* were used, the *Aedes aegypti* PGYP1 line, previously generated by transinfection with wMelPop and its *Wolbachia* cured control line, PGYP1.tet (see Example 2). Mosquitoes were reared at 26±2° C., RH 75% with 12 h:12 h light/dark cycle. Larvae were fed 0.1 mg/larvae of TetraMin Tropical Tablets once per day. Females were separated from males at the pupal stage and placed into 300 $mm^3$ cages for emergence at a density of 400 individuals per cage. The females were fed 10% sucrose solution ad libitum until the day before feeding trials.

Confirmation of Infection Status

Mosquito lines were screened to confirm presence (PGYP1) or absence (PGYP1.tet) of infection every two generations using a PCR based assay. Five days after eclosion, DNA was extracted from 10 females using DNeasy spin columns (QIAGEN, Australia), following the Manufacturer's protocol. PCR was then carried out using primers for the IS5 transposable element present in *Wolbachia* (see Example 1). Reaction conditions were as follows: 0.01-0.09 μg of each DNA sample, 2 μl of 10× Buffer, 0.5 μl 1 mM dNTPs, 0.5 μl of 20 μM IS5 primers, 0.15 μl Taq DNA polymerase and water up to 20 μl. Samples were denatured for three minutes at 94° C. then cycled 34 times for 30 seconds at 94° C., 30 seconds at 55° C. and one minute at 72° C. This cycle was followed by a final 10-minute extension at 72° C. in a MJ Research PTC-200 Peltier Thermal Cycler (Geneworks Pty Ltd, SA). Presence of the expected size product was then confirmed by agarose gel electrophoresis.

Preparation for Feeding Trials

Experiments were conducted with five, 26 and 35-day-old adult mosquitoes. Behaviours were measured in either small populations (proportion of population fed, number and length of attempted bites) or for single mosquitoes depending on feasibility (response time to human, blood-meal weight). The afternoon prior to each trial the required number of mosquitoes were removed from their rearing cages and stored in mesh-covered holding buckets at a density of five mosquitoes per bucket. At the same time an additional population of five mosquitoes were set aside to replace any mosquitoes that died during the starvation period. Mosquitoes were starved of sucrose but given access to water for ~16 hours until trials began the next morning. Prior to each trial, mosquitoes were transferred from holding buckets into a 645 $cm^3$ cage and allowed to acclimate for 5 minutes. All human volunteers cleaned both of their forearms with 70% isopropyl alcohol wipes, rinsed their forearms with distilled water and dried them with paper towel, and placed latex gloves on both their hands before feeding.

Population Trials

All population trials were carried out in two cages placed next to one another. One cage contained five PGYP1 mosquitoes and the adjacent cage contained five PGYP1.tet mosquitoes. The position (left or right) of the two lines was randomised throughout the experiment. Volunteers inserted their left and right arms into the respectively into the two cages and rested their hands on buckets placed within each cage. Both the volunteer and an external assistant monitored the number of attempted bites each mosquito made on the volunteer's forearm. An attempted bite was recorded when a mosquito landed and actively attempted to probe the volunteer's skin at a location. A single mosquito could probe multiple times at a single location, but if a mosquito moved to a new position and attempted to probe again this new location was recorded as another attempted bite. Mosquitoes in both cages were monitored for 15 minutes before the volunteer shook their arms and withdrew both arms from the cages. Mosquito abdomens were examined for presence of a blood meal and the proportion of the population that imbibed a blood meal was recorded. This experiment was replicated with six volunteers (3 female, 3 male)×4 replicate trials for each of the three adult mosquito age classes.

Individual Trials

A single mosquito from each line was separately aspirated into on a pre-weighed 1.5 ml Eppendorf tube and weighted on a Satorius BP211D balance (Selby Biolabs). Each mosquito was then released simultaneously into the adjacent 645 mm$^3$ cages. Randomisation of cage position, mosquito settlement time and trial length were as per population trials. The volunteer inserted his arms into the cage and the times at which mosquito's made their first attempted bite (host-seeking time) were recorded by the volunteer into a voice recorder (Olympus VN-1100). After the trial, mosquitoes were transferred back into the tubes they were originally weighed in and the tubes were re-weighed. The weight of the blood-meal imbibed by each mosquito was then calculated. The volunteer (male) hosted four groups of 10 mosquitoes from each of the three age classes.

Statistical Analysis

All analysis was conducted using STATISTICA v8 (StatSoft, Inc). The variables, host-seeking time and blood-meal weight were normally distributed. The number of attempted bites was transformed by square root to achieve normality. The role of infection and age on these variables was examined using general linear mixed models. The role of human volunteer was not examined as there were only 6 replicate individuals and they were internally controlled. When infection status was significant, t-tests were then used to further identify specific differences between infected and uninfected lines within each of the three age classes. The proportion of mosquitoes obtaining a blood meal did not respond to transformation and so non-parametric Mann Whitney U-tests tests were employed instead of linear models to examine differences between infected and uninfected mosquitoes for all three ages.

Results

Host Seeking

Figure 36:
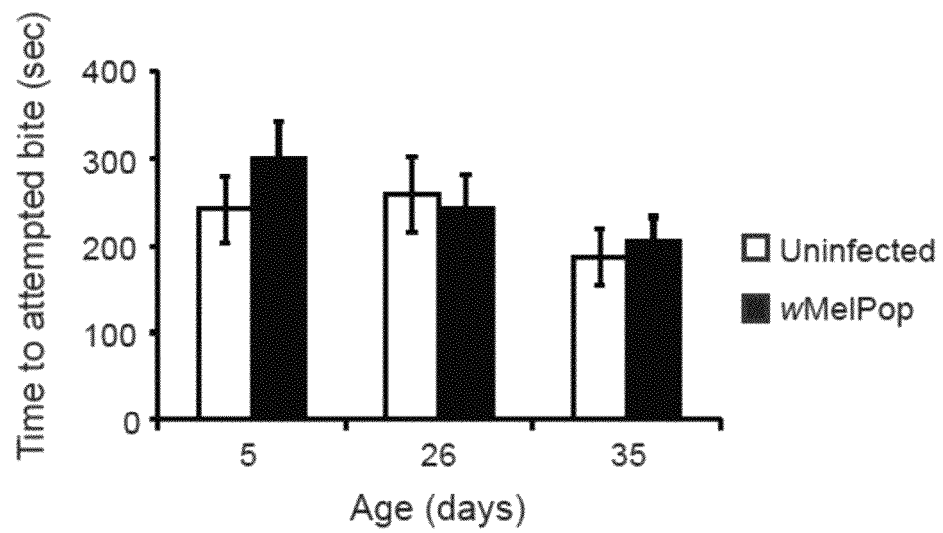
FIG. 36. Time until first attempted bite. Bars represent means±sem from individual trials. No significant differences were observed between infected and uninfected mosquitoes for any of the ages.

If the *Wolbachia* infected mosquitoes were hungrier than uninfected counterparts they might be more rapid in their response to an offered human forearm. Over the short distances in a laboratory cage environment, infected mosquitoes were no different to uninfected controls (F=0.10, df=1, P=0.77) in the time it took them to land on the human volunteer and initiate an "attempted bite" (FIG. 36). Age of the mosquitoes was also not a significant determinant of time to first "attempted bite" (F=0.99, df=2, P=0.43). These data suggest that wMelPop does not alter mosquito capacity to sense and respond to human hosts in the laboratory.

"Attempted Biting"

Figure 37:
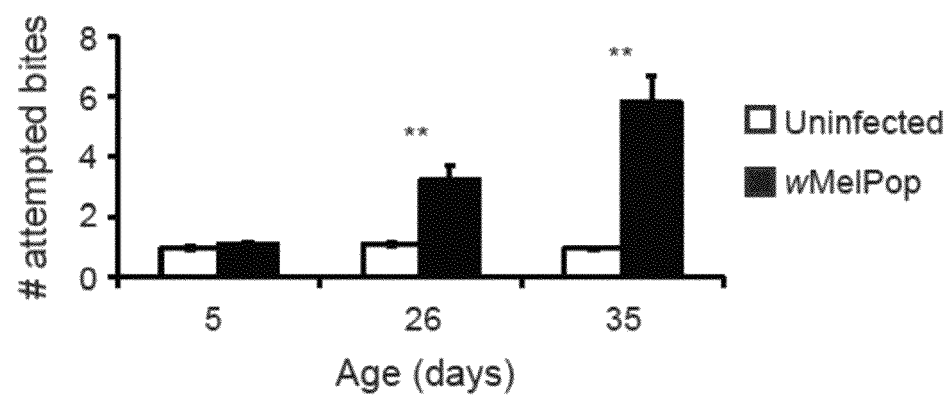
FIG. 37. Number of attempted bites. Bars represent means±sem from population trials. *P<0.05, **P<0.001 by t-test.

The number of "attempted bites" made by infected mosquitoes was examined as a possible indicator of hunger. As per our methods, an attempted bite included both probing and attempted probing in a particular region on the arm. Given the cage sizes and numbers of mosquitoes involved we could not visually differentiate between a probing event that broke the skin and one that did not. See the subsequent associated study by Moreira et al. for dissection of biting behaviour into successful and unsuccessful probing events (see Example 9). Infection status (F=13.37, df=1, P=0.014), age of mosquitoes (F=5.72, df=2, P=0.021), and the interaction between age and infection status (F=5.76, df=2, P=0.021) were significant determinants in the number of attempted bites made. In particular, *Wolbachia*-infected mosquitoes at 26 (t=−3.70, df=238, P<0.001) and 35 days of age (t=−5.35, df=235, P<0.001) attempted to bite more than their uninfected counterparts (FIG. 37). This was not the cased for five-day-old mosquitoes (t=−1.12, df 236, P=0.26). The significant interaction between infection status and age as reported above is seen in the increase in biting attempts by infected mosquitoes in the older age classes (FIG. 37). For example, if we directly compare infected 26-day-old versus 35-day-old mosquitoes we see an increase (t=−2.70, df=235, P=0.0073) in the mean number of attempted bites while this is not the case for uninfected mosquitoes (t=1.72, df=238, P=0.085). Lastly, we also measured the length of time each mosquito spent on an attempted bite (data not shown), which was not influenced by infection status (F=0.75, df=1, P=0.45) or age (F=1.68, df=2, P=0.26) of the mosquitoes. These data suggest that as *Wolbachia* infected mosquitoes age they are exhibiting a greater number of attempted bites than uninfected mosquitoes, but are not spending more time on any one attempt. In a subsequent study (see Example 9), it was shown that *Wolbachia* infected mosquitoes were actually less likely to pierce the skin and obtain a blood meal compared with uninfected mosquitoes and that this effect worsened with age.

Blood Meal Acquisition

Figure 38:
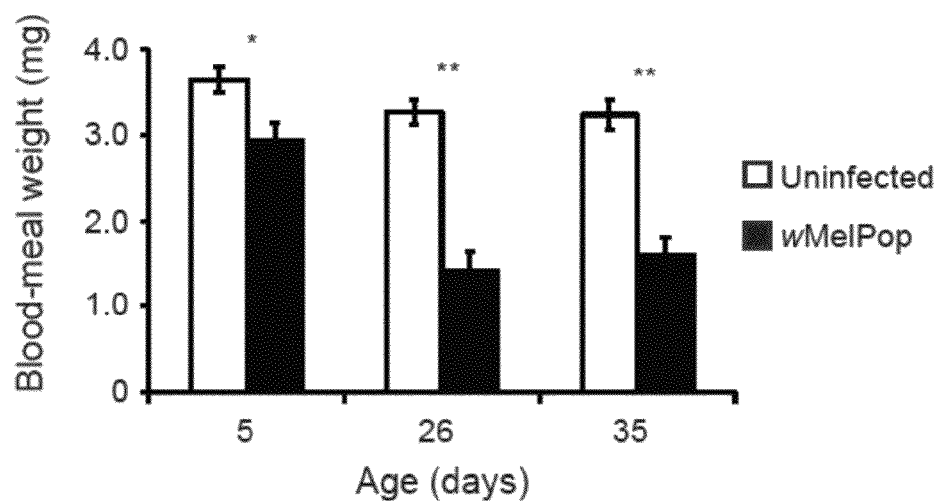
FIG. 38. Weight of imbibed blood meal. Bars represent means±sem from individual trials. *P<0.05, **P<0.001 by t-test.
Figure 39:
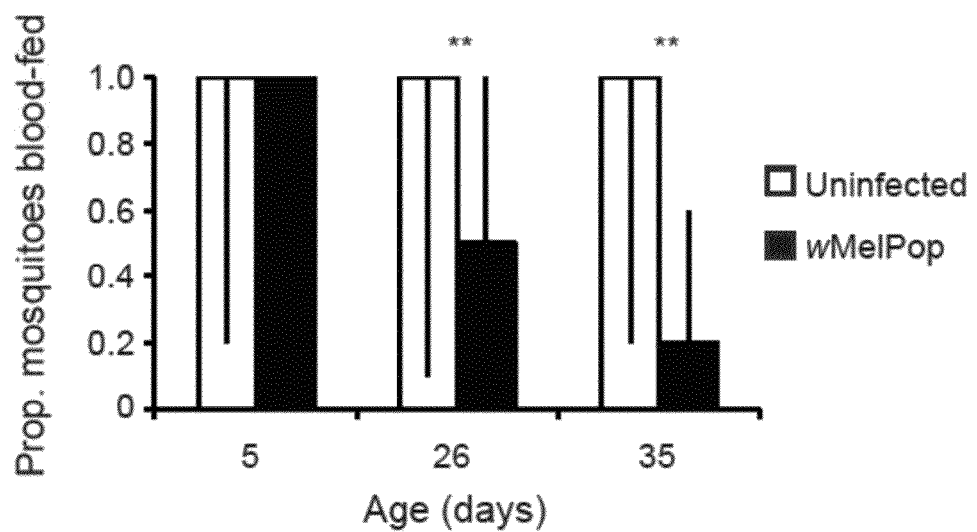
FIG. 39. Proportion of the population that imbibed a blood meal. Bars represent medians±25% and 75% quartile values from population trials. **P<0.001 by Mann Whitney-U test.

Blood-meal weight (FIG. 38) was examined as a measure of feeding success in the infected mosquitoes. Linear models revealed that blood-meal weight could be partially explained by the infection status (F=87.07, df=1, P<0.001) and age of mosquito (F=16.87, df=2, P<0.001). There was also a significant interaction between age and infection status (F=5.59, df=2, P=0.004). The blood-meal weight of wMelPop-infected mosquitoes was smaller than uninfected mosquitoes for all ages examined, (5 d, t=−2.80, df=67, P=0.007; 26 d, t=−7.15, df=67, P<0.001; 35 d, t=−6.09, df=66, P<0.001) with the differential increasing with age (FIG. 38). If infected mosquitoes were on average smaller than their uninfected counterparts, then smaller blood-meal weights would also be expected. A comparison of average weights of the infected and uninfected mosquitoes' pre-blood meal indicated there were no size differences between the lines, PGYP1 and PGYP1.tet (df=204, t=1.57, P=0.11). The median proportion of mosquitoes that imbibed a blood meal (FIG. 39) was also reduced for infected 26 (Z=4.10, P<0.001) and 35-day-old (Z=5.39, P<0.001), but not 5-day-old (Z=0.83, P=0.74) mosquitoes relative to uninfected. These data indicate that as *Wolbachia* infected mosquitoes age, an increasing proportion of the population fails to successfully obtain a blood meal and that when they do feed the meals are smaller.

Behavioural Observations

Normally during biting a mosquito may probe unsuccessfully, but will ultimately insert its stylet into a host. In this study, infected mosquitoes were observed in which the proboscis repeatedly bent as the mosquito pushed its head towards the skin while probing. This phenotype appeared to be correlated with old age and poor ability to obtain a blood meal. Due to its correlation with old age, the behaviour was not observed in the study until much of the other work was completed, hence its quantification and correlation with biting success is reported in another study (see Example 9).

Example 9

Human Probing Behaviour of *Aedes Aegypti* when Infected with a Life-Shortening Strain of *Wolbachia*

Materials and Methods

Mosquitoes

*Aedes aegypti* mosquitoes, wMelPop infected (PGYP1) and its Tetracycline-cured counterpart (PGYP1.tet) (see Example 2), were kept in a controlled environment insectary at 25° C. and 80% RH. Larvae were maintained with fish food pellets (Tetramin, Tetra) and adults were offered 10% sucrose solution, ad libitum. Adult females were fed on human blood for egg production and eggs were dried for at least 96 h prior to hatching.

Behaviour Assays

Fertilized and non-blood fed females of different ages (5, 15, 26 and 35 days old) were used in all behaviour experiments. Sucrose solutions were removed from cages on the night before the experiments. Forty females were used per age and per infectious status. Single mosquitoes were transferred to a transparent Perspex cage (25 cm$^3$) and filmed through a digital camera with 6 mm Microlens (IEEE-1394, Point Grey Research) mounted on a tripod. Mosquitoes were given about five minutes to settle within the cage before a human gloved-hand was inserted into the cage. A window of about 15 cm$^2$ was cut of the upper part of the latex glove in order to delineate the probing field.

Movies were recorded (QuickTime Player) for a maximum of 10 minutes or until blood was seen within the mosquito midgut and subsequentially watched for time calculations. Two electronic timers were used, one for recording pre-probing time and the second for probing time. Pre-probing time was defined and the time since the mosquito has landed on the bare hand area until the insertion of mouthparts into the human skin. Probing time is defined as the initial insertion of insect mouthparts until blood can be seen within the mosquito midgut through the abdominal pleura (Ribeiro et al., 1984). Timing stopped when mosquitoes left the bare hand area or withdrew their mouthparts before taking blood and began again when the mosquito came back or after subsequent stylet penetration. If blood was not found by the end of 10 minutes, we defined this case as unsuccessful probing and it was measured as a proportion. Movies were also used to visualize additional abnormal phenotypes as the jittering action of mosquito body while landed on top of the human hand, and named "shaky". Furthermore, the inability of mosquitoes to insert their mouthparts due to a bendy proboscis (Example 8) was also analysed.

Mosquito Saliva Collection

Mosquitoes of different ages (5, 26 and 35-days-old) and infectious status were starved overnight (without sucrose solution or water). On the following morning mosquitoes were briefly anesthetized with $CO_2$ and placed on a glass plate over ice. Wings and legs were removed with forceps and their proboscis introduced into a 1 cm piece of polypropylene tubing (0.61×0.28 mm, Microtube Extrusions, NSW, Australia) (see Ribeiro et al., 1984). Females were allowed to salivate for 5 minutes and then the diameter of the saliva droplets was measured through an ocular micrometer at 40× magnification. Volumes were calculated via the sphere formula (Novak et al., 1995). Saliva was then collected into 20 μL of 0.05 mM Tris-HCl pH 7.5 by attaching the needle of a 10 μL Hamilton syringe and rinsing the tubing content a few times. Samples were centrifuged at 14,000 g for 2 minutes and kept frozen (−80° C.) in 20 μL of 0.05 mM Tris-HCl, pH 7.5 for enzymatic assay (see below).

Apyrase Assay

Saliva samples (8 μL) were transferred, in duplicates, into individual wells of a plastic 96-well ELISA plate (NUNC Maxisorp). For the blank, 8 μL of the 0.05 mM Tris buffer was added to the wells. To each well, 100 μL was added of a mixture containing 100 mM NaCl, 50 mM Tris-HCl (pH 8.95), 5 mM $CaCl_2$, 2 mM ATP and 20 mM B-Mercapthanol. The plate was incubated at 37° C. for 10 min and then the reaction was immediately stopped, by adding 25 uL of acid molybdate solution (1.25% ammonium molybdate in 2.5 mM $H_2SO_4$). Immediately after termination of the reaction, 2 μL of a reducing solution (0.11 mM $NaHSO_3$, 0.09 mM $Na_2SO_3$ and 8 mM 1-amino-2-naphthol-4-sulphonic acid) was added to each well and the plate was incubated at 37° C. for 20 min (Novak et al., 1995). Plates were read at a FLUOstar OPTIMA ELISA plate reader (BMG Technologies) at 660 nm. Readings were quantified by comparison with an inorganic phosphate standard curve (1, 0.5, 0.25, 0.125, 0.06125, 0.03125, 0.015625 mM of sodium phosphate).

PCR Confirmation of Mosquito Infection Status and Saliva Screening

Wolbachia infection was confirmed through PCR to detect both mosquito (apyrase gene: ApyF: 5'-TTTCGACGGAA-GAGCTGAAT-3' (SEQ ID NO: 18) and ApyR: 5'-TCCGT-TGGTATCCTCGTTTC-3' (SEQ ID NO: 19)) and Wolbachia (IS5-F: 5'-CTGAAATTTTAGTACGGGGTAAAG-3' (SEQ ID NO: 20) and IS5-R: 5'-CAAGCATATTCCCTCTTTAAC-3' (SEQ ID NO: 21)) sequences. Saliva screening to check the presence of Wolbachia was done via PCR (with IS5 primers) using saliva samples of infected and non-infected mosquitoes. Mosquito sequences in this case were detected with primers for the ribosomal protein gene RpS 17 (Cook et al., 2006).

Statistical Analysis

In all cases, general linear models were employed to examine the effects of the variables age and infection status and their interaction with one another. Models demonstrating significance for the variable infection status were then followed by individual t-tests examining the differences between infected and uninfected mosquitoes for each age class. The proportion of infected and uninfected mosquitoes that obtained blood meals were examined using Mann-Whitney U tests instead of linear models, given the deviation of the data from normality. Chi-square 2×2 contingency tests were employed to examine the relationship between observed behavioural traits and lack of feeding success. The correlation between these traits was quantified using a cox-proportional hazards model for age, with the behavioural traits and lack of blood meal success covariates. All statistical analyses were carried out in STATISTICA v8 (StatSoft, Inc. Tulsa, Okla.).

Results

Pre-probing Time

Figure 40:
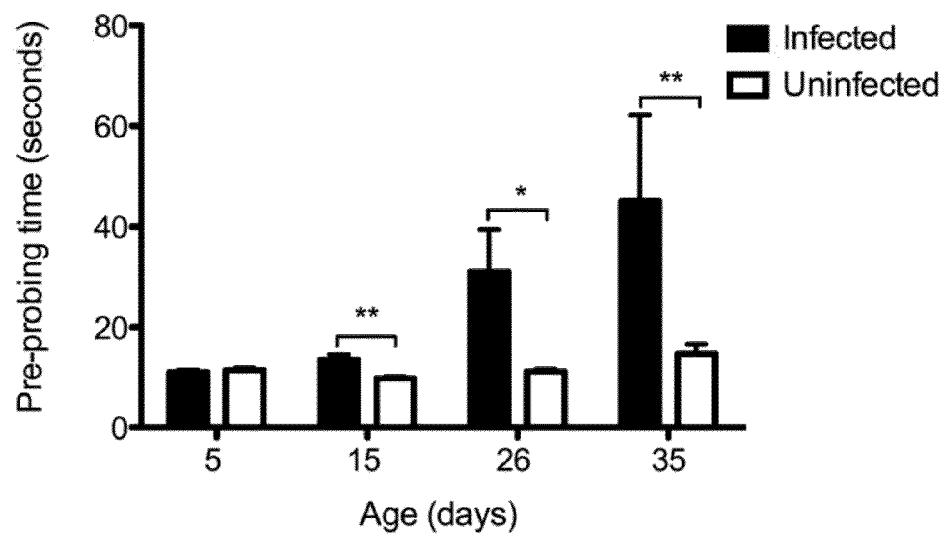
FIG. 40. Pre-probing behaviour of $A. aegypti$ mosquitoes.

We measured the time mosquitoes spent from first contact with a human volunteer until the insertion of the insect's mouthparts as a measure of pre-probing time. All feeding trials were carried out with individual mosquitoes, which had been starved prior to the assay, at four adult ages (5, 15, 26 and 35-days-old). Mosquitoes that never successfully achieved a blood meal were excluded from this analysis. Overall both age (df=3, F=13.73, P<0.0001) and infection status (df=1, F=23.18, P<0.0001) had a significant effect on the length of pre-probing time. On average infected mosquitoes spend more time pre-probing especially as they age (FIG. 40). This change with age is clearly exhibited by a significant interaction between the variables age and infection status (df=3, F=8.11, P<0.0001). At five days of age infected and uninfected mosquitoes do not differ in their pre-probing time (df=78, t=0.63, P=0.52), which lasted on average 11 seconds. Uninfected mosquitoes maintained the same foraging time as they aged, while wMelPop insects exhibited a steady and significant increase (15 d: df=75, t=−3.37, P=0.0012; 26 d: df=63, t=−4.17, P=0.014; 35 d: df=48, t=−2.25, P=0.0034), reaching a mean length of 45 sec by 35 days of age (FIG. 40).

Probing Time

In the same feeding trials described above, the length of time between insertion of mouthparts and the first visible sign of blood in the abdominal pleura (Ribeiro et al., 1984) was recorded as probing time for the mosquitoes. As with pre-probing time, the variables of age (df=3, F=11.36, P<0.0001), infection status (df=1, F=29.46, P<0.0001) and the interaction (df=3, F=10.56, P<0.0001) between these two variables were highly significant. Infected and uninfected mosquitoes did not differ in their probing time (~33 sec) at 5 (df=78, t=−0.46, P=0.64) and 15 (df=75, t=1.43, P=0.15) days of age (FIG. 41). In contrast, infected mosquitoes at 26 (df=63, t=−3.76, P<0.001) and 35 (df=48, t=−4.06, P<0.001) days of age took significantly longer during probing, exhibiting up to a seven-fold increase in their probing time relative to uninfected mosquitoes (FIG. 41).

Blood Meal Acquisition

In the assays detailed above we then compared the ability of infected and uninfected mosquitoes to obtain blood meals (FIG. 42) using Mann-Whitney U tests. At 5 (Z=0, P=1) and 15 (Z=0, P=1) days of age infected and uninfected mosquitoes did not differ in their success. At 26 (Z=−2.39, P=0.020) and 35 (Z=−2.39, P=0.020) days of age infected mosquitoes were less successful at obtaining blood meals in comparison to their uninfected counterparts.

Number of Probings

It is important to note that as infected mosquitoes aged, the frequency of events where they pierced the skin did not increase despite failed attempts at feeding (FIG. 43). A general linear model revealed that age (df=3, F=20.47, P<0.0001), infection (df=3, F=29.12, P<0.0001) and age X infection (df=3, F=27.18, P<0.0001) were significant determinants of the number of probings. Subsequent t-tests comparing the number of probings between infected and uninfected mosquitoes at each of the age points (data not shown), however, demonstrated that only 35 day old (df=1, t=−8.44, P<0.0001) mosquitoes differed. In this case, uninfected females probed more on average per session (1.05±0.05) than wMelPop infected mosquitoes (0.3±0.073). This is due to other behaviours, which impaired the infected mosquitoes to feed (see below).

Additional Behavioural Phenotypes

In other work we have reported the appearance of a "bendy" proboscis in association with wMelPop, which was the inability of the mosquito to properly orient its mouthparts and insert the stylet into the skin (Example 8). During the feeding trials in this study we quantified the occurrence of this trait. The bendy proboscis was never observed in any of the uninfected mosquitoes regardless of age, nor was it present in 5 day-old infected mosquitoes. The trait first appeared at a low level (2.5%) in 15 day-old mosquitoes and rose to a frequency of 65% by 35 days of age (FIG. 44). Another phenotype observed, although in lower frequencies, was the jittering action of the insect body (named here as "shaky") when the mosquito was sitting on top of the human hand (FIG. 44). The association between each of these traits and lack of success in blood meal acquisition was explored using 2×2 contingency tests in each of the age classes where the trait was expressed. There was a significant association between the failure to obtain a blood meal and both the bendy phenotype (26 d: df=1, χ2=14.1, P=0.0002; 35 d: df=1, χ2=11.8, P=0.0006) and the shaky phenotype (35 d: df=1, χ2=4.2, P=0.038). Using survival analysis we obtained estimates of the correlation between lack of feeding success and the bendy phenotype (0.63) and the shaky phenotype (0.19). These correlations reveal the presence of a relationship between the traits and success in feeding, but do not completely explain lack of success. There are mosquitoes in the older age classes that fail to feed and that are not shaky or bendy. To discard any possibility that this other abnormal phenotypes were due to the lack of blood feeding, which could have physiologically compromised the mosquitoes we also blood fed females of both groups when they were 3 to 5-days-old and then after 38 days evaluated their feeding behaviour. None of the wMelPop mosquitoes were able to feed and all presented the bendy proboscis, although all the tetracycline-treated mosquitoes successfully imbibed blood (data not shown).

Saliva Volume and Apyrase Activity

To check whether the probing behaviour and the additional phenotypes we observed were due to differences in saliva volume and salivary gland apyrase activity we measured both traits in infected and uninfected mosquitoes at three adult ages. Apyrase activity (FIG. 45A) did not differ in infected and uninfected mosquitoes regardless of age (df=1, F=0.44, P=0.51). Infection status (df=1, F=11.99, P<0.01) and age (df=2, F=14.54, P<0.0001), however, were determinants of saliva volume (FIG. 45B) and on average infected mosquitoes produced less saliva. When saliva volumes of infected and uninfected mosquitoes were compared to each other for each age class, only the 26 days old mosquitoes were significantly different (df=1, t=−2.9, P<0.01).

Evidence of *Wolbachia* in the Saliva

In an attempt to interpret the effects of *Wolbachia* on host-feeding behaviour we tested for the presence of *Wolbachia* in the saliva and salivary glands of infected mosquitoes. PCR amplification of the *Wolbachia* wsp gene or mosquito apyrase has shown only the presence of *Wolbachia* in salivary glands, but not in saliva (FIG. 46. The transposable element IS5, present in at least 13 copies within the bacteria genome (Wu et al., 2004), was also used in extra samples as a very sensistive PCR target (N=16 of each group) but no amplification was obtained. These results are supported by the size of the intracellular *Wolbachia* (around 1 μm in diameter) (Min and Benzer, 1997) and the diameter of mosquito salivary ducts (also about 1 μm) (Janzen and Wright, 1971), which indicate that even if *Wolbachia* was able to be present in the secreted salivary fluid it would be unlikely to be able to freely move through the salivary ducts.

Example 10

Unique Genetic Features of the Life-Shortening wMelPop-CLA *Wolbachia* Strain

We have recently sequenced the complete wMelPop and wMelPop-CLA genomes and we have identified, by using a comparative genomics approach, a series of mutations that have occurred during the 3 years in cell culture. These mutations are part of the wMelPop-CLA strain present in the transinfected *Aedes aegypti* mosquitoes.

The wMelPop-CLA strain has at least 5 major genetic differences with the original wMelPop strain. These differences include gene insertions, deletions and single nucleotide polymorphisms (SNPs). The combination of these 5 elements is unique to wMelPop-CLA and can be used to differentiate this strain from any other *Wolbachia* strain, including very closely related strains such as wMelCS. As a result of these genetic differences, the wMelPop-CLA genome is approximately 20952 bp smaller that wMelPop (1247197 bp vs 1268149 bp).

wMelPop-CLA Unique Genetic Features

SNP in Gene WD0200

The gene WD0200 encodes for a hypothetical protein, according to the wMel genome annotation (Wu et al., 2004). During the adaptation of wMelPop to mosquito cell culture in our laboratory, the sequence of this gene has mutated resulting in the substitution of a C residue for a T in wMelPop-CLA (FIG. 47). This nucleotide change results in the replacement of an aspartic acid (D) for asparagine (N) in the C-terminus of the encoded protein. The presence of this mutation has been confirmed by PCR and sequencing of the wMelPop and wMelPop-CLA strains.

10 Bp Deletion in Gene WD0413

Gene WD0413 encodes an aspartyl-tRNA synthetase (aspS) [6.1.1.12] involved in protein biosynthesis. Following the sequencing of wMelPop and wMelPop-CLA WD0413 we have identified a 10 bp deletion in wMelPop-CLA that was not present prior to cell culture adaptation (FIG. 48).

This 10 bp deletion occurs just before the TGA stop codon and creates a frameshift that extends the wMelPop-CLA encoded protein by an extra 10 aminoacids before a new stop codon is read (FIG. 49).

IS5 Element Insertion

IS5 insertion elements are common transposable elements identified in several *Wolbachia* genomes. The IS5 insertion element is 918 bp long and is constituted by two ORFs (OrfA and B), flanked by a terminal inverted repeat. The closely related wMel *Wolbachia* genome, (Wu et al., 2004), contains 13 identical IS5 elements. wMelPop also contains 13 IS5 elements, although 2 of them have translocated when compared to wMel.

The novel IS5 insertion present in the wMelPop-CLA strain is located in the intergenic region between the genes WD0765 and WD0766 (FIG. 50). WD0765 encodes a Na/H+ ion antiporter family protein, whereas WD0766 encodes an ankyrin domain protein. The role of both proteins in *Wolbachia* is currently unknown, although the expression of these two genes is probably affected by the insertion of this IS5 element in the middle of their promoter region.

21.6 Kb Deletion

The wMelPop-CLA strain contains a 21.6 Kb deletion when compared to the original wMelPop strain (FIG. 51). This deletion includes 13 genes (WD0506 to WD0518), whose putative function is listed in Table 7. Since the 2 genes flaking the deletion (WD0506 and WD0518) are the result of a duplication event and have similar sequences, the exact coordinates of the 21.6 kb deletion are difficult to determine. Several of the genes present in the deletion have homologues elsewhere in the genome, and 3 of them (WD0512, WD0513 and WD0514) are part of an operon in those strains (wMel, wMelPop, wMelCS) where the genes are present.

The presence of a similar 21.6 Kb deletion was previously described by our group in the wAu *Wolbachia* strain (Iturbe-Ormaetxe et al., 2005), although none of the other four wMelPop-CLA unique features have been found in wAu.

We have also identified WD0513 as a potential candidate for horizontal gene transfer between mosquitoes and *Wolbachia* (Woolfit et al., 2009).

Insertion of a G in Gene WD0758

Gene WD0758 encodes for a glutaredoxin family protein. This gene contains an extra G at position 196 in wMelPop-CLA when compared with its counterpart in wMelPop. This mutation creates a premature stop codon in wMelPop-CLA and as a consequence, the WD0758 protein is 46 residues shorter in wMelPop-CLA than in wMelPop (FIG. 52). The effect of this mutation on the function of WD0758 is currently unknown.

PCR Characterization of Unique wMelPop-CLA Features

Three of the 5 described genetic features that distinguish wMelPop-CLA from its predecessor wMelPop can be easily identified and diagnosed by PCR, as shown in FIG. 53. The identification of the SNP in WD0200 and the insertion of a G in WD0758 require PCR-amplification and sequencing.

Discussion

The use of an in vitro cell culture system provided an ideal means to examine the adaptation of *Wolbachia* to a novel host environment. This approach contrasts with directly transferring *Wolbachia* between insects, where selective forces are presumably different and more complex, and where longer insect generation times, vertical transmission, and the labour intensive nature of rearing live insects make selection for transinfected lines challenging.

The initial difficulty in establishing wMelPop infection in the *Aedes albopictus* cell line Aa23 demonstrated that wMelPop was not naturally pre-adapted for growth in mosquito cells. Following stable infection of Aa23 and serial passage for several years, wMelPop was successfully established in *Aedes aegypti* RML-12 and *Anopheles gambiae* MOS-55 cell lines, two species that are not naturally infected by *Wolbachia* (Curtis and Sinkins, 1998; Kittayapong et al., 2000; Rasgon and Scott, 2004; Ricci et al., 2002; Tsai et al., 2004). Transfer of wMelPop between Aa23 and these two mosquito cell lines occurred much more readily than the initial transfer from *D. melanogaster* to Aa23, potentially due to (i) a higher infective dose of wMelPop purified from Aa23 and used for transfer; and (ii) a smaller divergence in intracellular environments among these mosquito cell lines as opposed to the initial transfer from *Drosophila*. The cell line-adapted *Wolbachia* displayed reduced infectivity and maternal transmission when injected back into its original *Drosophila* host. It grew to lower densities and showed phenotypic shifts for both life-shortening and CI expression. Taken together, these results provide evidence for the active genetic adaptation of wMelPop to mosquito cell lines during long-term serial passage.

A comparison of results from this study, with simulations from recent theoretical models that examine the potential of life-shortening *Wolbachia* to modify mosquito population age structure (Brownstein et al., 2003; Rasgon et al., 2003), suggests that wMelPop should be able to initiate a population invasion of *A aegypti*. Given the relationship that exists between mosquito survival and vectorial capacity (Garett, 1964; MacDonald, 1957), if the longevity of adults *A aegypti* can be approximately halved under field conditions, as observed in our laboratory experiments, then the introduction of life-shortening *Wolbachia* strains would be predicted to reduce pathogen transmission and the incidence of human disease.

Vertically inherited parasites like *Wolbachia* are predicted to evolve towards reduced virulence over time (Lipsitch and Moxon, 1997). Unlike chemical insecticides, biological agents that induce mortality in late life, such as wMelPop or entomopathogenic fungi, are expected to impose relatively weak selection pressures for the evolution of resistance (Thomas and Reed, 2007). This is because the majority of individuals in the population are able to initiate several reproductive cycles prior to death, minimizing costs to reproductive output. Moreover, since the initial description of wMelPop in *D. melanogaster* over ten years ago, no signs of resistance to life-shortening have emerged in laboratory stocks.

Furthermore, our finding that the wMelPop *Wolbachia* infection eliminates the ability of dengue virus to establish a productive infection has significant implications for any future control measure based on the use of life-shortening *Wolbachia*. Life-shortening effects on mosquitoes would become secondary and only act on any rare individuals that might escape the direct interference effect. We could also presume that because of the observed effects on dengue virus accumulation that any mosquitoes that did escape the interference effect despite the presence of *Wolbachia* would likely have extended extrinsic incubation periods. This in turn would act synergistically with the life-shortening effect to eliminate dengue virus transmission.

Our recent studies have also revealed that, as *A. aegypti* infected with wMelPop-CLA age, they show increasing difficulty in completing the process of blood feeding effectively and efficiently. These effects on blood feeding behaviour may reduce vectorial capacity and point to underlying physiological changes in *Wolbachia*-infected mosquitoes.

Thus, the ability of *Wolbachia* to spread into *A aegypti* and *A. anopheles* populations and persist over time may provide an inexpensive approach to dengue and malaria control, particularly in urban areas that are less amenable to conventional control strategies. Given the ability of wMelPop to induce life-shortening, cytoplasmic incompatibility, altered feeding behaviour, and reduced pathogen susceptibility in a range of insect hosts, this strategy may be broadly applicable to reduce pathogen transmission by other insect disease vectors of medical or agricultural importance.

The fact that many insect species are infected with *Wolbachia* raises the possibility that *Wolbachia*-mediated antiviral protection could be a widespread phenomenon. To test the generality of *Wolbachia*-mediated antiviral protection further, the inventors used *D. simulans* and its naturally occurring *Wolbachia* infections.

*Wolbachia* strains vary both between host species and within a host species (see for example Casiraghi et al., 2005). Naturally occurring *Wolbachia* strains in *D. melanogaster* ubiquitously protect against DCV (see Example 4 and Teixeira et al., 2008), however these strains are very closely related (Riegler et al., 2005). *Wolbachia* is maternally inherited and therefore has a close association with its host. Using *D. simulans* fly lines that are naturally infected by different *Wolbachia* strains we showed that some strains did not mitigate virus-induced mortality. Strains wAu and wRi protected the CO and DSH host flies respectively. In contrast, neither wHa nor wNo protected their host lines from DCV induced mortality. Phylogenetic analysis indicates that the *D. simulans Wolbachia* strains wAu and wRi are most similar to wMel. Whereas of the phylogenetic supergroup A strains, wHa is the most divergent to wMel, and wNo belongs to supergroup B (Zhou et al., 1998; Casiraghi et al., 2005). This may suggest that there is a *Wolbachia* feature involved in antiviral protection, which is conserved among strains more closely related to wMel.

With the exception of the Me29 flies infected by wMel, natural host-*Wolbachia* combinations were used. The *D. simulans Wolbachia* strains are known to be associated with different mitochondrial haplotypes (Ballard, 2000) and we did not control for host nuclear genetic background which can have an impact on virus infection (Teixeira et al., 2008). As a consequence it is not possible to rule out that intrinsic variability in susceptibility to virus that is linked to the host background has an influence on the outcome of *Wolbachia*-mediated protection in our experiments. Indeed there is variation in the time to death of *Wolbachia*-free *D. simulans* lines used in this study when challenged with DCV (see FIG. 19), although interestingly these same *Wolbachia*-free lines showed similar time to death when challenged with FHV (see FIG. 21). Antiviral protection was observed in both *D. melanogaster* and *D. simulans* when infected with wMel. This indicates that antiviral protection mediated by *Wolbachia* can be transferred between different host species.

Since protection against DCV was not seen in all the fly lines infected with the *Wolbachia* strains, we tested whether there is specificity in protection against different viruses. Infection of *D. melanogaster* by *Wolbachia* protected the flies from all RNA viruses tested (see Example 4 and Teixeira et al., 2008). Although each of these viruses was a non-enveloped, positive sense RNA virus, the viruses come from a broad spectrum of virus families. Compared to DCV the most divergent of these viruses is FHV. DCV is a member of the Dicistroviridae family and has a single genomic RNA that is not capped but is polyadenylated (Christian et al., 2005). The genome is a bicistronic mRNA from which the structural and non-structural polyproteins are translated via internal ribosome entry sites (Wilson et al., 2000; Johnson and Christian, 1998; Sasaki and Nakashima, 1999). DCV RNA replication occurs on membranes derived from the golgi (Cherry et al., 2006). In contrast, the nodavirus FHV genome comprises two mRNA sense RNAs which are capped but not polyadenylated and a third subgenomic RNA is synthesised during replication (Ball and Johnson, 1998). FHV genome replication occurs on mitochondrial membranes (Kopek et al., 2007; Miller et al., 2001). Interestingly, although DCV and FHV have distinct infection cycles the same *Wolbachia* strains protected *D. simulans* lines from both DCV and FHV induced mortality. This suggests that the mechanism of protection from virus-induced mortality may be common across diverse viruses, although it is not currently known what the mechanism of viral pathogenesis is in flies infected with either DCV or FHV. It remains to be seen whether the same host-*Wolbachia* combinations that do or do not protect against DCV and FHV have similar outcomes for other viruses, or indeed other types of pathogens.

Concurrent with protection from virus induced mortality in *D. melanogaster* was a delay in accumulation of DCV (see Example 4). Here a similar result was seen with wMel protection in *D. simulans*, the amount of infectious virus accumulated 2 dpi was significantly lower in *Wolbachia* infected flies. By 10 dpi the DCV titre in *Wolbachia* infected flies was similar to the day 2 titre for *Wolbachia*-free flies. This may suggest that the resistance to DCV accumulation protects the flies from DCV induced mortality, however, the results observed with the *D. simulans Wolbachia* strains complicate this interpretation. The CO flies infected with wAu survived DCV infection beyond 30 dpi, whereas the *Wolbachia*-free flies were clearly susceptible to DCV-induced mortality. wAu infected flies had by 10 dpi accumulated high titres of DCV and the virus titre remained high at 30 dpi. This shows that wAu infected flies were tolerant of DCV infection, that is the virus accumulated but did not cause mortality (Schneider and Ayres, 2008). Interestingly, although wRi-infected DSR flies were protected from DCV induced mortality, at 2 dpi there was no difference in virus accumulation in flies with and without wRi. We cannot rule out that accumulation was delayed in wRi-infected flies earlier than 2 dpi.

Taken together our results indicate that *Wolbachia*-mediated antiviral protection could arise in flies in two ways. *Wolbachia* can interfere with the virus infection cycle to delay virus accumulation, that is, it can induce resistance to virus infection in the host. In addition *Wolbachia* infection can protect flies from the pathogenesis associated with virus infection, that is, it can increase host tolerance to virus infection. The processes or mechanisms involved in resistance and tolerance may be the same, independent or overlap. Our results show that *Wolbachia* strains can induce both resistance and tolerance to DCV infection, but importantly prolonged resistance is not a requirement for protection against DCV-induced mortality. These results are consistent with those reported for FHV in *Wolbachia* infected *D. melanogaster*, where there was no difference in FHV accumulation 6 dpi but *Wolbachia* infection protected flies from FHV induced mortality (Teixeira et al., 2008).

The strains of *Wolbachia* that mediate antiviral protection were anticipated to be present at higher density in infected flies (Giordano et al., 1995; Sinkins et al., 1995). We confirmed the density of *Wolbachia* in the particular fly lines used in this study correlated with protection. The density of *Wolbachia* was assayed in whole flies as previous assays have shown that in addition to reproductive tissues somatic tissues are commonly infected with *Wolbachia* (Dobson et al., 1999; Ijichi et al., 2002). Further experiments controlling the density of a single strain are required to determine if high *Wolbachia* density is a pre-requisite for antiviral protection.

The mechanisms or processes by which *Wolbachia* protects the host from virus are not yet understood. The correlation of high bacterial density of the strains that protect the host suggests that *Wolbachia* density may be important for antiviral protection. Potentially protection may require a threshold of *Wolbachia* density to be exceeded, which would be consistent with protection being a consequence of competition between the two intracellular microbes for limited host resources. Antiviral protection may also be dependent on the distribution of *Wolbachia* between tissue or cell types. *Wolbachia* have been identified in a range of somatic and reproductive tissues in insects and are known to display variable tissue tropism depending on infecting strain and host combination (Dobson et al., 1999; Ijichi et al., 2002; Miller and Riegler, 2006). Late in infection DCV is widely distributed in *Drosophila* tissues including both reproductive and somatic tissues (Cherry and Perrimon, 2004; Jousset et al., 1972; Lautie-Harivel and Thomas-Orillard, 1990), giving abundant opportunity for overlap with *Wolbachia* distribution. However, little is known about the spread of virus from the initial infection site or if replication of the virus is equivalent in all of the susceptible tissues. It is possible that there are tissues or cell types that are critical to virus replication or pathogenesis and that *Wolbachia*-mediated protection occurs by exclusion or regulation of virus in these tissues. In addition, if particular tissues are critical for pathogenesis, tolerance may be a result of protection of those tissues.

The relatively close phylogenetic relationships of the strains that do confer antiviral protection compared to non-protective strains, suggests that other features of the *Wolbachia* strains could determine the outcome of virus infection. Protection via both resistance and tolerance could be induced by modulation of host antiviral responses by *Wolbachia*. For example, proteins from the ankyrin family, which can play a role in innate immune pathways, vary considerably both in number and sequence between *Wolbachia* strains (Duron et al., 2007; Iturbe-Ormaetxe et al., 2005; Walker et al., 2007). Interestingly defence against bacterial infection in flies via the melanisation response has been shown to involve both resistance and tolerance effects (Ayres and Schneider, 2008).

*Wolbachia* are able to rapidly invade host populations and are often maintained at high prevalence in these populations (Turelli and Hoffmann, 1991). In many cases this is achieved at least in part by *Wolbachia* manipulation of host reproductive systems to increase the prevalence of infected individuals in the host population. For example the *Wolbachia* strains wRi, wHa and wNo used in this study induce cytoplasmic incompatibility in *D. simulans*. However, wAu does not manipulate host reproductive systems (Hoffmann et al., 1986; Mercot and Poinsot, 1998; O'Neill and Karr, 1990; Turelli and Hoffmann, 1995). In the absence of strong reproductive parasitism, theory predicts that to be maintained in a host population *Wolbachia* must provide a fitness advantage to the female host (see for example review by Haine, 2008). *Wolbachia*-mediated protection from viruses and other pathogens (Panteleev et al., 2007) may confer this fitness advantage. It is therefore likely that the interactions between *Wolbachia* and viruses such as DCV impact on the distribution of both microbes in insect populations.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

Tables

TABLE 1

Effect of male age on cytoplasmic incompatibility. Percent embryo hatch ± standard error and number of replicate crosses are shown for incompatible crosses between uninfected PGYP1.tet females and aged PGYP1 males; and control crosses with aged PGYP1.tet males (minimum 2700 embryos total counted per cross).

| Cross (Female × Male) | Male age | | |
|---|---|---|---|
| | 3 d | 10 d | 17 d |
| PGYP1.tet × PGYP1 | 0.00 ± 0.00% (n = 32) | 0.00 ± 0.00% (n = 35) | 0.00 ± 0.00% (n = 35) |
| PGYP1.tet × PGYP1.tet | 86.86 ± 3.42% (n = 34) | 83.67 ± 2.07% (n = 33) | 88.30 ± 3.10% (n = 32) |

TABLE 2

Fly lines and *Wolbachia* strains

| *Drosophila simulans* line | *Wolbachia* strain | Reference |
|---|---|---|
| Me29 | wMel | Poinsot et al., 1998 |
| CO | wAu | Hoffmann et al., 1996 |
| DSR | wRi | Hoffmann et al., 1986 |
| DSH | wHa | O'Neill and Karr, 1990 |
| N7NO | wNo | Mercot and Poinsot, 1998 |

TABLE 3

Effect of *Wolbachia* on DENV-2 infection. *A. aegypti* were orally infected with fresh DENV-2 and viral load determined by cell culture ELISA.

| | | | PGYP1.out | | PGYP1.out.tet | | Cairns3 | |
|---|---|---|---|---|---|---|---|---|
| Experiment | Log DENV-2 per mL | Days post-infection | % body infection (n) | % disseminated infection (n) | % body infection (n) | % disseminated infection (n) | % body infection (n) | % disseminated infection (n) |
| 1 | 6.3 | 7 | 0 (25) | 0 (25) | NA[a] | NA | 64 (25) | 12 (25) |
|   |     | 14 | 0 (27) | 0 (27) | NA | NA | 57 (30) | 23 (30) |
| 2 | 6.0 | 7 | 0 (40) | 0 (40) | 100 (30) | 10 (30) | 95 (40) | 5 (40) |
|   |     | 14 | 0 (40) | 0 (40) | 97 (30) | 37 (30) | 95 (40) | 20 (40) |
| 3 | 5.3 | 7 | 0 (40) | 0 (40) | 30 (40) | 23 (40) | 50 (40) | 13 (40) |
|   |     | 14 | 0 (40) | 0 (40) | 48 (40) | 43 (40) | 73 (40) | 33 (40) |
| 4 | 7.8 | 7 | 5 (40) | 3 (40) | 78 (40) | 63 (40) | 63 (40) | 45 (40) |
|   |     | 14 | 8 (40) | 5 (40) | 70 (40) | 65 (40) | 75 (40) | 70 (40) |

[a] This mosquito line was unavailable for experiment 1

TABLE 4

Effect of *Wolbachia* on CHIKV infection. *A. aegypti* were orally infected with fresh CHIKV and viral load ($Log_{10}$) determined by quantitative RT-PCR in mosquito bodies and heads or wings and legs (for viral dissemination). Median copy number is based only on mosquitoes that were positive for virus.

| | PGYP1.out | | | | PGYP1.out.tet | | | | Cairns3 | | | |
|---|---|---|---|---|---|---|---|---|---|---|---|---|
| Days post Infection | Infected (%) | Disseminated (%) | Median copies in Bodies/Heads (N) | Percentiles (25-75%) | Infected (%) | Disseminated (%) | Median copies in Bodies/Heads (N) | Percentiles (25 and 75%) | Infected (%) | Disseminated (%) | Median copies in Bodies/Heads (N) | Percentiles (25 and 75%) |
| 0 | 100 | 20 | 10.2 (10) n.s. | 10.0-10.4 | 100 | 20 | 10.2 (10) | 9.8-10.6 | 100 | 10 | 10.0 (10) n.s. | 9.8-10.5 |
| 2 | 80 | 0 | 9.1 (8) n.s. | 8.5-9.4 | 50 | 30 | 9.6 (5) | 9.3-10.2 | 70 | 40 | 9.5 (7) n.s. | 9.2-9.8 |
| 4 | 20 | 0 | 7.8 (2)* | 7.3-8.2 | 60 | 60 | 10.4 (6) | 9.7-10.8 | 50 | 30 | 10.0 (5) n.s. | 9.6-11.7 |
| 7 | 10 | 0 | 7.3 (1) n.a. | n.a. | 100 | 100 | 11.1 (10) | 10.8-11.26 | 100 | 90 | 10.39 (10)* | 8.4-10.8 |
| 10 | 0 | 0 | (0) n.a. | n.a. | 60 | 60 | 10.8 (6) | 10.6-10.9 | 90 | 90 | 10.6 (10) n.s. | 10.4-11.3 |
| 14 | 17 | 0 | 7.7 (3)** | 6.7-8.0 | 85 | 100 | 11.8 (26) | 10.9-11.9 | 80 | 90 | 11.3 (23)* | 10.3-11.6 |

*indicate $P < 0.05$,
**$P < 0.01$,
***$P < 0.001$ by Mann Whitney-U tests for the comparisons of PGYP.out and Cairns3 each against PGYP.out.tet;
n.s. non-significant;
n.a. not applicable.

TABLE 5

Quantification of DENV-2 RNA after intrathoracic injection in different mosquito lines. Data from four independent experiments.

| Experiment | DPI[a] | Line | Mosquito Part[b] | Mean Copies | SEM[c] | n |
|---|---|---|---|---|---|---|
| | | | Genomic (+) RNA | | | |
| 1 | 5 | PGYP1 | T + H | 48.58 | 28.71 | 5 |
|   |   | PGYP1.tet | T + H | 21368.13 | 1998.85 | 5 |
|   |   | PGYP1.out | T + H | 40.69 | 9.36 | 5 |
|   |   | PGYP1.out.tet | T + H | 9064.83 | 2033.46 | 4 |
|   |   | PGYP1 | Abd. | 6.44 | 6.44 | 5 |
|   |   | PGYP1.tet | Abd. | 6357.29 | 684.98 | 5 |
|   |   | PGYP1.out | Abd. | 2.22 | 2.22 | 5 |
|   |   | PGYP1.out.tet | Abd. | 10753.91 | 3840.28 | 4 |
| 1 | 14 | PGYP1 | Whole | 25.24 | 4.07 | 2 |
|   |    | PGYP1.tet | Whole | 211350.19 | 38687.90 | 8 |
|   |    | PGYP1.out | Whole | 16.48 | 3.25 | 7 |
|   |    | PGYP1.out.tet | Whole | 231296.71 | 35561.87 | 8 |
| 2 | 5 | PGYP1 | T + H | 32.16 | 5.62 | 4 |
|   |   | PGYP1.tet | T + H | 50433.40 | 9985.28 | 5 |
|   |   | PGYP1 | Abd. | 10.58 | 2.77 | 4 |
|   |   | PGYP1.tet | Abd. | 10511.37 | 2342.27 | 5 |
| 2 | 14 | PGYP1 | Whole | 28.39 | 24.95 | 8 |
|   |    | PGYP1.tet | Whole | 269158.77 | 79320.07 | 7 |
| 3 | 5 | PGYP1 | T + H | 67.45 | 28.53 | 5 |
|   |   | PGYP1.tet | T + H | 105011.05 | 8693.71 | 5 |
|   |   | PGYP1.out | T + H | 4406.69 | 4207.19 | 5 |
|   |   | PGYP1.out.tet | T + H | 91941.97 | 33514.55 | 5 |
|   |   | PGYP1 | Abd. | 48.46 | 4.51 | 5 |
|   |   | PGYP1.tet | Abd. | 104850.10 | 21403.17 | 5 |
|   |   | PGYP1.out | Abd. | 1907.65 | 1851.03 | 5 |
|   |   | PGYP1.out.tet | Abd. | 24685.36 | 12919.93 | 4 |
| 3 | 14 | PGYP1 | Whole | 4934.45 | 1164.91 | 7 |
|   |    | PGYP1.tet | Whole | 360293.19 | 44383.67 | 7 |
|   |    | PGYP1.out | Whole | 10576.99 | 8870.23 | 7 |
|   |    | PGYP1.out.tet | Whole | 374720.72 | 69313.16 | 7 |
| 4 | 5 | PGYP1 | T + H | 222.85 | 216.20 | 5 |
|   |   | PGYP1.tet | T + H | 58325.94 | 17090.05 | 5 |
|   |   | PGYP1.out | T + H | 25.39 | 6.15 | 5 |
|   |   | PGYP1.out.tet | T + H | 44368.94 | 8846.02 | 5 |

TABLE 5-continued

Quantification of DENV-2 RNA after intrathoracic injection in different mosquito lines. Data from four independent experiments.

| Experiment | DPI[a] | Line | Mosquito Part[b] | Mean Copies | SEM[c] | n |
|---|---|---|---|---|---|---|
| | | PGYP1 | Abd. | 0 | 0 | 5 |
| | | PGYP1.tet | Abd. | 9921.17 | 3210.77 | 5 |
| | | PGYP1.out | Abd. | 0 | 0 | 5 |
| | | PGYP1.out.tet | Abd. | 18377.48 | 7324.38 | 5 |
| 4 | 14 | PGYP1.out | Whole | 19.02 | 6.05 | 7 |
| | | PGYP1.out.tet | Whole | 173642.11 | 31279.92 | 7 |
| Anti-genomic (−) RNA | | | | | | |
| 1 | 5 | PGYP1 | T + H | 3.31 | 1.43 | 5 |
| | | PGYP1.tet | T + H | 2894.63 | 415.72 | 5 |
| | | PGYP1.out | T + H | 2.71 | 0.67 | 5 |
| | | PGYP1.out.tet | T + H | 2085.81 | 441.10 | 4 |
| | | PGYP1 | Abd. | 2.02 | 2.02 | 5 |
| | | PGYP1.tet | Abd. | 1787.10 | 324.89 | 5 |
| | | PGYP1.out | Abd. | 3.58 | 1.86 | 5 |
| | | PGYP1.out.tet | Abd. | 2659.96 | 921.85 | 4 |
| 1 | 14 | PGYP1 | Whole | 2.30 | 0.48 | 2 |
| | | PGYP1.tet | Whole | 30003.31 | 5917.62 | 8 |
| | | PGYP1.out | Whole | 1.89 | 0.42 | 7 |
| | | PGYP1.out.tet | Whole | 22630.82 | 3203.45 | 8 |
| 2 | 5 | PGYP1 | T + H | 10.10 | 3.26 | 5 |
| | | PGYP1.tet | T + H | 1792.76 | 566.52 | 5 |
| | | PGYP1.out | T + H | 44.60 | 16.31 | 4 |
| | | PGYP1.out.tet | T + H | 7507.95 | 1947.03 | 5 |
| | | PGYP1 | Abd. | 3.31 | 1.16 | 4 |
| | | PGYP1.tet | Abd. | 2720.41 | 948.94 | 5 |
| | | PGYP1.out | Abd. | 23.45 | 4.05 | 4 |
| | | PGYP1.out.tet | Abd. | 7217.09 | 3314.48 | 5 |
| 2 | 14 | PGYP1 | Whole | 560.26 | 512.60 | 8 |
| | | PGYP1.tet | Whole | 31931.67 | 9092.21 | 8 |
| 3 | 5 | PGYP1 | T + H | 28.47 | 9.64 | 5 |
| | | PGYP1.tet | T + H | 9172.11 | 2363.80 | 5 |
| | | PGYP1 | Abd. | 35.24 | 3.88 | 5 |
| | | PGYP1.tet | Abd. | 31911.28 | 8267.71 | 5 |
| 3 | 14 | PGYP1 | Whole | 2096.00 | 752.44 | 8 |
| | | PGYP1.tet | Whole | 72146.55 | 9500.18 | 8 |
| | | PGYP1.out | Whole | 18011.17 | 11279.89 | 8 |
| | | PGYP1.out.tet | Whole | 55719.18 | 8865.57 | 8 |
| 4 | 5 | PGYP1 | T + H | 7.97 | 6.06 | 5 |
| | | PGYP1.tet | T + H | 4389.66 | 956.66 | 5 |
| | | PGYP1.out | T + H | 2.31 | 0.52 | 5 |
| | | PGYP1.out.Tet | T + H | 4977.24 | 983.62 | 5 |
| | | PGYP1 | Abd. | 0 | 0 | 5 |
| | | PGYP1.tet | Abd. | 3108.85 | 510.51 | 5 |
| | | PGYP1.out | Abd. | 1.57 | 1.57 | 5 |
| | | PGYP1.out.Tet | Abd. | 4643.40 | 465.31 | 5 |
| 4 | 14 | PGYP1.out | Whole | 12.16 | 4.19 | 8 |
| | | PGYP1.out.Tet | Whole | 29279.24 | 3677.83 | 8 |

[a]DPI = Days post-infection
[b]T + H = Mosquito Thorax + Head; Abd. = Abdomen
[c]SEM = Standard Error of Means

TABLE 6

Oligonucleotide sequences. The following table presents the primer sequences used for DENV-2, *Plasmodium gallinaceum*, CHIKV and *Wolbachia* detections as well as for the immune related genes analysis.

| Target Gene | Primer Sequence (5'-3') |
|---|---|
| SPZ5 (AAEL001929) | Fw CGGATTCTCGCCAACGAAGAA (SEQ ID NO: 22) Rv TCTGTTGGTAATGCTGCTGCTGC (SEQ ID NO: 23) |
| REL1 (AAEL007696-RA) | Fw TGGTGGTGGTGTCCTGCGTAAC (SEQ ID NO: 24) Rv CTGCCTGGCGTGACCGTATCC (SEQ ID NO: 25) |
| IMD (AAEL010083) | Fw AACAGACGCAGCAATCATTCCG (SEQ ID NO: 26) Rv GGACTTAGAAGTTGATCTGGTGCAGTG (SEQ ID NO: 27) |
| REL2 (AAEL007624-RA) | Fw GCTCAGTGCTACCGTGGGAAAC (SEQ ID NO: 28) Rv CGGGTTCGCTCTGGCATTTGTC (SEQ ID NO: 29) |
| DOME (AAEL012471) | Fw AAGATGTTCGTAACGACTCGGTCATT (SEQ ID NO: 30) Rv GGTGAGATTGTACGTAACATGATCGGTAT (SEQ ID NO: 31) |
| SOCS36E (AAEL000393) | Fw CGACAACGTAGGAAGAATAAGCCATT (SEQ ID NO: 32) Rv AGCTGGTAATCTTCTGCAAATCCG (SEQ ID NO: 33) |
| CECG (AAEL015515-RA) | Fw TCACAAAGTTATTTCTCCTGATCG (SEQ ID NO: 34) Rv GCTTTAGCCCCAGCTACAAC (SEQ ID NO: 35) |
| DEFC (AAEL003832-RA) | Fw TTGTTTGCTTCGTTGCTCTTT (SEQ ID NO: 36) Rv ATCTCCTACACCGAACCCACT (SEQ ID NO: 37) |
| TEP20 (AAEL001794-RB) | Fw TTCAGTGGCTTTCAGCAATTCTGTC (SEQ ID NO: 38) Rv GCGATCTGCACTTTGAACAAGCA (SEQ ID NO: 39) |
| CTL (AAEL011619-RA) | Fw GCAGTGTATGAATTCGTTCCAATCAACTA (SEQ ID NO: 40) Rv TCCAGGCTTCCAAGAACGTTAGGT (SEQ ID NO: 41) |
| FREP18 (AAEL006704-RA) | Fw TTCTGGTGTGTCTGGTGCTATTCAACA (SEQ ID NO: 42) Rv GCTTCCACGAACATGAGGTTCATAGC (SEQ ID NO: 43) |
| RpS17 | Fw CACTCCCAGGTCCGTGGTAT (SEQ ID NO: 44) Rv GGACACTTCCGGCACGTAGT (SEQ ID NO: 45) |
| DENV-2 NS5 | Fw ACAAGTCGAACAACCTGGTCCAT (SEQ ID NO: 46) Rv GCCGCACCATTGGTCTTCTC (SEQ ID NO: 47) |
| Plasm ssurRNA | Fw GCTTCTTAGAGGGACATTGTGTG (SEQ ID NO: 48) Rv GCGTGCAGCCTAGTTCATC (SEQ ID NO: 49) |
| Actin | Fw ACCGAGCGTGGCTACTCCTT (SEQ ID NO: 50) Rv AGCGACGTAGCACAGCTTCTC (SEQ ID NO: 51) |

TABLE 7

Genetic differences between wMelPop and wMelPop-CLA.

| Gene* | Putative function | wMelPop-CLA features |
|---|---|---|
| WD0200 | Hypothetical protein | SNP (C to T) |
| | | Aminoacid changed from Asp to Asn |
| WD0413 | Aspartyl-tRNA synthetase (asoS) [6.1.1.12] | 10 bp deletion in wMelPop-CLA |
| | | Creates frameshift and premature stop in WD0413 |
| WD0765-WD0766 | Na+/H+ ion antiporter familiy protein/ANK domain protein | IS5 insertion in intergenic space |
| | | Affects expression of both genes |
| WD0758 | Glutaredoxin family protein | G insertion |
| | | Creates frameshift and premature stop in WD0758 |
| WD0506 | Reverse transcriptase, authentic frameshift | Gene absent in wMelPop-CLA |
| WD0507 | DNA repair protein RadC, truncation | Gene absent in wMelPop-CLA |
| WD0508 | Transcriptional regulator, putative | Gene absent in wMelPop-CLA |
| WD0509 | DNA mismatch repair protein MutL-2 | Gene absent in wMelPop-CLA |
| WD0510 | Ribonuclease, degenerate | Gene absent in wMelPop-CLA |
| WD0511 | Conserved hypothetical protein | Gene absent in wMelPop-CLA |
| WD0512 | Hypothetical protein | Gene absent in wMelPop-CLA |
| WD0513 | Hypothetical protein | Gene absent in wMelPop-CLA |
| WD0514 | Ankyrin repeat domain protein | Gene absent in wMelPop-CLA |
| WD0515 | Reverse transcriptase, interruption-C | Gene absent in wMelPop-CLA |
| WD0516 | Transposase, IS5 family, OrfB | Gene absent in wMelPop-CLA |
| WD0517 | Transposase, IS5 family, OrfA | Gene absent in wMelPop-CLA |
| WD0518 | Reverse transcriptase, interruption-N | Gene absent in wMelPop-CLA |

*The name and annotation of the genes is based on the annotation of the closely related wMel genome, fully sequenced by our group (Wu et al., 2004)

References

Allemand, R., Pompanon, F., Fleury, F., Fouillet, P. and Bouletreau, M. (1994). *Physiol Entomol* 19: 1-8.

Altschul, S. F., Madden, T. L., Schaffer, A. A., Zhang, J., Zhang, Z., Miller, W., and Lipman, D. J. (1997). Gapped BLAST and PSI-BLAST: a new generation of protein database search programs. *Nucleic Acids Res* 25: 3389-3402.

Ashburner, M. (1989). *Drosophila*: A Laboratory Manual. Cold Spring Harbor Laboratory Press, Plainview, N.Y.

Ashburner, M. and Roote, J. (2000). Laboratory Culture of *Drosophila*, pp. 585-599. W. Sullivan, M. Ashburner, and R. S. Hawley (ed.), *Drosophila Protocols*. Cold Spring Harbor Press, Cold Spring Harbor, N.Y.

Ayres, J. S., Schneider, D. S. (2008). A signaling protease required for melanization in *Drosophila* affects resistance and tolerance of infections. *PLoS Biol* 6: 2764-2773.

Ball, L. A., Johnson, K. L. (1998). Nodaviruses of insects. In: Miller L K, Ball L A, editors. The Insect Viruses. New York: Plenum Publishing Corporation. pp. 225-267.

Ballard, J. W. (2000). Comparative genomics of mitochondrial DNA in *Drosophila simulans*. *J Mol Evol* 51: 64-75.

Bonatz, A. E., Steiner, H. and Huston, J. P. (1987). *J Neurosci Methods* 22: 13-26.

Bourtzis, K., Pettigrew, M. M. and O'Neill, S. L. (2000). *Insect Mol Biol.* 9: 635.

Boyle, L., O'Neill, S. L., Robertson, H. M. and Karr, T. L. (1993). *Science* 260: 1796-9.

Braig, H. R., Zhou, W., Dobson, S. L. and O'Neill, S. L. (1998). *J Bacteriol* 180: 2373.

Broom A. K. et al. (1998). *Pathology* 30: 286.

Brownstein, J. S., Hett, E. and O'Neill, S. L. (2003). *J. Invert. Pathol.* 84: 24.

Brun, G. and Plus, N. (1980). The viruses of *Drosophila*. In: Ashburner M, Wright T F R, editors. The Genetics and Biology of *Drosophila*. New York: Academic Press. pp. 625-702.

Casiraghi M., Bordenstein S. R., Baldo L., Lo N., Beninati T. et al. (2005). Phylogeny of *Wolbachia pipientis* based on gltA, groEL and ftsZ gene sequences: clustering of arthropod and nematode symbionts in the F supergroup, and evidence for further diversity in the *Wolbachia* tree. *Microbiology* 151: 4015-4022.

Cherry, S., Kunte, A., Wang, H., Coyne, C., Rawson, R. B. et al. (2006). COPI activity coupled with fatty acid biosynthesis is required for viral replication. *PLoS Pathog* 2: e102.

Cherry, S., Perrimon, N. (2004) Entry is a rate-limiting step for viral infection in a *Drosophila melanogaster* model of pathogenesis. *Nat Immunol* 5: 81-87.

Christian P. D., Carstens E. B., Domier L., Johnson J. E., Johnson K. N. et al. (2005). Dicistroviridae. In: Fauquet C M, Mayo M A, Maniloff J, Desselberger U, Ball L A, editors. *Virus taxonomy: Eighth report of the International Committee on the Taxonomy of Viruses*. San Diego: Elsevier Academic Press. pp. 783-788.

Cook P. E. et al. (2006). *Proc. Natl. Acad. Sci. U.S.A.* 103: 18060.

Curtis, C. F., and Sinkins, S. P. (1998). *Parasitology* 116 Suppl: S111-5.

Dobson, S. L., Bourtzis, K., Braig, H. R., Jones, B. F., Zhou, W., Rousset, F. and O'Neill, S. L. (1999). *Insect Biochem. Mol. Biol.* 29: 153-60.

Dobson, S. L., Marsland, E. J., Veneti, Z., Bourtzis, K. and O'Neill, S. L. (2002). *Appl. Environ. Microbiol.* 68: 656-60.

Dobson, S. L. and Rattanadechakul, W. (2001). *J. Med. Entomol.* 38: 844.

Duron, O., Boureux, A., Echaubard, P., Berthomieu, A., Berticat, C. et al. (2007). Variability and expression of ankyrin domain genes in *Wolbachia* variants infecting the mosquito *Culex pipiens*. *J Bacteriol* 189: 4442-4448.

Dye C. (1992). *Annu. Rev. Entomol.* 37: 1.

Feinberg, M. D., Szumowski, K. M. and Harris, K. M. (2001). R. T. Giberson and R. S. Demaree Jr (ed.), *Microwave Protocols for Microscopy* Humana Press, Totowa, N.J.

Fuery, C. J., Withers, P. C., Hobbs, A. A. and Guppy, M. (1998). *Comp Biochem Physiol A Mol Integr Physiol* 119: 469-476.

Garrett-Jones, C. (1964). *Nature* 204: 1173.

Gerberg, E. J., Barnard, D. R. and Ward, R. A. (1994). Manual for mosquito rearing and experimental techniques. *Lake Charles, La.: American Mosquito Control Association*.

Gilles, H. M. and Warrell, D. A. (2002). *Essential Malariology* (Arnold, London, 4th ed).

Giordano, R., O'Neill, S. L., Robertson, H. M. (1995) *Wolbachia* infections and the expression of cytoplasmic incompatibility in *Drosophila sechellia* and *D. mauritiana*. *Genetics* 140: 1307-1317.

Grobbelaar, J. H., Morrison, G. J., Baart, E. E. and Moran, V. C. (1967). *J Insect Physiol* 13: 1843-1848.

Gubler, D. J. (1997). Dengue and Dengue Hemorrhagic Fever. D. J. Gubler, G. Kuno, Eds. (CAB International, New York, N.Y.), pp. 1-22.

Haine, E. R. (2008). Symbiont-mediated protection. *P R SOC B* 275: 353-361.

Hall, R. A., Burgess, G. W., Kay, B. H. and Clancy, P. (1991). *Immunol Cell Biol* 69: 47.

Hedges, L. M. and Johnson, K. N. (2008) *J. Gen. Virol.* 89, 1497-1501.

Hoffmann, A. A., Clancy, D., Duncan, J. (1996). Naturally-occurring *Wolbachia* infection in *Drosophila simulans* that does not cause cytoplasmic incompatibility. *Heredity.* 76: 1-8.

Hoffmann, A. A. and Turelli, M. (1997). S. L. O'Neill, A. A. Hoffmann, J. H. Werren, Eds. (Oxford University Press, Oxford, UK), pp. 42-80.

Hoffmann, A. A., Turelli, M. and Simmons G. M. (1986). *Evolution* 40: 692-701.

Holmes, D. S. and Bonner J. (1973). *Biochemistry* 12: 2330-8.

Huszar, T. and Imler, J. L. (2008). *Adv Virus Res* 72: 227.

Ijichi, N., Kondo, N., Matsumoto, R., Shimada, M., Ishikawa, H., et al. (2002). Internal spatiotemporal population dynamics of infection with three *Wolbachia* strains in the adzuki bean beetle, *Callosobruchus chinensis* (Coleoptera: Bruchidae). *Appl Environ Microbiol* 68: 4074-4080.

Iturbe-Ormaetxe, I., Burke, G. R., Riegler, M. and O'Neill S. L. (2005). *J. Bacteriol.* 187: 5136-45.

Janzen, H. G., Wright, K. A. (1971) *Canadian Journal of Zoology.* 49: 1343-1345.

Jobling, B. (1987). The mosquito *Aedes aegypti*. In Anatomical drawings of biting flies, B. Jobling, ed. (London, British Museum (Natural History), Welcome Trust), pp. 47-80.

Joehanes, R. and Nelson, J. C. (2008). *Bioinformatics* 24: 2788.

Johnson, K. N. and Christian, P. D. (1998). *J. Gen. Virol.* 79: 191-203.

Johnson, K. N. and Christian, P. D. (1996). *Arch. Virol.* 141: 1509-1522.

Johnson, K. N., Johnson, K. L., Dasgupta, R., Gratsch, T. and Ball, L. A. (2001). *J. Gen. Virol.* 82, 1855-1866.

Jousset, F. X., Plus, N., Croizier, G., Thomas, M. (1972). Existence chez *Drosophila* de deux groupes de picornavirus de propriétés sérologiques et biologiques différentes. *C R Acad Sci* (Paris) 275: 3043-3046.

Kang, L., Ma, X., Cai, L., Liao, S., Sun, L., Zhu, H., Chen, X., Shen, D., Zhao, S. and Li, C. (2003). *Heredity* 90: 71-6.

Kawada, H. and Takagi, M. (2004). *J Medical Entomol* 41: 873-881.

Kittayapong, P., Baisley, K. J. Baimai, V. and O'Neill, S. L. (2000). *J. Med. Entomol.* 37:340-5.

Knox, T. B., Kay, B. H., Hall, R. A. and Ryan, P. A. (2003). *J Med Entomol* 40:950.

Kopek, B. G., Perkins, G., Miller, D. J., Ellisman, M. H., Ahlquist, P. (2007). Three-dimensional analysis of a viral RNA replication complex reveals a virus-induced mini-organelle. *PLoS Biol* 5: e220.

Krettli, A. U., Rocha, E. M., Lopes, J. D., Carneiro, C. R., Kamboj, K. K., Cochrane, A. H., and Nussenzweig, R. S. (1988). Circumsporozoite protein of *Plasmodium gallinaceum* characterized by monoclonal antibodies. *Parasite Immunol* 10, 523-533.

Kuno, G. (1983). *In Vitro* 19: 707-13.

Lautié-Harivel, N., Thomas-Orillard, M. (1990). Location of *Drosophila* C virus target organs in *Drosophila* host by immunofluorescence technique. *Biol Cell* 69: 35-39.

Lighton, J. R. B. (1991). *Concise Encyclopedia on Biological and Biomedical Measurement Systems*, (ed. P. A. Payne), pp. 201-208. Oxford: Pergamon Press.

Lighton, J. R. B. and Duncan, F. D. (2002). *Ecology* 83: 3517-3522.

Lipsitch, M. and Moxon, E. R. (1997). *Trends Microbiol.* 5: 31.

Liseichikov, Y. N. and Zakharevskii, A. S. (1978). *Bull Exp Biol Med* 85: 696-697.

Lobo, N. F., Clayton, J. R., Fraser, M. J., Kafatos, F. C. and Collins, F. H. (2006). *Nat. Protoc.* 1: 1312.

MacDonald, G. (1957). *The Epidemiology and Control of Malaria*. (Oxford University Press, London).

Mankin, R. W. (1994). *J Am Mosq Control Assoc* 10: 302-308.

Marhoul, Z. and Pudney, M. (1972). *Trans. R. Soc. Trop. Med. Hyg.* 66:183-4.

Mateos, M., Castrezana, S. J., Nankivell, B. J., Estes, A. M., Markow, T. A. and Moran, N. A. (2006). *Genetics* 174: 363-76.

McGraw, E. A., Merritt, D. J., Droller, J. N. and O'Neill, S. L. (2002). *Proc. Natl. Acad. Sci. USA* 99: 2918-23.

Mercot, H., and Poinsot, D. (1998). *Wolbachia* transmission in a naturally bi-infected *Drosophila simulans* strain from New-Caledonia. *Entomologia Experimentalis et Applicata* 86: 97-103.

Miller, D. J., Schwartz, M. D., Ahlquist, P. (2001) Flock House virus RNA replicates on outer mitochondrial membranes in *Drosophila* cells. *J Virol* 75: 11664-11676.

Miller, W. J., Riegler, M. (2006). Evolutionary dynamics of wAu-like *Wolbachia* variants in neotropical *Drosophila* spp. *Appl Environ Microbiol* 72: 826-835.

Min, K. T. and Benzer, S. (1997). *Proc. Natl. Acad. Sci. USA* 94: 10792-6.

Mitsuhashi, J. and Maramorosch, K. (1964). *Contrib. Boyce Thompson Inst.* 22: 435-460.

Morrison, A. C., Zielinski-Gutierrez, E., Scott, T. W. and Rosenberg, R. (2008). *PLoS Med.* 5: e68.

Nasci, R. S. (1986). *Journal of the American Mosquito Control Association* 2: 61-2.

Novak, M. G., Ribeiro, J. M. C. and Hildebrand J. H. (1995). *Journal of Experimental Biology* 198: 167.

Nubel, U., Engelen, B., Felske, A., Snaidr, J., Wieshuber, A., Amann, R. I., Ludwig, W. and Backhaus, H. (1996). *J. Bacteriol.* 178: 5636-43.

O'Neill, S. L., Giordano, R., Colbert, A. M., Karr, T. L. and Robertson, H. M. (1992). *Proc. Natl. Acad. Sci. USA* 89:2699-702.

O'Neill, S. L., Karr, T. L. (1990). Bidirectional incompatibility between conspecific populations of *Drosophila simulans*. *Nature* 348: 178-180.

O'Neill, S. L., Pettigrew, M. M., Sinkins, S. P., Braig, H. R., Andreadis, T. G. and Tesh, R. B. (1997). *Insect Mol. Biol.* 6: 33-9.

Panteleev, D. Y., Goryacheva II, Andrianov, B. V., Reznik, N. L., Lazebny, 0. E. et al. (2007) The endosymbiotic bacterium *Wolbachia* enhances the nonspecific resistance to insect pathogens and alters behavior of *Drosophila melanogaster*. *Russian Journal of Genetics* 43: 1066-1069.

Pfaffl, M. W. (2001). *Nucleic Acids Res.* 29: e45.

Pfaffl, M. W., Horgan, G. W., and Dempfle, L. (2002). Relative expression software tool (REST) for group-wise comparison and statistical analysis of relative expression results in real-time PCR. Nucleic Acids Res 30, e36.

Pittman, G. W., Brumbley, S. M., Allsopp, P. G. and O'Neill, S. L. (2008). *Appl. Environ. Microbiol.* 74: 762-7.

Poinsot, D., Bourtzis, K., Markakis, G., Savakis, C., and Mercot H. (1998) *Wolbachia* transfer from *Drosophila melanogaster* into *D. simulans*: Host effect and cytoplasmic incompatibility relationships. *Genetics* 150: 227-237.

Rasgon, J. L., Styer, L. M. and Scott, T. W. (2003). *J. Med. Entomol.* 40: 125.

Rasgon, J. L., and Scott, T. W. (2004). *J. Med. Entomol.* 41:255-7.

Reynolds, D. R. and Riley, J. R. (2002). *Comp Electron Agric* 35: 271-307.

Reynolds, K. T., Thomson, L. J. and Hoffmann, A. A. (2003). *Genetics* 164: 1027-34.

Ribeiro, J. M. C., Rossignol, P. A., Spielman, A. (1984). *Journal of Experimental Biology* 108: 1-7.

Ricci, I., Cancrini, G., Gabrielli, S., D'Amelio, S. and Favia, G. (2002). *J. Med. Entomol.* 39: 562-7.

Richardson, J., Molina-Cruz A. and Salazar, M. I. (2006). *B. W. 4th., Am J Trop Med Hyg.* 74: 132.

Riegler, M., Charlat, S., Stauffer, C. and Mercot, H. (2004). *Appl. Environ. Microbiol.* 70: 273-9.

Riegler, M., Sidhu, M., Miller, W. J. and O'Neill, S. L. (2005). *Curr. Biol.* 15: 1428-1433.

Rigaud, T., Pennings, P. S. and Juchault, P. (2001). *J. Invertebr. Pathol.* 77:251-7.

Rodrigues, F. G., Santos, M. N., de Carvalho, T. X., Rocha, B. C., Riehle, M. A., Pimenta, P. F., Abraham, E. G., Jacobs-Lorena, M., Alves de Brito, C. F., and Moreira, L. A. (2008). Expression of a mutated phospholipase $A_2$ in transgenic *Aedes fluviatilis* mosquitoes impacts *Plasmodium gallinaceum* development. Insect Mol Biol 17: 175-183.

Rowley, W. A., Jones, M. D. R., Jacobson, D. W. and Clarke, J. L. (1987). *Ann Entomol Soc Am* 80: 534-538.

Rutledge, L. C., Ward, R. A. and Gould, D. J. (1964). *Mosq News* 24: 407.

Sasaki, J., Nakashima, N. (1999). Translation initiation at the CUU codon is mediated by the internal ribosome entry site of an insect picorna-like virus in vitro. *J Virol* 73: 1219-1226.

Sbalzarini, I. F. and Koumoutsakos, P. (2005). *J Struct Biol* 151: 182-195.

Schellenberg J. R. et al. (2001). *Lancet* 357: 1241.

Schneider, D., and Shahabuddin, M. (2000). Malaria parasite development in a *Drosophila* model. Science 288, 2376-2379.

Schneider, D. S., Ayres J. S. (2008). Two ways to survive infection: what resistance and tolerance can teach us about treating infectious diseases. *Nat Rev Immunol* 8: 889-895.

Schneider, I. (1972). Cell lines derived from late embryonic stages of *Drosophila melanogaster. J Embryol Exp Morph* 27: 353-365.

Scotti, P. D. (1980). *Microbial Control of Insect Pests* J. Kalmakoff, J. F. Longworth, Eds. (Crown, Wellington) pp. 48-55.

Siler, J. F., Hall, M. W. and Hitchens, A. P. (1926). *Philipp. J. Sci.* 29: 1.

Simon C. et al. (1994). *Annals Entomol. Soc. Am.* 87: 651-701.

Sinkins, S. P. (2004). *Insect Biochem Mol Biol* 34: 723.

Sinkins, S. P., Braig, H. R., O'Neill, S. L. (1995) *Wolbachia pipientis*: bacterial density and unidirectional cytoplasmic incompatibility between infected populations of *Aedes albopictus. Experimental Parasitology* 81: 284-291.

Sinkins, S. P. and O'Neill, S. L. (2000). Insect Transgenesis: *Methods and Applications*, A. M. Handler, A. A. James, Eds. (CRC Press, London), pp. 271-287.

Tason de Camargo, M., and Krettli, A. U. (1981). *Aedes fluviatilis* (Lutz), a new experimental host for *Plasmodium gallinaceum* Brumpt. *The Journal of Parasitology* 64: 924-925.

Teixeira, L., Ferreira, A., and Ashburner, M. (2008) The bacterial symbiont *Wolbachia* induces resistance to RNA viral infections in *Drosophila melanogaster.* Plos Biology 6: e1000002. doi:1000010.1001371/journal.pbio.1000002.

Thomas, M. B. and Read, A. F. (2007) *Nat. Rev. Microbiol.* 5: 377.

Tsai, K. H., Lien, J. C., Huang, C. G., Wu, W. J. and Chen, W. J. (2004). *J. Med. Entomol.* 41: 677-83.

Turell, M. J. (1988). Reduced Rift Valley fever virus infection rates in mosquitoes associated with pledget feedings. *Am J Trop Med Hyg* 39: 597-602.

Turelli, M., Hoffmann, A. A. (1991). Rapid spread of an inherited incompatibility factor in California *Drosophila. Nature* 353: 440-442.

Turelli, M., Hoffmann, A. A. (1995) Cytoplasmic incompatibility in *Drosophila simulans*: dynamics and parameter estimates from natural populations. *Genetics* 140: 1319-1338.

Van Meer, M. M., and Stouthamer, R. (1999). *Heredity* 82: 163-9.

Van Voorhies, W. A., Khazaeli, A. A. and Curtsinger, J. W. (2004). *J Appl Physiol* 97: 1915-1922.

Walker, T., Klasson, L., Sebaihia, M., Sanders, M. J., Thomson, N. R. et al. (2007). Ankyrin repeat domain-encoding genes in the wPip strain of *Wolbachia* from the *Culex pipiens* group. *BMC Biol* 5: 39.

Wang X. H. et al. (2006) *Science* 312: 452-454.

Watts, D. M., Burke, D. S., Harrison, B. A., Whitmire, R. E. and Nisalak, A. (1987). *Am. J. Trop. Med. Hyg.* 36: 143.

West, G. B., Woodruff, W. H. and Brown, J. H. (2002). *Proc Natl Acad Sci USA* 99: 2473-2478.

Williams, C. R. and Kokkinn, M. J. (2005). *Physiol. Ecol.* 30: 309-316.

Wilson, J. E., Powell, M. J., Hoover, S. E., Sarnow, P. (2000). Naturally occurring dicistronic cricket paralysis virus RNA is regulated by two internal ribosome entry sites. *Mol Cell Biol* 20: 4990-4999.

Winston, P. W. and Bates, D. H. (1960). *Ecology* 41: 232-237.

Woodring, J. L. Higgs, S. and Beaty, B. J. (1996). The Biology of Disease Vectors, B. J. Beaty, W. C. Marquardt, Eds. (University Press of Colorado, Boulder, Colo.), pp 51-72.

Woolfit, M., Iturbe-Ormaetxe, I., McGraw, E. A. and 'Neill, S. L. (2009). *Mol. Biol. Evol.* 26: 367-374.

Wu, M. et al. (2004). *PLoS Biol.* 2: E69.

Xi, Z. and Dobson, S. L. (2005). *Appl. Environ. Microbiol.* 71: 3199-204.

Xi, Z., Khoo, C. C. and Dobson, S. L. (2005). *Science* 310: 326.

Xi, Z., Ramirez, J. L. and Dimopoulos, G. (2008). *Plos Pathog* 4: e1000098.

Yamada, R., Floate, K. D., Riegler, M. and O'Neill, S. L. (2007). *Genetics* 177: 801-808.

Zabalou, S., Riegler, M., Theodorakopoulou, M., Stauffer, C., Savakis, C. and Bourtzis, K. (2004). *Proc. Natl. Acad. Sci. USA* 101:15042-5.

Zar, J. H. (1999). Biostatistical analysis. Prentice Hall, Upper Saddle River, New Jersey.

Zhou, W., Rousset, F. and O'Neill, S. L. (1998). *Proc. R. Soc. Lond. B.* 265:509-515.

The invention claimed is:

1. A mosquito comprising the isolated mosquito-adapted bacterium wMelPop-CLA or wMel.

2. A method of producing the mosquito of claim 1, said method comprising culturing the wMelPop-CLA or wMel bacterium with one or more mosquito cells, and optionally with one or more differentiating agents, to thereby produce the mosquito.

3. The mosquito of claim 1, wherein said mosquito is of a genus selected from the group consisting of *Culex, Aedes* and *Anopheles*.

4. The mosquito of claim 3, wherein said mosquito is of a species selected from the group consisting of *Aedes aegypti*, and *Anopheles gambiae*.

5. The mosquito of claim 1, wherein one or more eggs from said mosquito has a reduced desiccation tolerance as compared to a corresponding wild-type mosquito.

6. The mosquito of claim 1, wherein said mosquito has a reduced ability to feed from a host as compared to a corresponding wild-type mosquito.

7. The mosquito of claim 1, wherein said mosquito has improved protection against, or resistance to, a pathogen as compared to a corresponding wild-type mosquito.

8. The mosquito of claim 7, wherein said pathogen is selected from the group consisting of a virus, a protozoan, a worm, a bacterium, and a fungus.

9. The mosquito of claim 8, wherein said virus is an arbovirus selected from the group consisting of an alphavirus, a flavivirus, and a bunyavirus.

10. The mosquito of claim 9, wherein said alphavirus is a Chikungunya virus.

11. The mosquito of claim 9, wherein said flavivirus is selected from the group consisting of a dengue virus, a West Nile virus, and a Yellow Fever virus.

12. The mosquito of claim 8, wherein said protozoan is a malaria parasite of the genus *Plasmodium*.

13. The mosquito of claim 12, wherein said malaria parasite is of a species of *Plasmodium* selected from the group consisting of *Plasmodium falciparum, Plasmodium vivax, Plasmodium ovale, Plasmodium malariae, Plasmodium berghei, Plasmodium gallinaceum*, and *Plasmodium knowlesi*.

14. The mosquito of claim 8, wherein said worm is a nematode.

15. The mosquito of claim 14, wherein said nematode is a filarial nematode.

16. The mosquito of claim 8, wherein said bacterium is selected from the group consisting of a Gram negative and a Gram positive bacterium.

* * * * *